US007320857B2

(12) United States Patent
Zhao et al.

(10) Patent No.: US 7,320,857 B2
(45) Date of Patent: Jan. 22, 2008

(54) CHARACTERIZATION OF THE EARLIEST STAGES OF THE SEVERE ACUTE RESPIRATORY SYNDROME (SARS) VIRUS AND USES THEREOF

(75) Inventors: Guoping Zhao, Shanghai (CN); Rui Heng Xu, Guangdong (CN); Xinwei Wu, Guangdong (CN); Changchun Tu, Jilin (CN); Huai-Dong Song, Shanghai (CN); Yixue Li, Shanghai (CN); Jinlin Hou, Guangdong (CN); Jun Xu, Guangdong (CN); Jun Min, Guangdong (CN)

(73) Assignee: Chinese National Human Genome Center at Shanghai, Shanghai (CN)

( * ) Notice: Subject to any disclaimer, the term of this patent is extended or adjusted under 35 U.S.C. 154(b) by 9 days.

(21) Appl. No.: 10/888,401

(22) Filed: Jul. 9, 2004

(65) Prior Publication Data

US 2005/0112554 A1 May 26, 2005

(51) Int. Cl.
*C12Q 1/70* (2006.01)
*C12Q 1/68* (2006.01)
*C07H 21/02* (2006.01)

(52) U.S. Cl. .................... 435/5; 435/6; 536/24.32; 536/23.72

(58) Field of Classification Search ............... 435/5, 435/235.1; 536/24.32, 23.72
See application file for complete search history.

(56) References Cited

OTHER PUBLICATIONS

Science 303:1666-1669 (Mar. 12, 2004; published online Jan. 29, 2004).*
Guan et al, Science 302:276-278 (Oct. 10, 2003, published online Sep. 4, 2003).*
Qin et al, Genomics Proteomics & Bioinformatics 1(2): 90-100 (May 2003).*
Genbank accession AY278389.2 (Jun. 5, 2003).*
Ruan et al, Lancet 361:1779-1785 (May 24, 2003, published online May 9, 2003).*
"Identification of a Novel Coronavirus in Patients with Severe Acute Respiratory Syndrome" by Christian Drosten, M.D., et al., *The New England Journal of Medicine*, vol. 348, No. 20, pp. 1967-1976, www.nejm.org (May 15, 2003).
"Isolation and Characterization of Viruses Related to the SARS Coronavirus from Animals in Southern China" by Y. Guan, et al., *Science*, vol. 302, pp. 276-278, www.sciencemag.org (Oct. 10, 2003).
"Mutation analysis of 20 SARS Virus Genome Sequences: Evidence for Negative Selection in Replicase ORF1b and Spike Gene[1]" by HU Lan-Dian, et al., *Acta Phamacol Sin*, vol. 8, pp. 741-745 (Aug. 24, 3003).

"The Genome Sequence of the SARS-Associated Coronavirus" by Marco A. Marra, et al., *Science*, vol. 300, pp. 1399-1404, www.sciencemag.org (May 30, 2003).
"Characterization of a Novel Coronavirus Associated with Severe Acute Respiratory Syndrome" by Paul A. Rota, et al., *Science*, vol. 300, pp. 1394-1399, www.sciencemag.org (May 30, 2003).
"Comparative full-length genome sequence analysis of 14 SARS coronavirus isolates and common mutations associated with putative origins of infection" by YiJun Ruan, et al., *The Lancet*, vol. 361, pp. 1779-1785, www.thelancet.com (May 24, 2003).
"SARS—Beginning to Understand a New Virus" by Konrad Stadler, et al., *Microbiology*, vol. 1, pp. 209-218 (Dec. 2003).
"Molecular Evolution of the SARS Coronavirus During the Course of the SARS Epidemic in China" by The Chinese SARS Molecular Epidemiology Consortium, *Science*, vol. 303, pp. 1666-1669, www.sciencemag.org, (Mar. 12, 2004).
"Molecular Evolution of the SARS Coronavirus During the Course of the SARS Epidemic in China" by The Chinese SARS Molecular Epidemiology Consortium, *Sciencexpress*, www.sciencexpress.org, pp. 1-4, (Jan. 29, 2004).
"Unique and Conserved Features of Genome and Proteome of SARS-coronavirus, and Early Split-Off From the Coronavirus Group 2 Lineage" by Eric J. Snijder, et al., *J. Mol. Biol.*, vol. 331, pp. 991-1004 (2003).
"SARS coronavirus TOR2, complete genome" from Database EMBL (online), pp. 1-12 (Apr. 15, 2003).
"SARS coronavirus GD01, complete genome" from Database EMBL (online), pp. 1-13 (Apr. 22, 2003).
"Bioinformatics analysis of SARS coronavirus genome polymorphism" by G.M. Pavlovic-Lazetic, et al., *BMC Bioinformatics, BioMed Central*, vol. 5, No. 1, pp. 1-14 (May 25, 2004).

* cited by examiner

*Primary Examiner*—Bruce R. Campell
*Assistant Examiner*—Bo Peng
(74) *Attorney, Agent, or Firm*—David G. Rosenbaum; J. Peter Paredes; Rosenbaum & Associates, PC

(57) ABSTRACT

Severe Acute Respiratory Syndrome ("SARS") is a human respiratory disease of recent origin, widespread infectivity, recurring incidence, and significant mortality. Although there is abundant evidence suggesting that the coronavirus responsible for the disease ("SARS-CoV") evolves during an outbreak, there is currently little data on the earliest strains of this coronavirus. The present invention is directed to the characterization of the genomic RNA sequences of these earliest SARS coronaviruses, to the identification of nucleotide positions within the SARS-CoV genomic RNA that are characteristic of the different evolutionary stages of the coronavirus, to kits based on these positions for use in diagnosis of the disease in patients, and for the development of vaccines to the disease based on the lowered virulence and contagiousness of these earliest strains of SARS-CoV.

6 Claims, 35 Drawing Sheets

Figure 1B-1:
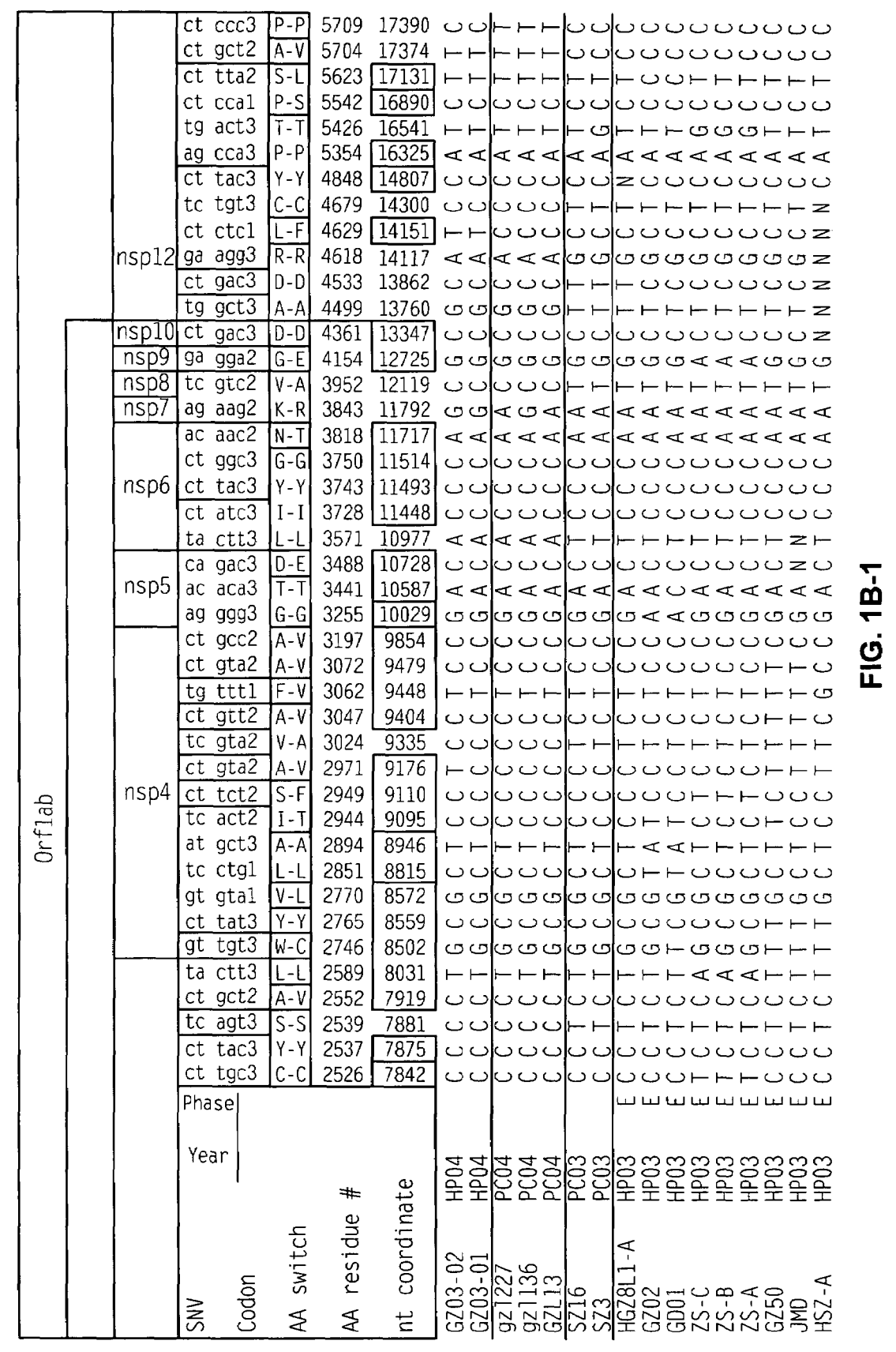

(Figure content: a large data table showing SNV, Codon, AA switch, AA residue #, nt coordinate and sample columns across various nsp regions of Orf1ab; table too dense to reliably transcribe cell-by-cell.)

FIG. 1B-2

| | | Codon | AA switch | AA residue # | nt coordinate | GZ03-02 | GZ03-01 | gz1227 | gz1136 | GZL13 | SZ16 | SZ3 | HGZ8L1-A | GZ02 | GD01 | ZS-C | ZS-B | ZS-A | GZ50 | JMD | HSZ-A |
|---|---|---|---|---|---|---|---|---|---|---|---|---|---|---|---|---|---|---|---|---|---|
| | | ta aat3 | N-K | 479 | 22928 | T | T | A | A | A | A | T | T | T | T | T | T | T | T | T | T |
| | | ag aat2 | N-S | 479 | 22927 | A | A | A | G | G | A | A | A | A | A | A | A | A | A | A | A |
| | | tc ctt2 | L-P | 472 | 22906 | C | C | C | C | C | T | T | T | T | T | T | T | T | T | T | T |
| | | ct tcc3 | S-S | 461 | 22874 | T | T | T | T | T | C | C | C | C | C | C | C | C | C | C | C |
| | | tc ttt2 | F-S | 360 | 22570 | C | C | C | C | C | C | C | T | T | T | T | T | T | T | T | N |
| | | ct tct2 | S-F | 353 | 22549 | C | C | C | C | C | C | C | C | C | C | C | C | C | C | C | N |
| | | ga aaa2 | R-K | 344 | 22522 | G | G | G | G | G | G | G | G | G | G | G | G | G | A | G | N |
| | | ga aga3 | R-R | 342 | 22517 | G | G | G | G | G | G | G | G | G | G | G | G | G | A | G | N |
| | | ag gga1 | R-G | 311 | 22422 | G | G | G | G | G | G | G | A | A | A | A | A | A | A | G | N |
| | | ca aca2 | T-K | 261 | 22273 | C | C | C | C | C | A | A | C | C | C | C | C | C | C | C | N |
| | | ct att2 | T-I | 244 | 22222 | C | C | C | C | C | C | C | C | C | C | C | C | C | C | C | C |
| | | tc tca2 | L-S | 239 | 22207 | C | C | C | C | C | C | C | T | T | T | T | T | T | C | T | C |
| | | ca aac3 | N-K | 227 | 22172 | C | C | C | C | C | A | A | C | C | C | C | C | C | C | N | C |
| | | ct cct3 | P-P | 218 | 22145 | T | T | T | T | T | T | T | T | C | C | T | T | T | T | N | T |
| | | ag cag2 | Q-R | 147 | 21931 | G | G | G | G | G | A | A | A | A | A | A | A | A | N | N | A |
| | | ct gct2 | A-V | 139 | 21907 | T | T | T | T | T | C | C | C | C | C | C | C | C | C | N | C |
| | | ga ggc2 | G-D | 77 | 21721 | A | A | A | A | A | A | A | A | A | A | A | A | A | A | A | A |
| | | cg acg2 | T-R | 75 | 21715 | C | C | C | C | C | C | C | G | C | C | G | G | G | C | G | C |
| | | ac cca3 | P-P | 61 | 21674 | A | A | A | A | A | A | A | A | A | A | A | A | A | A | A | C |
| | | ct tca2 | S-L | 49 | 21637 | C | C | C | C | C | C | C | C | C | C | C | C | C | T | C | C |
| | | tg gct3 | A-A | 27 | 21572 | T | T | T | T | T | T | T | T | T | T | T | T | T | T | T | T |
| | | tc aac3 | N-N | 7072 | 21479 | C | C | C | C | C | C | C | T | T | C | C | C | C | C | C | C |
| | | ac aaa1 | K-Q | 7023 | 21333 | A | A | A | A | A | A | A | A | A | A | A | A | A | A | A | A |
| | | ac gaa3 | E-D | 6992 | 21239 | A | A | A | A | A | A | A | A | A | A | A | A | A | A | A | A |
| | nsp16 | ag agg2 | K-R | 6910 | 20992 | G | G | G | G | G | A | A | A | G | A | A | A | G | G | G | G |
| | | ag gat3 | D-D | 6874 | 20885 | C | C | T | T | T | T | T | T | T | T | T | T | T | T | T | T |
| | | ac caa2 | Q-P | 6862 | 20848 | A | A | A | A | A | A | A | A | A | G | A | A | G | A | A | A |
| | | ag gtg3 | V-V | 6850 | 20840 | A | A | A | A | A | A | A | A | A | G | A | A | G | G | A | A |
| | | tc aat3 | N-N | 6804 | 20675 | T | T | T | T | T | T | T | T | T | T | T | T | T | T | T | T |
| nsp15 | | tc cct2 | P-L | 6540 | 19882 | C | C | C | C | C | C | C | C | C | C | C | C | C | C | C | T |
| | | ag gta3 | V-V | 6525 | 19838 | A | A | A | A | A | A | A | A | A | G | A | A | A | A | A | A |
| | | ct cta1 | L-L | 6409 | 19491 | C | C | C | T | T | C | C | C | C | C | C | C | C | C | C | C |
| | | ag tta3 | L-L | 6381 | 19406 | G | G | G | G | G | A | A | A | A | A | A | A | A | A | A | A |
| nsp14 | | ct aca2 | T-I | 6274 | 19084 | C | C | T | T | T | T | T | C | C | C | C | C | C | C | C | C |
| | | ag gaa3 | E-E | 6267 | 19064 | A | A | A | A | A | A | A | A | A | A | A | A | A | A | A | A |
| | | ta att3 | I-I | 6234 | 18965 | T | T | T | T | T | T | T | T | T | T | T | T | T | T | T | T |
| | | ac aat1 | N-H | 5972 | 18180 | C | A | C | C | C | A | A | A | A | A | A | A | A | A | A | A |
| | | ct cgc3 | R-R | 5861 | 17846 | C | C | C | C | C | C | C | C | C | C | C | C | C | C | C | C |
| | | ct aac3 | N-N | 5820 | 17723 | C | C | C | C | C | T | C | C | T | T | T | C | C | C | C | C |
| | | gt gat3 | E-D | 5767 | 17564 | G | G | G | G | G | G | G | G | G | G | G | G | G | G | G | G |
| nsp13 | | ct cca1 | P-S | 5719 | 17421 | C | C | C | C | C | C | C | C | C | C | C | C | T | C | C | C |
| | | Phase | | | | | | | | | E | E | E | E | E | E | E | E | | | |
| | | Year | | | | HP04 | HP04 | PC04 | PC04 | PC04 | PC03 | PC03 | HP03 | HP03 | HP03 | HP03 | HP03 | HP03 | HP03 | HP03 | HP03 |

| | | SNV | Codon | AA switch | AA residue # | nt coordinate | GZ03-02 | GZ03-01 | gz1227 | gz1136 | GZL13 | SZ16 | SZ3 | HGZ8L1-A | GZ02 | GD01 | ZS-C | ZS-B | ZS-A | GZ50 | JMD | HSZ-A | HSZ-Bb |
|---|---|---|---|---|---|---|---|---|---|---|---|---|---|---|---|---|---|---|---|---|---|---|---|
| | | | | | | Year | HP04 | HP04 | PC04 | PC04 | PC04 | PC03 | PC03 | HP03 | HP03 | HP03 | HP03 | HP03 | HP03 | HP03 | HP03 | HP03 | HP03 |
| | | | | | | Phase | E | E | E | E | E | E | E | E | E | E | E | E | E | E | E | E | E |
| Sars3a | Sars3b | gt tcg3 | S-S | | 26129 | G | G | G | G | G | G | G | G | G | G | G | G | G | G | G | G | G |
| | | ac cca3 | P-P | 121 | 26050 | A | A | A | A | A | A | A | A | A | A | A | A | A | A | A | A | |
| | | at gct3 | A-A | 115 | 26032 | T | T | T | T | T | T | A | A | A | A | A | A | T | T | T | A | |
| | | ta agg1 | W-R | 52 | 25844 | A | A | A | A | A | A | A | A | T | T | T | T | A | A | A | A | |
| | | ac aaa1 | K-Q | 40 | 25808 | A | A | A | A | A | A | A | A | C | C | C | C | A | A | A | A | |
| | | ca gaa2 | A-E | 31 | 25779 | A | A | A | A | A | A | A | A | C | C | C | C | C | A | A | A | |
| | | ta gat3 | D-E | 2 | 25693 | A | A | A | A | A | T | T | T | T | T | T | T | T | T | T | T | |
| | | tg tgt1 | C-G | 121 | 25628 | G | G | G | G | G | G | G | T | T | T | T | T | T | T | T | T | |
| | | ga ggt2 | G-D | 100 | 25566 | G | G | G | G | G | G | G | G | A | A | A | G | G | G | G | G | |
| | | ct cat1 | H-Y | 93 | 25544 | C | C | C | C | C | C | T | T | C | C | C | C | C | C | C | C | |
| | | ta ctg2 | L-Q | 85 | 25521 | T | T | T | T | T | T | T | T | T | T | T | T | T | A | T | T | |
| | | ta tgc1 | C-S | 81 | 25508 | A | A | A | A | A | A | A | T | T | T | T | T | T | T | T | T | |
| | | ag cat2 | H-R | 30 | 25356 | G | G | G | G | G | A | A | A | A | A | A | A | A | A | A | A | |
| | | ca cct2 | P-H | 25 | 25341 | A | A | A | A | A | A | C | C | C | C | C | C | C | C | C | C | |
| | | ga aga2 | R-K | 11 | 25299 | G | G | G | G | G | G | G | G | G | G | G | G | G | G | G | G | |
| | | ta ttt1 | L-F | 7 | 25286 | A | A | A | A | A | A | T | T | T | T | T | T | T | T | T | T | |
| S | | ct ctc1 | L-F | 1247 | 25230 | C | C | C | C | C | C | C | C | C | C | C | C | C | C | C | C | |
| | | ct gcc2 | A-V | 1208 | 25114 | C | C | C | C | C | C | C | C | C | C | C | C | C | C | C | C | |
| | | tc att3 | I-I | 1180 | 25031 | C | C | C | C | T | T | T | T | T | T | T | T | T | T | T | T | |
| | | ga aaa1 | E-K | 1163 | 24978 | G | G | G | G | G | G | A | G | A | A | A | A | A | A | G | G | |
| | | ct ctt1 | D-D | 1148 | 24933 | C | C | C | C | C | C | C | C | C | C | C | C | C | C | C | C | |
| | | ct tgt3 | C-C | 1025 | 24566 | C | C | C | C | C | C | C | C | C | C | C | C | C | T | T | T | |
| | | gt agg2 | R-M | 1001 | 24493 | G | G | G | G | G | G | G | G | G | G | G | G | G | G | G | G | |
| | | gt tcg3 | S-S | 964 | 24383 | G | T | G | G | T | G | G | G | G | G | G | G | G | G | G | G | |
| | | ag acc1 | T-A | 894 | 24171 | A | A | A | A | G | G | A | A | A | A | A | A | A | A | A | A | |
| | | gt tat1 | D-Y | 778 | 23823 | G | G | G | G | G | G | G | G | G | G | G | G | G | G | N | G | |
| | | ct gct2 | A-V | 765 | 23785 | T | T | T | T | T | C | C | C | C | C | C | C | C | C | N | C | |
| | | ct gct2 | A-V | 754 | 23752 | C | C | C | C | C | T | T | C | C | C | C | C | C | C | N | C | |
| | | ag gca3 | A-A | 748 | 23735 | A | A | A | A | A | A | T | A | A | A | A | A | A | A | N | A | |
| | | cg aca2 | T-R | 743 | 23719 | G | G | G | G | G | C | C | C | C | C | C | C | C | C | N | C | |
| | | ag aca1 | T-A | 743 | 23718 | A | A | A | A | A | G | T | G | A | A | A | A | A | A | N | A | |
| | | ct tca2 | S-L | 701 | 23593 | C | C | C | C | C | T | T | C | C | C | C | C | C | C | N | C | |
| | | tc tta2 | L-S | 665 | 23485 | C | C | C | C | C | C | C | T | T | T | T | T | T | T | T | T | |
| | | ta gat3 | D-E | 613 | 23330 | C | T | A | A | A | T | T | T | T | T | T | T | T | T | T | T | |
| | | ct gca2 | A-V | 609 | 23317 | G | T | T | T | T | C | C | C | C | C | C | C | C | C | C | C | |
| | | gt gca1 | A-S | 609 | 23316 | G | T | T | T | T | G | G | G | G | G | G | G | G | G | G | G | |
| | | tc tct1 | S-P | 607 | 23310 | T | T | T | T | T | C | C | T | T | T | T | T | T | T | T | T | |
| | | tc gtt3 | V-V | 596 | 23279 | T | T | T | T | T | T | T | T | T | T | T | T | T | T | T | T | |
| | | tg tct1 | S-A | 577 | 23220 | T | T | T | T | T | T | T | T | T | T | T | T | T | T | T | T | |
| | | ct tcc3 | S-S | 561 | 23174 | C | C | C | C | C | C | C | C | C | C | C | C | C | C | C | C | |
| | | cg act2 | T-S | 487 | 22951 | G | G | G | G | A | G | C | C | C | C | C | C | C | C | C | C | |
| | | ag gat2 | D-G | 480 | 22930 | G | G | G | G | A | G | A | A | A | A | A | A | A | A | A | A | |

FIG. 1D-2

| | | | | | | GZ03-02 | GZ03-01 | gz1227 | gz1136 | GZL13 | SZ16 | SZ3 | HGZ8L1-A | GZ02 | GD01 | ZS-C | ZS-B | ZS-A | GZ50 | JMD | HSZ-A |
|---|---|---|---|---|---|---|---|---|---|---|---|---|---|---|---|---|---|---|---|---|---|
| | | gc | | | 29725 | G | G | G | G | G | - | C | G | G | G | G | G | G | G | N | G |
| N | Sars9b | ag aag3 | K-K | 376 | 29247 | G | G | G | G | G | G | A | A | G | A | A | G | G | A | N | |
| | | ga gac1 | D-N | 372 | 29233 | A | G | G | G | G | A | A | G | G | G | G | G | G | G | N | |
| | | ac aag2 | K-T | 371 | 29231 | A | A | A | C | C | A | A | A | A | A | A | A | A | A | N | |
| | | tg cat3 | H-Q | 301 | 29022 | G | G | G | G | G | T | T | T | T | T | T | T | T | T | N | |
| | | ct act2 | T-I | 297 | 29009 | T | T | C | C | C | C | C | C | C | C | C | C | C | C | N | |
| | | ag aga3 | R-R | 277 | 28950 | G | G | G | A | A | A | A | A | A | A | A | A | A | A | N | |
| | | ct act2 | T-I | 50 | 28268 | C | C | C | C | C | C | C | C | C | C | C | C | C | C | C | |
| | | tc aat3 | N-N | 27 | 28200 | T | C | C | C | C | T | T | T | T | T | T | T | T | T | | |
| | | ct act2 | T-I | 25 | 28193 | C | C | C | C | C | C | C | C | C | C | T | T | T | C | C | C |
| Sars8b | | ac aat1 | N-H | 80 | 28101 | A | C | A | A | A | A | C | A | A | A | A | A | A | A | N | A |
| | | tc ctt1 | F-L | 76 | 28089 | C | C | C | C | C | C | C | C | T | T | C | C | C | C | N | C |
| | | ct caa1 | Q-* | 49 | 28008 | C | C | C | C | C | C | C | C | C | C | C | C | C | C | N | C |
| Sars8a | | ca cac1 | H-N | 39 | 27893 | A | A | A | A | A | C | C | C | C | C | C | - | C | - | N | C |
| | | ct ctt1 | L-F | 31 | 27869 | T | T | C | C | C | C | C | C | C | C | C | - | C | - | N | C |
| | | ct tgc1 | R-C | 17 | 27827 | C | C | C | C | C | C | C | C | C | C | C | C | C | C | C | C |
| | | ct cta1 | S-F | 11 | 27812 | C | C | C | C | C | C | C | C | C | C | C | C | C | C | C | C |
| Sars7a | | ct gac3 | D-D | 51 | 27425 | T | T | T | T | T | C | C | C | C | C | C | C | C | C | C | C |
| | | ag gga3 | G-G | 38 | 27386 | A | G | G | G | G | A | A | A | A | A | A | A | A | A | A | A |
| | | ag tca3 | S-S | 37 | 27383 | A | A | G | G | G | A | A | A | A | A | A | A | A | A | A | A |
| Sars6 | | ct cct2 | P-L | 57 | 27243 | C | C | C | C | C | C | C | C | T | C | C | C | C | C | C | C |
| | | ag aga1 | R-G | 38 | 27185 | A | A | G | G | G | A | A | A | A | A | A | A | A | A | A | A |
| | | ct gac3 | D-D | 6 | 27091 | C | C | C | C | C | C | C | C | C | C | C | C | C | C | C | C |
| M | | ag att1 | I-V | 86 | 26653 | A | A | A | A | A | A | A | A | A | A | A | A | A | A | A | A |
| | | ct gct2 | A-V | 68 | 26600 | C | C | C | C | C | C | C | C | C | C | C | C | C | C | C | C |
| | | ct tgt3 | C-C | 63 | 26586 | T | C | C | C | C | C | C | C | C | T | C | C | T | C | C | T |
| | | tc tat1 | Y-H | 38 | 26509 | T | T | T | T | T | T | T | T | T | T | T | T | T | T | T | T |
| | | tg ttc2 | F-C | 27 | 26477 | T | T | T | T | T | T | T | T | T | T | T | T | T | T | T | T |
| | | ag aaa3 | K-K | 13 | 26436 | G | G | G | G | G | A | A | A | A | A | A | A | A | A | A | A |
| | | ga ggt1 | G-S | 5 | 26410 | A | A | A | A | A | A | A | G | G | A | G | G | A | G | G | A |
| E | | at aat1 | N-Y | 45 | 26249 | A | A | A | A | A | A | A | A | A | A | A | A | A | A | A | A |
| | | ct aca2 | T-I | 30 | 26205 | C | C | C | C | C | C | C | C | C | C | C | C | C | C | C | C |
| | | ct - | V-V | 29 | 26203 | C | C | C | C | C | C | C | C | C | C | C | C | C | C | C | C |
| | | | | | Phase | | | | | | | | E | E | E | E | E | E | E | E | E |
| | | | | | Year | HP04 | HP04 | PC04 | PC04 | PC04 | PC03 | PC03 | HP03 | HP03 | HP03 | HP03 | HP03 | HP03 | HP03 | HP03 | HP03 |
| | | SNV | Codon | AA switch | AA residue # | nt coordinate | | | | | | | | | | | | | | | |

| Orf1ab | | SNV | Codon | AA switch | AA residue # | nt coordinate | TW8 | TWH | TW7 | TW6 | TW11 | TW10 | GD69 | HSR | TWC | SIN2748 | SIN2677 | SIN2500 | PUMC03 | Sino1-11 | PUMC02 | Sino3-11 |
|---|---|---|---|---|---|---|---|---|---|---|---|---|---|---|---|---|---|---|---|---|---|---|
| Orf1ab | nsp12 | ct ccc3 | P-P | 5709 | 17390 | | C | C | C | C | C | C | C | C | C | C | C | C | C | C | C | C |
| Orf1ab | nsp12 | ct gct2 | A-V | 5704 | 17374 | | C | C | C | C | C | C | C | C | C | C | C | C | C | C | C | C |
| Orf1ab | nsp12 | ct tta2 | S-L | 5623 | 17131 | | T | T | T | T | T | T | T | T | T | T | T | T | T | T | T | T |
| Orf1ab | nsp12 | ct cca1 | P-S | 5542 | 16890 | | C | C | C | C | C | C | C | C | C | C | C | T | T | C | C | C |
| Orf1ab | nsp12 | tg act3 | T-T | 5426 | 16541 | | T | T | T | T | T | T | T | T | T | T | T | T | T | T | T | T |
| Orf1ab | nsp12 | ag cca3 | P-P | 5354 | 16325 | | A | A | A | A | A | A | A | A | A | G | A | A | A | A | A | A |
| Orf1ab | nsp12 | ct tac3 | Y-Y | 4848 | 14807 | | C | C | C | C | C | C | C | C | C | C | C | C | C | C | C | C |
| Orf1ab | nsp12 | tc tgt3 | C-C | 4679 | 14300 | | T | T | T | T | T | T | T | T | T | T | T | T | T | T | T | T |
| Orf1ab | nsp12 | ct ctc1 | L-F | 4629 | 14151 | | C | C | C | C | C | C | C | C | C | C | C | C | C | C | C | C |
| Orf1ab | nsp12 | ga agg3 | R-R | 4618 | 14117 | | G | G | G | G | G | G | G | G | G | G | G | G | G | G | G | G |
| Orf1ab | nsp12 | ct gac3 | D-D | 4533 | 13862 | | C | C | C | C | C | C | C | C | C | C | C | C | C | C | C | C |
| Orf1ab | nsp12 | tg gct3 | A-A | 4499 | 13760 | | T | T | T | T | T | T | T | T | T | T | T | T | T | T | T | T |
| Orf1ab | nsp10 | ct gac3 | D-D | 4361 | 13347 | | C | C | C | C | C | C | T | C | C | C | C | C | C | C | C | C |
| Orf1ab | nsp9 | ga gga2 | G-E | 4154 | 12725 | | G | G | G | G | G | G | G | G | G | G | G | G | G | G | G | G |
| Orf1ab | nsp8 | tc gtc2 | V-A | 3952 | 12119 | | T | T | T | T | T | T | T | T | T | T | T | T | T | T | T | T |
| Orf1ab | nsp7 | ag aag2 | K-R | 3843 | 11792 | | A | A | A | A | A | A | A | A | A | A | A | A | A | A | A | A |
| Orf1ab | nsp6 | ac aac2 | N-T | 3818 | 11717 | | A | A | A | A | A | A | A | A | A | A | A | A | A | A | A | A |
| Orf1ab | nsp6 | ct ggc3 | G-G | 3750 | 11514 | | C | C | C | C | C | C | C | C | C | C | C | C | C | C | C | C |
| Orf1ab | nsp6 | ct tac3 | Y-Y | 3743 | 11493 | | T | T | T | T | T | T | C | C | C | C | C | C | C | C | C | C |
| Orf1ab | nsp6 | ct atc3 | I-I | 3728 | 11448 | | C | C | C | C | C | C | C | C | C | C | C | C | C | C | C | C |
| Orf1ab | nsp6 | ta ctt3 | L-L | 3571 | 10977 | | T | T | T | T | T | T | T | T | T | T | T | T | T | T | T | T |
| Orf1ab | nsp5 | ca gac3 | D-E | 3488 | 10728 | | C | C | C | C | C | C | C | C | C | C | C | C | C | C | C | C |
| Orf1ab | nsp5 | ac aca3 | T-T | 3441 | 10587 | | A | A | A | A | A | A | A | A | A | A | A | A | A | A | A | A |
| Orf1ab | nsp5 | ag ggg3 | G-G | 3255 | 10029 | | G | G | G | G | G | G | G | G | G | G | G | G | G | G | G | A |
| Orf1ab | nsp4 | ct gcc2 | A-V | 3197 | 9854 | | C | C | C | C | C | C | C | C | C | C | C | C | C | C | C | C |
| Orf1ab | nsp4 | ct gta2 | A-V | 3072 | 9479 | | T | T | T | T | T | T | T | T | T | T | T | T | T | T | T | T |
| Orf1ab | nsp4 | tg ttt1 | F-V | 3062 | 9448 | | T | T | T | T | T | T | T | T | T | T | T | T | T | T | T | T |
| Orf1ab | nsp4 | ct gtt2 | A-V | 3047 | 9404 | | T | T | T | T | T | T | T | T | T | T | T | T | T | T | T | T |
| Orf1ab | nsp4 | tc gta2 | V-A | 3024 | 9335 | | T | T | T | T | T | T | T | T | T | T | T | T | T | T | T | T |
| Orf1ab | nsp4 | ct gta2 | A-V | 2971 | 9176 | | T | T | T | T | T | T | T | T | T | T | T | T | T | T | T | T |
| Orf1ab | nsp4 | ct tct2 | S-F | 2949 | 9110 | | C | C | C | C | C | C | C | C | C | C | C | C | C | C | C | C |
| Orf1ab | nsp4 | tc act2 | I-T | 2944 | 9095 | | C | C | C | C | C | C | C | C | C | C | C | C | C | C | C | C |
| Orf1ab | nsp4 | at gct3 | A-A | 2894 | 8946 | | T | T | T | T | T | T | T | T | T | T | T | T | T | T | T | T |
| Orf1ab | nsp4 | tc ctg1 | L-L | 2851 | 8815 | | C | C | C | C | C | C | C | C | C | C | C | C | C | C | C | C |
| Orf1ab | nsp4 | gt gta1 | V-L | 2770 | 8572 | | G | G | G | G | G | G | G | G | G | G | G | G | G | G | G | G |
| Orf1ab | nsp4 | ct tat3 | Y-Y | 2765 | 8559 | | T | T | T | T | T | T | T | T | T | T | T | T | T | T | T | T |
| Orf1ab | nsp4 | gt tgt3 | W-C | 2746 | 8502 | | T | T | T | T | T | T | T | T | T | T | T | T | T | T | T | T |
| Orf1ab | | ta ctt3 | L-L | 2589 | 8031 | | T | T | T | T | T | T | T | T | T | T | T | T | T | T | T | T |
| Orf1ab | | ct gct2 | A-V | 2552 | 7919 | | C | C | C | C | C | C | C | C | C | C | C | C | C | C | C | C |
| Orf1ab | | tc agt3 | S-S | 2539 | 7881 | | T | T | T | T | T | T | T | T | T | T | T | T | T | T | T | T |
| Orf1ab | | ct tac3 | Y-Y | 2537 | 7875 | | C | C | C | C | C | C | C | C | C | C | C | C | C | C | C | C |
| Orf1ab | | ct tgc3 | C-C | 2526 | 7842 | | C | C | C | C | C | C | C | C | C | C | C | C | C | C | C | C |
| | | | | | | HP03 | HP03 | HP03 | HP03 | HP03 | HP03 | HP03 | HP03 | HP03 | HP03 | HP03 | HP03 | HP03 | | | | |

| Region | SNV | Codon | AA switch | AA residue # | nt coordinate | TW8 | TWH | TW7 | TW6 | TW11 | TW10 | GD69 | HSR | TWC | SIN2748 | SIN2677 | SIN2500 | PUMC03 | Sino1-11 | PUMC02 | Sino3-11 |
|---|---|---|---|---|---|---|---|---|---|---|---|---|---|---|---|---|---|---|---|---|---|
| | ta | aat3 | N-K | 479 | 22928 | T | T | T | T | T | T | T | T | T | T | T | T | T | T | T | T |
| | ag | aat2 | N-S | 479 | 22927 | A | A | A | A | A | A | A | A | A | A | A | A | A | A | A | A |
| | tc | ctt2 | L-P | 472 | 22906 | T | T | T | T | T | T | T | T | T | T | T | T | T | T | T | T |
| | ct | tcc3 | S-S | 461 | 22874 | C | C | C | C | C | C | C | C | C | C | C | C | C | C | C | C |
| | tc | ttt2 | F-S | 360 | 22570 | T | T | T | T | T | T | T | T | T | T | T | T | T | T | T | T |
| | ct | tct2 | S-F | 353 | 22549 | C | C | C | C | C | C | C | C | C | C | C | C | C | C | C | C |
| | ga | aaa2 | R-K | 344 | 22522 | A | A | A | A | A | A | A | A | A | A | A | A | A | A | A | A |
| | ga | aga3 | R-R | 342 | 22517 | A | A | A | A | A | A | A | A | A | A | A | A | A | A | A | A |
| | ag | gga1 | R-G | 311 | 22422 | G | G | G | G | G | G | G | G | G | G | G | G | G | G | G | G |
| | ca | aca2 | T-K | 261 | 22273 | C | C | C | C | C | C | C | C | C | C | C | C | C | C | C | C |
| | ct | att2 | T-I | 244 | 22222 | T | T | T | T | T | T | T | T | T | T | T | T | T | T | T | T |
| | tc | tca2 | L-S | 239 | 22207 | C | C | C | C | C | C | C | C | C | C | C | C | C | C | C | C |
| | ca | aac3 | N-K | 227 | 22172 | C | C | C | C | C | C | C | C | C | C | C | C | C | C | C | C |
| | ct | cct3 | P-P | 218 | 22145 | T | T | T | T | T | T | T | T | T | T | T | T | T | T | T | T |
| | ag | cag2 | Q-R | 147 | 21931 | A | A | A | A | A | A | A | A | A | A | A | A | A | A | A | A |
| | ct | gct2 | A-V | 139 | 21907 | C | C | C | C | C | C | C | C | C | C | C | C | C | C | C | C |
| | ga | ggc2 | G-D | 77 | 21721 | G | G | G | G | G | G | G | G | G | G | G | G | G | G | G | G |
| | cg | acg2 | T-R | 75 | 21715 | C | C | C | C | C | C | C | C | C | C | C | C | C | C | C | C |
| | ac | cca3 | P-P | 61 | 21674 | A | A | A | A | A | A | A | A | A | A | A | A | A | A | A | A |
| | ct | tca2 | S-L | 49 | 21637 | C | C | C | C | C | C | C | C | C | C | C | C | C | C | C | C |
| | tg | gct3 | A-A | 27 | 21572 | T | T | T | T | T | T | T | T | T | T | T | T | T | T | T | T |
| nsp16 | tc | aac3 | N-N | 7072 | 21479 | C | C | C | C | C | C | C | C | C | C | C | C | C | C | C | C |
| nsp16 | ac | aaa1 | K-Q | 7023 | 21333 | A | A | A | A | A | A | A | A | A | A | A | A | A | A | A | A |
| nsp16 | ac | gaa3 | E-D | 6992 | 21239 | A | A | A | A | A | A | A | A | A | A | A | A | A | A | A | A |
| nsp16 | ag | agg2 | K-R | 6910 | 20992 | G | G | G | G | G | G | G | G | G | G | G | G | G | G | G | G |
| nsp16 | ag | gat3 | D-D | 6874 | 20885 | T | T | T | T | T | T | T | T | T | T | T | T | T | T | T | T |
| nsp16 | ac | caa2 | Q-P | 6862 | 20848 | A | A | A | A | A | A | A | A | A | A | A | A | A | A | A | A |
| nsp16 | ag | gtg3 | V-V | 6859 | 20840 | G | G | G | G | G | G | G | G | G | G | G | G | G | G | G | G |
| nsp16 | tc | aat3 | N-N | 6804 | 20675 | T | T | T | T | T | T | T | T | T | T | T | T | T | T | T | T |
| nsp15 | tc | cct2 | P-L | 6540 | 19882 | C | C | C | C | C | C | C | C | C | C | C | C | C | C | C | C |
| nsp15 | ag | gta3 | V-V | 6525 | 19838 | A | A | A | A | A | A | A | A | A | A | A | A | A | A | A | A |
| | ct | cta1 | L-L | 6409 | 19491 | C | C | C | C | C | C | C | C | C | C | C | C | C | C | C | C |
| | ag | tta3 | L-L | 6381 | 19406 | A | A | A | A | A | A | A | A | A | A | A | A | A | A | A | A |
| nsp14 | ct | aca2 | T-I | 6274 | 19084 | A | C | C | C | C | C | C | C | C | C | T | T | T | T | C | C |
| nsp14 | ag | gaa3 | E-E | 6267 | 19064 | A | A | A | A | A | A | A | A | A | A | A | A | A | A | A | A |
| nsp14 | ta | att3 | I-I | 6234 | 18965 | T | T | T | T | T | T | T | T | T | T | T | T | T | T | T | T |
| nsp14 | ac | aat1 | N-H | 5972 | 18180 | A | A | A | A | A | A | A | A | A | A | A | A | A | A | A | A |
| nsp14 | ct | cgc3 | R-R | 5861 | 17846 | C | C | C | C | C | C | C | C | C | C | C | C | C | C | C | C |
| nsp14 | ct | aac3 | N-N | 5820 | 17723 | C | C | C | C | C | C | C | C | C | C | C | C | C | C | C | C |
| nsp13 | gt | gat3 | E-D | 5767 | 17564 | T | T | T | T | T | T | T | T | T | T | T | T | T | T | T | T |
| nsp13 | ct | cca1 | P-S | 5719 | 17421 | C | C | C | C | C | C | C | C | C | C | C | C | C | C | C | C |

FIG. 1H-2

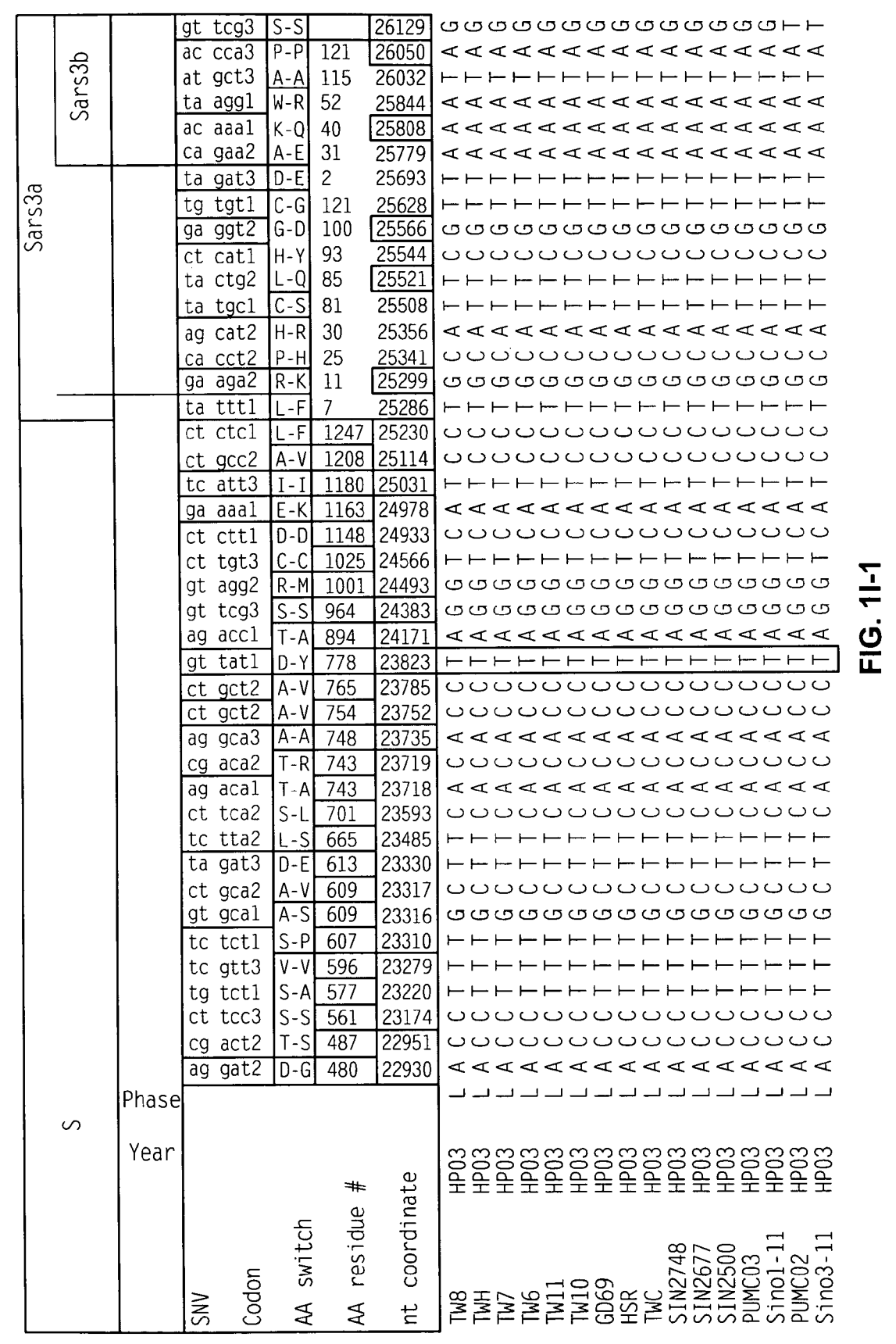

| | | SNV | Codon | AA switch | AA residue # | nt coordinate | TW8 | TWH | TW7 | TW6 | TW11 | TW10 | GD69 | HSR | TWC | SIN2748 | SIN2677 | SIN2500 | PUMC03 | Sino1-11 | PUMC02 | Sino3-11 |
|---|---|---|---|---|---|---|---|---|---|---|---|---|---|---|---|---|---|---|---|---|---|---|
| | Sars3b | gt tcg3 | S-S | | 26129 | G | G | G | G | G | G | G | G | G | G | G | G | G | G

FIG. 1I-2

| | | SNV | Codon | AA switch | AA residue # | nt coordinate | TW8 | TWH | TW7 | TW6 | TW11 | TW10 | GD69 | HSR | TWC | SIN2748 | SIN2677 | SIN2500 | PUMC03 | Sino1-11 | PUMC02 | Sino3-11 |
|---|---|---|---|---|---|---|---|---|---|---|---|---|---|---|---|---|---|---|---|---|---|---|
| | | gc | | | | 29725 | G | G | G | G | G | G | G | G | G | G | G | G | G | G | G | G |
| N | Sars9b | ag aag3 | K-K | 376 | 29247 | G | G | G | G | G | G | G | G | G | G | G | G | G | G | G | G |
| | | ga gac1 | D-N | 372 | 29233 | G | G | G | G | G | G | G | G | G | G | G | G | G | G | G | G |
| | | ac aag2 | K-T | 371 | 29231 | A | A | A | A | A | A | A | A | A | A | A | A | A | A | A | A |
| | | tg cat3 | H-Q | 301 | 29022 | T | T | T | T | T | T | T | T | T | T | T | T | T | T | T | T |
| | | ct act2 | T-I | 297 | 29009 | C | C | C | C | C | C | C | C | C | C | C | C | C | C | C | C |
| | | ag aga3 | R-R | 277 | 28950 | A | A | A | A | A | A | A | A | A | A | A | A | A | A | A | A |
| | | ct act2 | T-I | 50 | 28268 | C | C | C | C | C | C | C | C | C | C | C | C | C | C | C | C |
| | | tc aat3 | N-N | 27 | 28200 | T | T | T | T | T | T | T | T | T | T | T | T | T | T | T | T |
| | | ct act2 | T-I | 25 | 28193 | C | C | C | C | C | C | C | C | C | C | C | C | C | C | C | C |
| | Sars8b | ac aat1 | N-H | 80 | 28101 | A | A | A | A | A | A | A | A | A | A | A | A | A | A | A | A |
| | | tc ctt1 | F-L | 76 | 28089 | C | C | C | C | C | C | C | C | C | C | C | C | C | C | C | C |
| | | ct caa1 | Q-* | 49 | 28008 | C | C | C | C | C | C | C | C | C | C | C | C | C | C | C | C |
| | Sars8a | ca cac1 | H-N | 39 | 27893 | C | C | C | C | C | C | C | C | C | C | C | C | C | C | C | C |
| | | ct ctt1 | L-F | 31 | 27869 | C | C | C | C | C | C | C | C | C | C | C | C | C | C | C | C |
| | | ct tgc1 | R-C | 17 | 27827 | T | T | T | T | T | T | T | T | T | T | T | T | T | T | T | T |
| | | ct cta1 | S-F | 11 | 27812 | C | C | C | C | T | T | C | C | - | - | C | C | C | C | C | C |
| | Sars7a | ct gac3 | D-D | 51 | 27425 | C | C | C | C | C | C | C | C | C | C | C | C | C | C | C | C |
| | | ag gga3 | G-G | 38 | 27386 | A | A | A | A | A | A | A | A | A | A | A | A | A | A | A | A |
| | | ag tca3 | S-S | 37 | 27383 | A | A | A | A | A | A | A | A | A | A | A | A | A | A | A | A |
| | Sars6 | ct cct2 | P-L | 57 | 27243 | C | C | C | C | C | C | C | C | C | C | C | C | C | C | C | C |
| | | ag aga1 | R-G | 38 | 27185 | A | A | A | A | A | A | A | A | A | A | A | A | A | A | A | A |
| | | ct gac3 | D-D | 6 | 27091 | C | C | C | C | C | C | C | C | C | C | C | C | C | C | C | C |
| M | | ag att1 | I-V | 86 | 26653 | A | A | A | A | A | A | A | A | A | A | A | A | A | A | A | A |
| | | ct gct2 | A-V | 68 | 26600 | C | C | C | C | C | C | C | C | T | C | C | C | C | C | C | C |
| | | ct tgt3 | C-C | 63 | 26586 | T | T | T | T | T | T | T | T | T | T | T | T | T | T | T | T |
| | | tc tat1 | Y-H | 38 | 26509 | T | T | T | T | T | T | T | T | T | T | T | T | T | T | T | T |
| | | tg ttc2 | F-C | 27 | 26477 | G | G | G | G | G | G | G | T | T | T | T | T | G | G | G | G |
| | | ag aaa3 | K-K | 13 | 26436 | A | A | A | A | A | A | A | A | A | A | A | A | A | A | A | A |
| | | ga ggt1 | G-S | 5 | 26410 | G | G | G | G | G | G | G | G | G | G | G | G | G | G | G | G |
| E | | at aat1 | N-Y | 45 | 26249 | A | A | A | A | A | A | A | A | A | A | A | T | T | A | A | A |
| | | ct aca2 | T-I | 30 | 26205 | C | C | C | C | C | C | C | C | C | C | C | C | C | C | C | C |
| | | ct - | V-V | 29 | 26203 | C | C | C | T | T | C | C | C | C | C | C | C | C | C | C | C |
| | Phase | | | | | | L | L | L | L | L | L | L | L | L | L | L | L | L | L | L | L |
| | Year | | | | | | HP03 | HP03 | HP03 | HP03 | HP03 | HP03 | HP03 | HP03 | HP03 | HP03 | HP03 | HP03 | HP03 | HP03 | HP03 | HP03 |

| | | Nucleotide Present in Some Members of Group Below | | | | | | Nucleotide Present in All Members of Group Below | | | | | | Presence of Nucleotide is Characteristic of All Members of Single Group Below | | | | | | | |
|---|---|---|---|---|---|---|---|---|---|---|---|---|---|---|---|---|---|---|---|---|---|
| Position | Nucleotide | HP04 | PC04 | PC03 | HP03-E | HP03-M | HP03-L | HP04 | PC04 | PC03 | HP03-E | HP03-M | HP03-L | HP04 | PC04 | PC03 | HP03-E | HP03-M | HP03-L | EE | E |
| 185 | T | X | | | | | | | | | | | | | | | | | | | |
| 508 | T | | X | | | | | | | | | | | | | | | | | | |
| 548 | C | | | | X | | | | | | | | | | | | | | | | |
| 1180 | T | | | | | X | | X | | | | | | | | | | | | | |
| 1206 | C | | | | X | X | | X | X | | | | | X | | | | | | | |
| 1221 | C | | | | X | | X | | | | | | | | | | | | | | |
| 1302 | G | | X | | | | | | | | | | | | | | | | | | |
| 1441 | C | | | | | | X | | | X | | | | | | | | | | | |
| 1727 | T | | | | | | X | X | | | | | | | | | | | | | |
| 1782 | T | | | | X | | | | | | | | | | | | | | | | |
| 1909 | T | | | | | | X | X | X | X | | | | | | | | | | | |
| 2013 | A | | | | | | | X | X | | | | | | | | | | | | |
| 2557 | A | | | | | | | X | X | | | | | | | | | | | | |
| 2606 | T | | | | | | X | X | X | | | | | | | | | | | | |
| 2759 | T | | | | | | | X | | | | | | | | | | | | | |
| 2760 | T | | | | | | | X | X | | | | | | | | | | | X | |
| 3165 | G | | | | X | | | X | | | | | | | | | | | | X | |
| 3326 | C | | | | | | X | X | X | X | | | | | | | | | | X | |
| 3567 | C | | | | X | | | | | | | | | | | | | | | | |
| 3570 | T | | | | X | | | X | | | | | | | | | | | | X | |
| 3584 | G | | | | X | | | X | X | X | | | | | | | | | | X | |
| 3626 | C | | | | | | | X | X | X | | | | | | X | | | | | |
| 3671 | T | | | | | | X | | | | | | | | | | | | | | |
| 3852 | C | | | | X | | | | | | | | | | | | | | | | |
| 3962 | T | | | | | | | | | | | | | | | | | | | | |
| 4108 | A | | | | | | | X | X | | | | | | | | | | | X | |

FIG. 2B

| Position | Nucleotide | Nucleotide Present in Some Members of Group Below ||||||  Nucleotide Present in All Members of Group Below ||||||  Presence of Nucleotide is Characteristic of All Members of Single Group Below ||||||||
| --- | --- | --- | --- | --- | --- | --- | --- | --- | --- | --- | --- | --- | --- | --- | --- | --- | --- | --- | --- | --- |
| | | HP04 | pC04 | pC03 | HP03-E | HP03-M | HP03-L | HP04 | pC04 | pC03 | HP03-E | HP03-M | HP03-L | HP04 | pC04 | pC03 | HP03-E | HP03-M | HP03-L | EE | E |
| 4160 | C | | | | | | | X | | | | | | X | | | | | | | |
| 4220 | G | | | | | | | | | | | | | | | | | | | X | |
| 5142 | G | | | | | | | X | | | X | | | | | | X | | | | |
| 5199 | G | | | | | | | X | X | | | | | | | | | | | | |
| 5251 | A | | | | | | | X | X | | | | | | | | | | | | |
| 5811 | C | | | | | | | X | | | | | | | | | | | | X | |
| 5963 | T | X | | | | | | | | | | | | | | | | | | | |
| 6148 | A | | | | X | | | X | | | | | | | | | | | | | |
| 6205 | G | | | | | | | X | | X | | | | | | | | | | | |
| 6251 | C | | X | | X | | | X | | X | | | | | | | | | | | |
| 6295 | T | | X | | | | | | | X | | | | | | | | | | | |
| 6456 | G | | | | | X | | | | | | | | | | X | | | | | |
| 6612 | T | | | | | | | X | X | | | | | | | | | | | | |
| 6929 | A | | | | X | | | X | X | X | | | | | | | | | | | |
| 6990 | T | | | | X | | | | | | | | | | | | | | | X | |
| 7070 | C | | | | X | | | X | X | | | | | | | | | | | | |
| 7137 | T | | | | | X | | | | | | | | | | | | | | X | |
| 7842 | T | | | | X | | | | | | | | | | | | | | | | |
| 7875 | T | | | | | | | X | X | X | | | | | | | | | | | |
| 7881 | C | | | | | | | X | X | X | | | | | | | | | | X | |
| 7919 | T | | | | X | | X | | | | | | | | | | | | | | |
| 8031 | A | | | | X | | | | | | | | | | | | | | | | |
| 8502 | G | | | | X | | | | | | | | | | | | | | | | |
| 8559 | C | | | | X | | | | | | | | | | | | | | | | |
| 8572 | T | | | | | X | | | | | | | | | | | | | | | |
| 8815 | T | | | | X | | | | | | | | | | | | | | | | |

FIG. 2C

| Position | Nucleotide | Nucleotide Present in Some Members of Group Below | | | | | | Nucleotide Present in All Members of Group Below | | | | | | Presence of Nucleotide is Characteristic of All Members of Single Group Below | | | | | | | |
|---|---|---|---|---|---|---|---|---|---|---|---|---|---|---|---|---|---|---|---|---|---|
| | | HP04 | pC04 | pC03 | HP03-E | HP03-M | HP03-L | HP04 | pC04 | pC03 | HP03-E | HP03-M | HP03-L | HP04 | pC04 | pC03 | HP03-E | HP03-M | HP03-L | EE | E |
| 8946 | A | | | | X | | | | | | | | | | | | | | | | |
| 9095 | T | | | | X | | | | | | | | | | | | | | | | |
| 9110 | T | | | | X | | | | | | | | | | | | | | | | |
| 9176 | C | X | | | X | | | | | | | | | | | | | | | X | |
| 9335 | C | | | | X | | | X | | | | | | | | | | | | | |
| 9404 | T | | | | X | X | | X | X | | | | | | | | | | | | |
| 9448 | G | | | | X | X | X | | | | | | | | | | | | | | |
| 9479 | C | | | | | X | X | X | | X | | | | | | | | | | | |
| 9854 | T | | | | X | | | | | | | | | | | | | | | | |
| 10029 | A | | | | X | X | | X | X | | | | | | | | | | | | |
| 10587 | C | | | | | X | X | | | | | | | | | | | | | X | |
| 10728 | A | | | | | X | X | | | | | | | | | | | | | | |
| 10977 | A | | | | | | | | | | | | | | | | | | | | |
| 11448 | T | | | | | | | | X | X | | | | | | | | | | | |
| 11493 | T | | | | | | | | | | | | | | | | | | | | |
| 11514 | T | | | | | | X | X | X | | | | | | | | | | | | |
| 11717 | C | | | | | | | | | | | | | | | | | | | X | |
| 11792 | G | | X | | | | | | | | | | | | | | | | | | |
| 12119 | C | | | | | | | X | X | | | | | | | | | | | | |
| 12725 | A | | | | | | | | | | | | | | | | | | | | |
| 13347 | T | | | | X | | | | X | X | | | | | | | | | | X | |
| 13760 | G | | | | | | | | | | | | | | | | | | | | |
| 13862 | T | | | | X | | | X | X | | | | | | | | | | | | |
| 14117 | A | | | | | | | | | | | | | | | | | | | X | |
| 14151 | T | | | | | | | X | X | | | | | | | | | | | X | |
| 14300 | C | | | | | | | X | X | | | | | X | | | | | | X | |

| Position | Nucleotide | Nucleotide Present in Some Members of Group Below | | | | | | Nucleotide Present in All Members of Group Below | | | | | | Presence of Nucleotide is Characteristic of All Members of Single Group Below | | | | | | | |
|---|---|---|---|---|---|---|---|---|---|---|---|---|---|---|---|---|---|---|---|---|---|
| | | HP04 | pC04 | pC03 | HP03-E | HP03-M | HP03-L | HP04 | pC04 | pC03 | HP03-E | HP03-M | HP03-L | HP04 | pC04 | pC03 | HP03-E | HP03-M | HP03-L | EE | E |
| 14807 | T | | | | | | X | | | | | | | | | | | | | | |
| 16325 | G | | | | | | X | | | | | | | | | | | | | | |
| 16541 | G | | | X | | | | | | | | | | | | | | | | | |
| 16890 | T | | | | X | | | | | | | | | | | | | | | | |
| 17131 | C | | | | | | X | | | | | | | | | | | | | | |
| 17374 | T | | | | X | | | | X | | | | | | | | | | | | |
| 17390 | T | | | | | | | | X | | | | | | X | | | | | | |
| 17421 | T | | | | | | X | X | X | | | | | | | | | | | | |
| 17564 | G | | | | X | | X | X | X | X | X | | | | | | | | | | |
| 17723 | T | | | | | | X | | X | | | | | | | | | | | | |
| 17846 | T | | | | | X | X | X | X | | | | | | | | | | | | |
| 18180 | C | X | | | | | | | | | | | | | | | | | | | |
| 18965 | A | | | | | | X | | X | | | | | | | | | | | | |
| 19064 | G | | | | | | X | | | | | | | | | | | | | | |
| 19084 | T | | | | | | X | | | | | | | | | | | | | | |
| 19406 | C | | | | | | | X | X | | | | | | | | | | | | |
| 19491 | G | | X | | | | | | | | | | | | | | | | | | |
| 19838 | T | | | | | X | X | | X | X | | | | | | | | | | | |
| 19882 | G | | | | | | X | | | | | | | | | | | | | | |
| 20675 | T | | | | X | | | | | | | | | | | | | | | | |
| 20840 | C | | | | X | | | | X | X | | | | | | | | | | | |
| 20848 | A | | | | | | | | | X | | | | | | | | | | | |
| 20885 | C | | | | | X | | | | | | | | | | | | | | X | |
| 20992 | A | | | | X | | | | | | | | | X | | | | | | | |
| 21239 | C | | | | | | | | | | | | | | | | | | | | |

| Position | Nucleotide | Nucleotide Present in Some Members of Group Below ||||||  Nucleotide Present in All Members of Group Below ||||||  Presence of Nucleotide is Characteristic of All Members of Single Group Below ||||||||
|---|---|---|---|---|---|---|---|---|---|---|---|---|---|---|---|---|---|---|---|---|---|
|  |  | HP04 | pC04 | pC03 | HP03-E | HP03-M | HP03-L | HP04 | pC04 | pC03 | HP03-E | HP03-M | HP03-L | HP04 | pC04 | pC03 | HP03-E | HP03-M | HP03-L | EE | E |
| 21333 | C |  |  |  |  | X |  |  |  |  |  |  |  |  |  |  |  |  |  |  |  |
| 21479 | T |  |  |  | X |  |  |  |  |  |  |  |  |  |  |  |  |  |  |  |  |
| 21572 | G |  |  |  |  |  | X |  |  |  |  |  |  |  |  |  |  |  |  |  |  |
| 21637 | T |  |  |  | X |  |  |  |  |  |  |  |  |  |  |  |  |  |  |  |  |
| 21674 | C |  |  |  |  | X |  |  |  |  |  |  |  |  |  |  |  |  |  |  |  |
| 21715 | G |  |  |  | X |  |  |  |  |  |  |  |  |  |  |  |  |  |  |  |  |
| 21721 | A |  |  |  |  |  |  | X | X | X |  |  |  |  |  |  |  |  |  | X |  |
| 21907 | T |  |  |  |  |  |  | X | X | X |  |  |  |  |  |  |  |  |  | X |  |
| 21931 | G |  |  |  | X |  |  | X | X |  |  |  |  |  |  |  |  |  |  |  |  |
| 22145 | C |  |  |  |  | X |  | X |  | X |  |  |  |  |  |  |  |  |  |  |  |
| 22172 | A |  |  |  |  |  |  | X |  |  | X |  |  |  |  |  |  |  |  |  |  |
| 22207 | T |  |  |  | X |  |  | X | X | X |  |  |  |  |  |  |  |  |  |  |  |
| 22222 | C |  |  |  |  |  |  | X | X | X |  |  |  |  |  | X |  |  |  |  |  |
| 22273 | A |  |  |  |  |  |  | X | X | X | X | X |  |  |  |  |  |  |  |  |  |
| 22422 | A |  |  |  | X |  |  | X | X | X |  |  |  |  |  | X |  |  |  |  |  |
| 22517 | G |  |  |  | X |  |  | X | X | X |  |  |  |  |  |  |  |  |  |  |  |
| 22522 | G |  |  |  | X |  |  |  |  |  |  |  |  |  |  |  |  |  |  |  |  |
| 22549 | T |  |  |  |  |  | X | X | X |  |  |  |  |  |  |  |  |  |  |  |  |
| 22570 | C |  |  |  |  |  |  |  |  |  |  |  |  |  |  |  |  |  |  | X |  |
| 22874 | T |  |  |  |  |  |  |  |  |  |  |  |  |  |  |  |  |  |  | X |  |
| 22906 | C |  | X |  |  |  |  | X | X | X |  |  |  |  |  |  |  |  |  |  |  |
| 22927 | G |  | X |  |  |  |  | X | X |  |  |  |  |  |  |  |  |  |  |  |  |
| 22928 | A |  |  |  |  |  |  |  |  |  |  |  |  |  |  |  |  |  |  |  |  |
| 22930 | G |  |  |  |  |  |  | X | X |  |  |  |  |  |  |  |  |  |  | X |  |
| 22951 | G |  |  |  |  |  |  | X | X | X |  |  |  |  |  |  |  |  |  |  |  |
| 23174 | T |  |  |  |  |  | X |  |  |  |  |  |  |  |  |  |  |  |  |  |  |

FIG. 2F

| Position | Nucleotide | Some: HP04 | Some: pC04 | Some: pC03 | Some: HP03-E | Some: HP03-M | Some: HP03-L | All: HP04 | All: pC04 | All: pC03 | All: HP03-E | All: HP03-M | All: HP03-L | Char: HP04 | Char: pC04 | Char: pC03 | Char: HP03-E | Char: HP03-M | Char: HP03-L | Char: EE | Char: E |
|---|---|---|---|---|---|---|---|---|---|---|---|---|---|---|---|---|---|---|---|---|---|
| 23220 | G | | | | | | X | | | | | | | | | | | | | | |
| 23279 | C | | | | | | X | | | | | | | | | | | | | | |
| 23310 | C | X | | | | | | | | | | | | | | | | | | | |
| 23316 | T | X | | | | | | | | | | | | | | | | | | | |
| 23317 | T | X | | | | | | | | | | | | | | | | | | | |
| 23330 | A | | | | | | | | X | | | | | | | | | | | | |
| 23485 | C | | | | | | | | X | X | | | | | | | | | | | |
| 23593 | T | | | | | | | | | X | | | | | | X | | | | | |
| 23718 | G | | | | | | | X | X | X | | | | | | X | | | | | |
| 23719 | G | | | | | | X | | | X | | | | | | | | | | X | |
| 23735 | G | | | | | | | X | X | X | | | | | | | | | | | |
| 23752 | T | | | | | | | | | X | | | | | | | | | | | |
| 23785 | T | | | | | | | X | X | X | X | | | | | X | | | | X | |
| 23823 | G | | | | | | | | | | | X | X | | | | | | | | X |
| 23823 | T | | | X | | | | | | X | | | | | | | | | | | |
| 24171 | G | | | | | | | | | X | | | | | | | | | | X | |
| 24383 | T | | X | | | | | | | | | | | | | | | | | | |
| 24493 | C | | | | | | | | X | | | | | | | | | | | | |
| 24566 | T | | | | | | | | X | X | | | | | | | | | | | |
| 24933 | T | | | | X | X | | | | X | | | | | | | | | | | |
| 24978 | G | | | | | | | X | X | | | | X | | | | | | | | |
| 25031 | C | | | | | | X | X | X | X | | X | | | | | | | | | |
| 25114 | T | | | | X | | | X | X | | | | | | | | | | | | |
| 25230 | T | | | | | | | | | | | | | | | | | | | X | |
| 25286 | A | | | | | X | | X | | | | | | | | | | | | | |
| 25299 | A | | | | | | | | | X | | | | | | | | | | | |

FIG. 2G

| Position | Nucleotide | Nucleotide Present in Some Members of Group Below ||||||  Nucleotide Present in All Members of Group Below |||||| Presence of Nucleotide is Characteristic of All Members of Single Group Below ||||||||
|---|---|---|---|---|---|---|---|---|---|---|---|---|---|---|---|---|---|---|---|---|
| | | HP04 | pC04 | pC03 | HP03-E | HP03-M | HP03-L | HP04 | pC04 | pC03 | HP03-E | HP03-M | HP03-L | HP04 | pC04 | pC03 | HP03-E | HP03-M | HP03-L | EE | E |
| 25341 | A | | | | | | | X | X | | | | | | | | | | | X | |
| 25356 | G | | | | | | | X | X | | | | | | | | | | | X | |
| 25508 | A | | | | | | | X | X | X | | | | | | | | | | | |
| 25521 | A | | | | | | | | | | | | | | | | | | | | |
| 25544 | T | | | | X | | | | | | | | | | | | | | | | |
| 25566 | A | | | | | | | X | X | X | | | | | | X | | | | | |
| 25628 | G | | | | | | | X | X | | | | | | | | | | | X | |
| 25693 | A | | | | | | | X | X | X | | | | | | | | | | | |
| 25779 | C | | | | X | | | | | | | | | | | | | | | | |
| 25808 | C | | | | X | | | | | | | | | | | | | | | | |
| 25844 | T | | | | X | | | | | | | | | | | | | | | | |
| 26032 | A | | | | X | | | | | | | | | | | | | | | | |
| 26050 | C | | | | | | X | | | | | | | | | | | | | | |
| 26129 | T | | | | | X | X | | | | | | | | | | | | | | |
| 26203 | T | | | | | | X | | | | | | | | | | | | | | |
| 26205 | T | | | | | | X | | | | | | | | | | | | | | |
| 26249 | T | | | | | | | | | | | | | | | | | | | | |
| 26410 | A | | | | | | | X | X | X | | | | | | | | | | | |
| 26436 | G | | | | | | X | | | | | | | | | | | | | | |
| 26477 | G | | | | X | | X | | | | | | | | | | | | | | |
| 26509 | C | | | | | | | X | X | X | | | | | | | | | | X | |
| 26586 | C | | | | | | | X | | X | | | | | | | | | | | |
| 26600 | T | | | | | | X | | | | | | | | | | | | | | |
| 26653 | C | | | | | | X | | | | | | | | | | | | | | |
| 27091 | T | | | | | | X | | | | | | | | | | | | | | |
| 27185 | G | | X | | | | | | | | | | | | | | | | | | |

FIG. 2H

| Position | Nucleotide | Nucleotide Present in Some Members of Group Below ||||||  Nucleotide Present in All Members of Group Below |||||| Presence of Nucleotide is Characteristic of All Members of Single Group Below ||||||||
|---|---|---|---|---|---|---|---|---|---|---|---|---|---|---|---|---|---|---|---|---|---|
| | | HP04 | pC04 | pC03 | HP03-E | HP03-M | HP03-L | HP04 | pC04 | pC03 | HP03-E | HP03-M | HP03-L | HP04 | pC04 | pC03 | HP03-E | HP03-M | HP03-L | EE | E |
| 27243 | T | | | | X | X | | | | | | | | | | | | | | | |
| 27383 | G | X | X | | | | | | | | | | | | | | | | | | |
| 27386 | G | X | | | | | | | | | | | | | | | | | | | |
| 27425 | T | | | | | | | | X | | | | | | | | | | | X | |
| 27812 | T | | | | | | | X | X | | | | | | | | | | | | |
| 27827 | C | | | | | | | X | X | X | X | X | | | | | | | | | |
| 27827 | T | | | | | | X | X | X | | | | X | | | | | | | X | |
| 27869 | T | X | | | | | | X | X | | | | | | | | | | | | |
| 27893 | A | | | | | | | X | X | | | | | | | | | | | | |
| 27869 | T | | | | | | X | | | | | | | | | | X | | | | |
| 28008 | T | X | | | X | | | | X | | | | | | | | | | | | |
| 28089 | T | X | | | X | | | | X | | | | | | | | | | | | |
| 28101 | C | | | | | | X | | | | | | | | | | | | | | |
| 28193 | T | | | | | | | | | | | | | | | | | | | | |
| 28200 | C | | | | | | | | | | | | | | | | | | | | |
| 28268 | T | | | | | | | | | | | | | | | | | | | | |
| 28950 | G | | | | | | | | X | | | | | | | | | | | | |
| 29009 | T | | X | | | | | | X | | | | | | | | | | | | |
| 29022 | G | | X | | | | | | | | | | | | | | | | | | |
| 29231 | C | | X | | | | | | | | | | | | | | | | | | |
| 29233 | A | | X | | | | | | | | | | | | | | | | | | |
| 29247 | A | | | | X | | | | | | | | | | | | | | | | |
| 29725 | C | | | X | X | | | | | | | | | | | | | | | | |

|  | Orf7b | Orf8a | Orf8b | Nucleocapsid Protein |
|---|---|---|---|---|
| GZ02 | 27635:27769 MNELTLIDFYLCFLA FLLFLVLIMLIIFWF SLEIQDLEEPCTKV* | 27776:28144 (Sars8) MKLLIVLTCISLCSCIRTVVQRCASNKPHVLEDPCPT GYQPEWNIRYNTRGNTYSTAWLCALGKVLPFHRWHTM VQTCTPNVTINCQDPAGGALIARCWYLHEGHQTAAFR DVLVVLNKRTN* |  | 28146:29414 Sars9a nucleocapsid protein MSDNGPQSNQRSAPRITFGGPTDSTDNNQNGGRNGARPKQRRPQGLPNNTASWFTALTQHGKEELRFPRGQGVPINTNSGPDDQIGYYR RATRRVRGGDGKMKELSPRWYFYYLGTGPEASLPYGANKEGIVWATEGALNTPKDHIGTRNPNNNAATVLQLPQGTTLPKGFYAEGSR GGSQASSRSSSRSRGNSRNSTPGSSRGNSPARMASGGGETALALLLLDRLNQLESKVSGKGQQQQGQTVTKKSAAEASKKPRQKRTATK QYNVTQAFGRRGPEQTQGNFGDQDLIRQGTDYKHWPQIAQFAPSASAFFGMSRIGMEVTPSGTWLTYHGAIKLDDKDPQFKDNVILLNK HIDAYKTFPPTEPKKDKKKKTDEAQPLPQRQKKQPTVTLLPAADMDDFSRQLQNSMSGASADSTQA* |
| TOR2 29 dels | 27635:27769 MNELTLIDFYLCFLA FLLFLVLIMLIIFWF SLEIQDLEEPCTKV* | 27776..27924 Sars8a unknown (Sars8a) MKLLIVLTCISLCSC ICTVVQRCASNKPHV LEDPCKVQH* | 27861:28144 Sars8b unknown (Sars8b) MCLKILVRYNTRGNTYSTA WLCALGKVLPFHRWHTMVQ TCTPNVTINCQDPAGGALI ARCWYLHEGHQTAAFRDVL VVLNKRTN* | 28146:29414 Sars9a nucleocapsid protein MSDNGPQSNQRSAPRITFGGPTDSTDNNQNGGRNGARPKQRRPQGLPNNTASWFTALTQHGKEELRFPRGQGVPINTNSGPDDQIGYYR RATRRVRGGDGKMKELSPRWYFYYLGTGPEASLPYGANKEGIVWATEGALNTPKDHIGTRNPNNNAATVLQLPQGTTLPKGFYAEGSR GGSQASSRSSSRSRGNSRNSTPGSSRGNSPARMASGGGETALALLLLDRLNQLESKVSGKGQQQQGQTVTKKSAAEASKKPRQKRTATK QYNVTQAFGRRGPEQTQGNFGDQDLIRQGTDYKHWPQIAQFAPSASAFFGMSRIGMEVTPSGTWLTYHGAIKLDDKDPQFKDNVILLNK HIDAYKTFPPTEPKKDKKKKTDEAQPLPQRQKKQPTVTLLPAADMDDFSRQLQNSMSGASADSTQA* |
| HGZ8LI-B 82 dels | 27635:27769 MNELTLIDFYLCFLA FLLFLVLIMLIIFWF SLEIQDLEEPCTKV* | 27776..27963 MKLLIVLTCISLCSC IRTVVQRCASNIALL GFVL* | * | 28146:29414 Sars9a nucleocapsid protein MSDNGPQSNQRSAPRITFGGPTDSTDNNQNGGRNGARPKQRRPQGLPNNTASWFTALTQHGKEELRFPRGQGVPINTNSGPDDQIGYYR RATRRVRGGDGKMKELSPRWYFYYLGTGPEASLPYGANKEGIVWATEGALNTPKDHIGTRNPNNNAATVLQLPQGTTLPKGFYAEGSR GGSQASSRSSSRSRGNSRNSTPGSSRGNSPARMASGGGETALALLLLDRLNQLESKVSGKGQQQQGQTVTKKSAAEASKKPRQKRTATK QYNVTQAFGRRGPEQTQGNFGDQDLIRQGTDYKHWPQIAQFAPSASAFFGMSRIGMEVTPSGTWLTYHGAIKLDDKDPQFKDNVILLNK HIDAYKTFPPTEPKKDKKKKTDEAQPLPQRQKKQPTVTLLPAADMDDFSRQLQNSMSGASADSTQA* |
| CUHK-LC2 415 dels | 27635:27769 MNELTLIDFYLCFLA FLLFLVLIMLIIFWF SLEIQDLEEPCTKV* | * | * | 27635:29414 MNELTLIDFYLCFLAFLLFLVLIMLIINEQIKMSDNGPQSNQRSAPRITFGGPTDSTDNNQNGGRNGARPKQRRPQGLPNNTASWFTAL TQHGKEELRFPRGQGVPINTNSGPDDQIGYYRRATRRVRGGDGKMKELSPRWYFYYLGTGPEASLPYGANKEGIVWATEGALNTPKDH IGTRNPNNNAATVLQLPQGTTLPKGFYAEGSRGGSQASSRSSSRSRGNSRNSTPGSSRGNSPARMASGGGETALALLLLDRLNQLESKV SGKGQQQQGQTVTKKSAAEASKKPRQKRTATKQYNVTQAFGRRGPEQTQGNFGDQDLIRQGTDYKHWPQIAQFAPSASAFFGMSRIGME VTPSGTWLTYHGAIKLDDKDPQFKDNVILLNKHIDAYKTFPPTEPKKDKKKKTDEAQPLPQRQKKQPTVTLLPAADMDDFSRQLQNSMS GASADSTQA* |
| GZ-C, GZ-B 39 dels +29 dels | 27638:27844 MNELTLIDFYLCFLA FLLFLVLIMLIIFWF SLEIQDLEEPCTKVS LCSCICTVVQRCASN KPHVLEDP* | * | * | 28146:29414 Sars9a nucleocapsid protein MSDNGPQSNQRSAPRITFGGPTDSTDNNQNGGRNGARPKQRRPQGLPNNTASWFTALTQHGKEELRFPRGQGVPINTNSGPDDQIGYYR RATRRVRGGDGKMKELSPRWYFYYLGTGPEASLPYGANKEGIVWATEGALNTPKDHIGTRNPNNNAATVLQLPQGTTLPKGFYAEGSR GGSQASSRSSSRSRGNSRNSTPGSSRGNSPARMASGGGETALALLLLDRLNQLESKVSGKGQQQQGQTVTKKSAAEASKKPRQKRTATK QYNVTQAFGRRGPEQTQGNFGDQDLIRQGTDYKHWPQIAQFAPSASAFFGMSRIGMEVTPSGTWLTYHGAIKLDDKDPQFKDNVILLNK HIDAYKTFPPTEPKKDKKKKTDEAQPLPQRQKKQPTVTLLPAADMDDFSRQLQNSMSGASADSTQA* |

FIG. 4

CHARACTERIZATION OF THE EARLIEST STAGES OF THE SEVERE ACUTE RESPIRATORY SYNDROME (SARS) VIRUS AND USES THEREOF

BACKGROUND OF THE INVENTION

Severe Acute Respiratory Syndrome ("SARS") is a human respiratory disease of recent origin, widespread infectivity, recurring incidence, and significant mortality. Specifically, SARS is a recently-observed human disease, with the first cases seen in Guangdong Province, China, in November, 2002. During this 2002-2003 outbreak, the World Health Organization ("WHO") reported more than 30 countries in which the disease had occurred, with 774 of the 8096 patients who had contracted SARS eventually dying of the disease (see the WHO website at who.int/csr/sars/country/table2004_04_21/en/). Moreover, a second outbreak of SARS in four patients in the city of Guangzhou, Guangdong Province, China, between December, 2003, and January, 2004, demonstrated that the disease is recurrent, and therefore continues to be of serious impact to worldwide human health (see the WHO website at who.int/csr/don/2004_01_27/en/ and who.int/csr/don/2004_01_31/en/).

Subsequent to the initial SARS outbreak, an intensive collaborative research effort by the international scientific community identified the etiological agent causing the disease to be a novel coronavirus, the SARS coronavirus ("SARS-CoV" or, synonymously, "SCoV" or "SARS virus") (Ksiazek et al., *N. Engl. J. Med.* 348:1947 (2003); Peiris et al., *Lancet* 361:1319 (2003); Drosten et al., *N. Engl. J. Med.* 348:1967 (2003)). This identification of the causative agent of SARS as a coronavirus is consistent with the known role of these viruses in animal and human respiratory diseases; as many as one third of all human mild upper respiratory tract illnesses, for example, are caused by human coronaviruses. Interestingly, however, although SARS-CoV is clearly a member of this diverse group of positive-stranded RNA viruses, based on RNA sequence comparisons it appears that SARS-CoV does not fall within any of the coronavirus evolutionary groups previously characterized, i.e., is not closely related to any previously known coronavirus (Rota et al., *Science* 300:1394 (2003); Marra et al., *Science* 300:1399 (2003)).

Although the agent responsible for SARS has been identified, successful prevention and treatment of the disease requires an additional understanding of the origin of SARS-CoV in humans, as well as knowledge of how the virus mutates during an outbreak of SARS. With regard to origin, as discussed above, SARS has only recently been observed in humans, suggesting the prior existence of SARS-CoV, or a close relative of SARS-CoV, in a separate, non-human source with which humans have had recent contact. Thus an important component in the control and prevention of future SARS outbreaks will be an understanding of this origin, including: knowledge of how the SARS coronavirus crosses this species barrier, i.e., the characteristics of the virus at the point when it first infects humans; and, an understanding of the non-human source of the coronavirus.

In this latter regard, a variety of data strongly implicate Himalayan palm civets (*Paguma larvata*; "palm civets" or, synonymously, "civets") as the non-human source of SARS-CoV (although probably not the ultimate repository of the disease itself; see Example 2 below). First, the early cases of SARS in both the 2002-2003 and 2003-2004 outbreaks were associated with patient exposure to these exotic food animals, suggesting that they are the vectors for transmission to humans of SARS-CoV, or a close relative of SARS-CoV. And, second, it has been shown that palm civets indeed harbor a SARS-CoV-like coronavirus (synonymously "SCoV-like coronavirus") highly related to SARS-CoV (99.8% RNA sequence homology), further suggesting the origin of the latter human form of the coronavirus from transmission of the former palm civet form (Guan et al., *Science* 302:276 (2003)). Despite this knowledge of the likely non-human source of the SARS coronavirus, however, the exact form of the virus at or immediately after transmission has not yet been elucidated.

With regard to the mutation of SARS-CoV during a SARS outbreak, a number of studies have demonstrated a variety of mutational changes in the SARS-CoV RNA sequences of various patients from the 2002-2003 outbreak (Ruan et al., *Lancet* 361:1779 (2003); Lan-Dian et al., *Acta Pharmacol. Sin.* 24:741 (2003)). Such changes are hardly surprising, in light of the recent introduction of SARS into humans from palm civets or some other non-human source discussed above, the strong selection pressures on the virus resulting after such a change in host, and the inherently high rate of genetic mutation in the coronaviruses resulting from their use of RNA as their genetic material. Such mutations in the underlying RNA genetic material are expected to result in new SARS coronaviral strains better adapted for growth in the human host, for ability to evade the human immune system, or with other novel properties which impact human health, for example the human-human hyper-infectivity of particular strains of the SARS coronavirus in what are termed "superspreader" events. Therefore, understanding the changes that occur in the SARS coronavirus during the course of an outbreak is critical to controlling and ultimately preventing the disease.

In light of the preceding discussion, it is clear that, although changes in the SARS coronavirus occurring at all stages of a SARS outbreak are important to an understanding of how to combat SARS, it is particularly important to understand the evolution of the SARS coronavirus in the earliest stages of its infection of humans, i.e., those stages at or immediately following the point at which the coronavirus crosses the species barrier. Such understanding of the earliest strains of the SARS coronavirus can be expected to lead to a variety of insights into prevention and treatment of the disease, including, for example: the development of molecular markers for identifying different evolutionary stages of the SARS-CoV (i.e., different stages occurring during a SARS outbreak), thereby allowing for the prediction of the severity of the disease in an infected patient, as well as likelihood of infectivity to others; the development of procedures based on the properties of the early SARS-CoV strains obtained, e.g., the use of the RNA genetic material of early SARS strains to obtain SARS coronaviral proteins important for the spread of these early strains (or their initial transmission to humans) for study and ultimately for targeting for drug inhibition; and, the use of these early SARS coronavirus strains in whole or in part in the development of vaccines to prevent SARS.

Despite this need for an understanding of the earliest stages of the SARS virus in humans, to date the data on the evolution of the SARS coronavirus during these earliest outbreak stages are limited. For example, Ruan et al. (*Lancet* 361:1779 (2003)) compared the RNA nucleotide sequences of fourteen SARS-CoV sequences from the 2002-2003 outbreak, only one of which (GZ01, also referred to in the literature as GD01) dates to the early stages of this outbreak. Although these data allowed Ruan et al. to make a number of statements regarding nucleotide positions of the SARS- CoV RNA associated with different regional SARS outbreaks, in light of the paucity of data from the earliest stages of the 2002-2003 outbreak, few conclusions can be drawn from the data of Ruan et al. about the critical earliest stages of the evolution of SARS-CoV.

There is thus a great need to obtain data regarding the earliest stages of the evolution of the SARS coronavirus in humans in order to understand, treat, and prevent SARS.

SUMMARY OF THE INVENTION

The present invention satisfies the need to better understand the earliest stages of the evolution of the SARS coronavirus. Specifically, the present invention is directed to the characterization of different SARS-CoV strains occurring at different stages of a SARS outbreak, and particularly to previously uncharacterized earliest stage SARS-CoV strains, i.e., SARS-CoV strains obtained from the earliest infected patients in a SARS outbreak, and to the uses of these data for, e.g., disease diagnosis, drug development, and vaccine development.

Thus one embodiment of the present invention is directed to the use of the data obtained in these sequence comparisons to identify insertions, deletions, and single nucleotide variations (SNV) within the SARS virus RNA that are characteristic for each stage of SARS virus, i.e., that serve as stage-specific molecular markers for the different strains characteristic of the earliest stages (including both "early-early" and "early" stages as defined elsewhere herein), middle, and late stages of an outbreak. The present invention also includes methods for using this information in determining the staging of SARS-CoV or SARS-CoV-like sequences of interest, as well as kits for conducting such analyses.

A second embodiment of the present invention is directed to the SARS coronaviral nucleotide sequences characteristic of these stages, and particularly to the nucleotide sequences characteristic of earliest stage SARS-CoV sequences (i.e., "early-early" and "early" stages), as well as closely-related SARS-CoV-like sequences. These earliest stage SARS-CoV sequences and closely-related SARS-CoV-like sequences are novel, i.e., first-characterized in the present invention, and may be used as the basis for experiments designed to test the role of any of the proteins encoded by the coronaviral RNA sequence in species specificity and infectivity. Thus, for example, the availability of novel SARS-CoV sequences from the earliest-infected patients of the 2002-2003 SARS outbreak as well as from the 2003-2004 outbreak allow for the use of these sequences to produce proteins characteristic of the virus in its earliest stages, i.e., its state shortly after crossing the species barrier from its non-human source into humans. These nucleotide sequences are supplemented by the availability in the present invention of novel SARS-CoV-like sequences, specifically the previously uncharacterized SARS-CoV-like sequences obtained from civet cats during the period of the 2003-2004 human SARS outbreak. As described elsewhere herein, these sequences are very similar to those of the earliest stage SARS-CoV sequences; therefore, the human-derived SARS-CoV sequences in combination with the civet-derived SARS-CoV-like sequences allow for the more complete study of the earliest stage coronaviral proteins and other viral properties.

Finally, a third embodiment of the present invention is directed to the development of vaccines based on the properties of the novel earliest stage SARS-CoV sequences and closely-related SARS-CoV-like sequences of the present invention. Such vaccines take advantage of the unique properties observed for the earliest stage SARS-CoV, namely, the milder symptoms seen with these coronaviral infections, as well as the lack of human-human infectivity (see, e.g., Example 2 elsewhere herein).

BRIEF DESCRIPTION OF THE DRAWINGS

The foregoing summary, as well as the following detailed description of preferred embodiments of the present invention, will be better understood when read in conjunction with the appended drawings. For the purpose of illustrating the present invention, there are shown in the drawings embodiments which are presently preferred. It should be understood, however, that the present invention is not limited to the precise arrangements and instrumentalities shown.

Figure 1A-1:
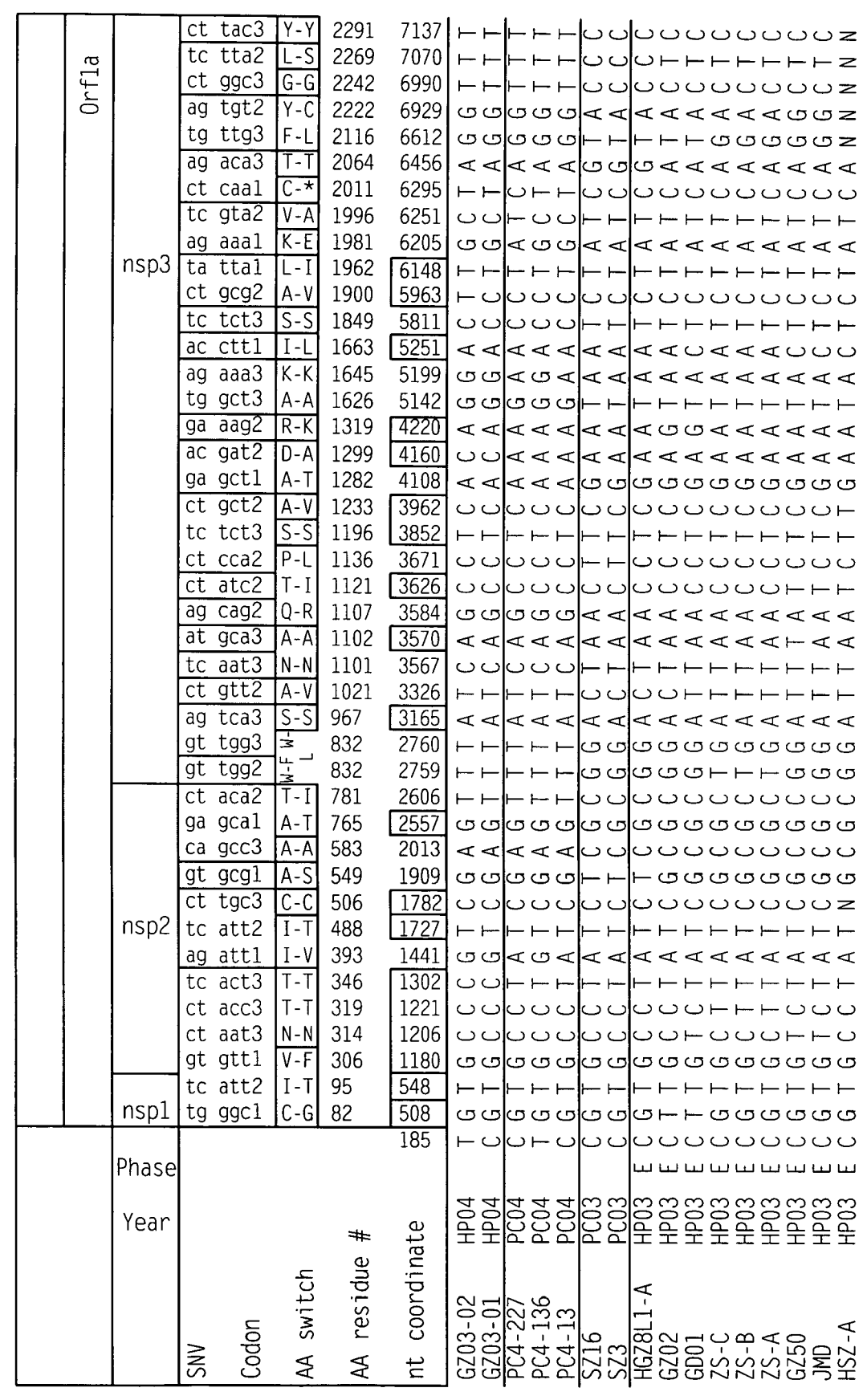
Figure 1A-2:
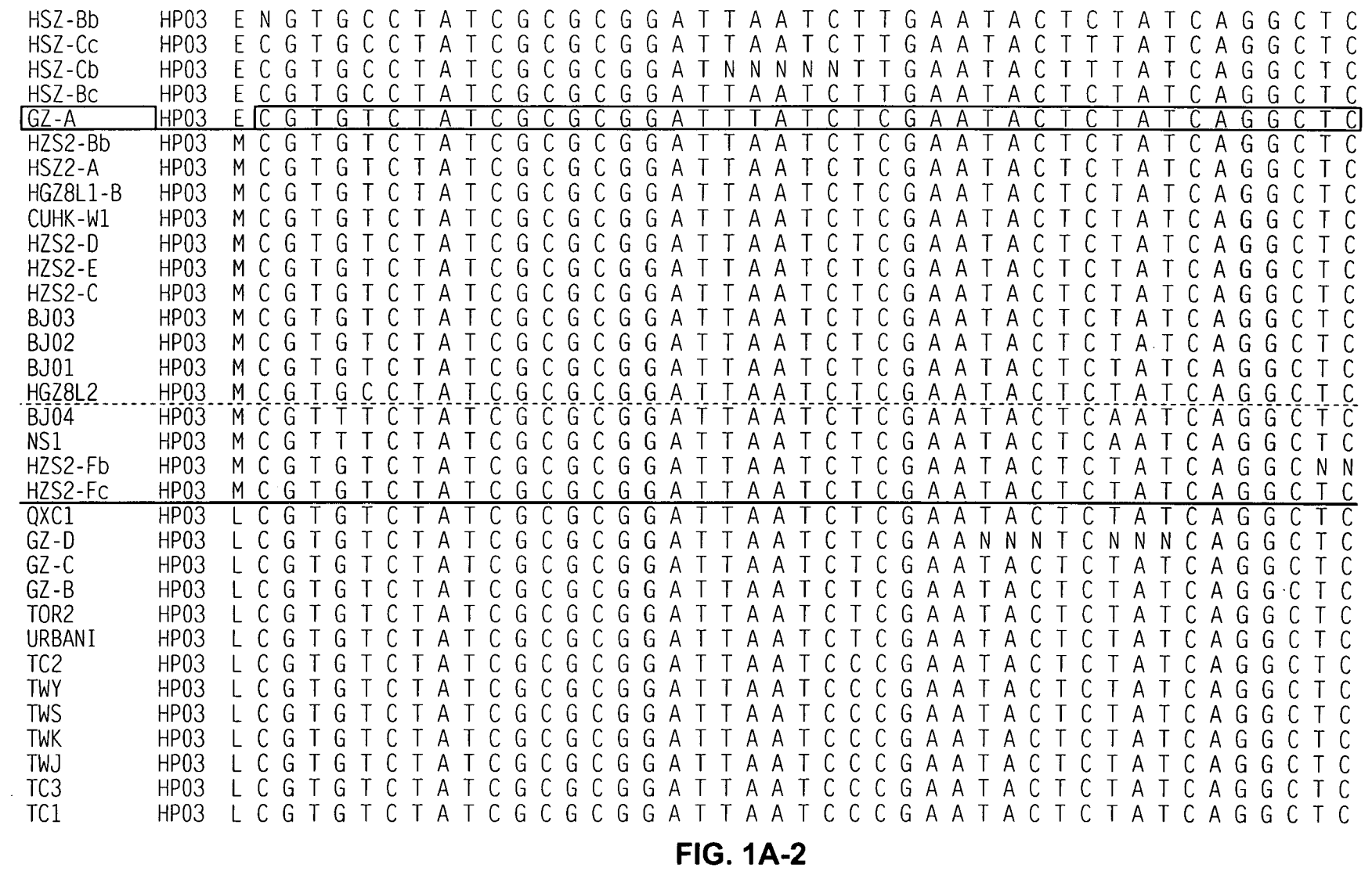
Figure 1B-2:
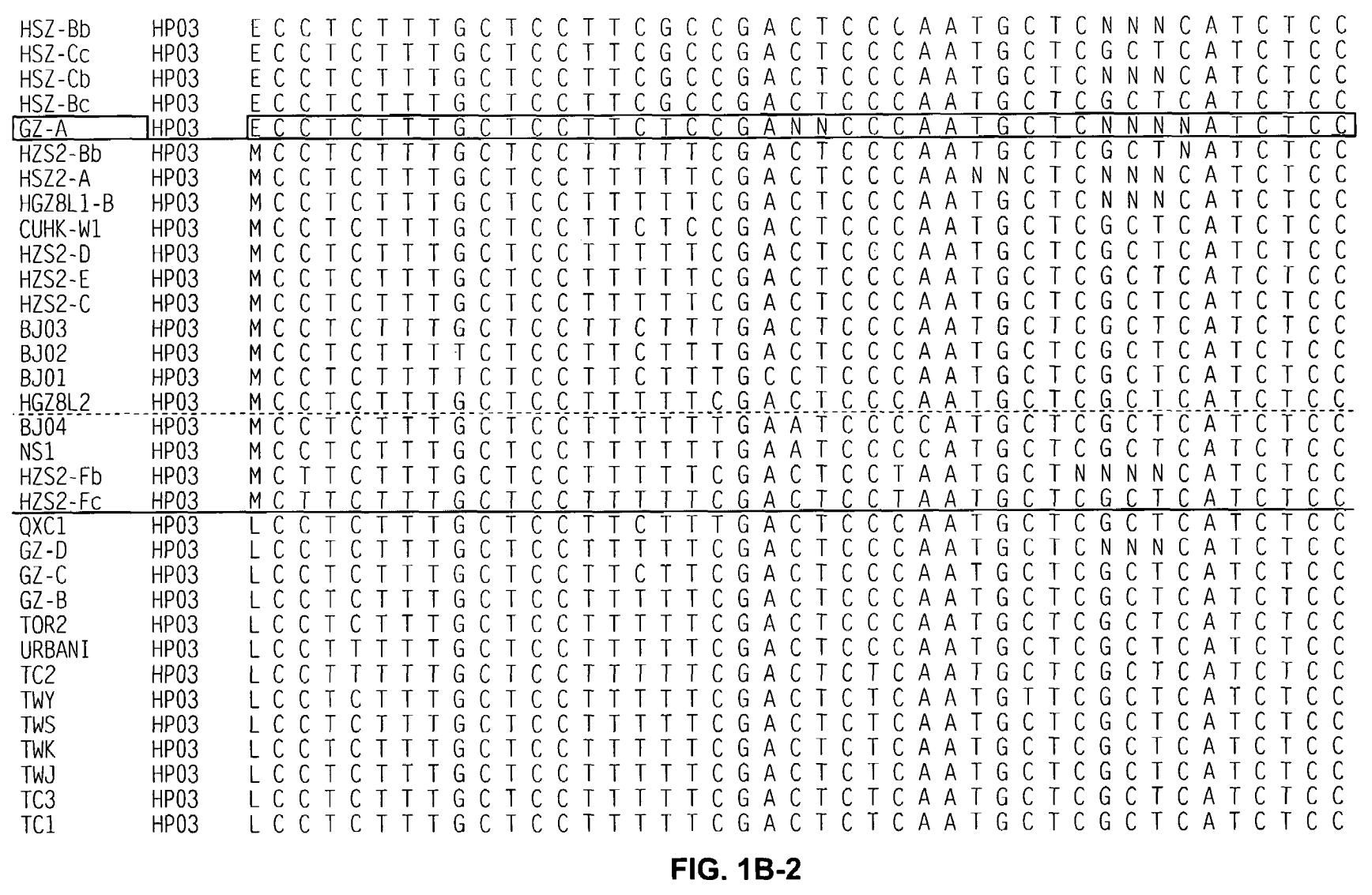
Figure 1C-2:
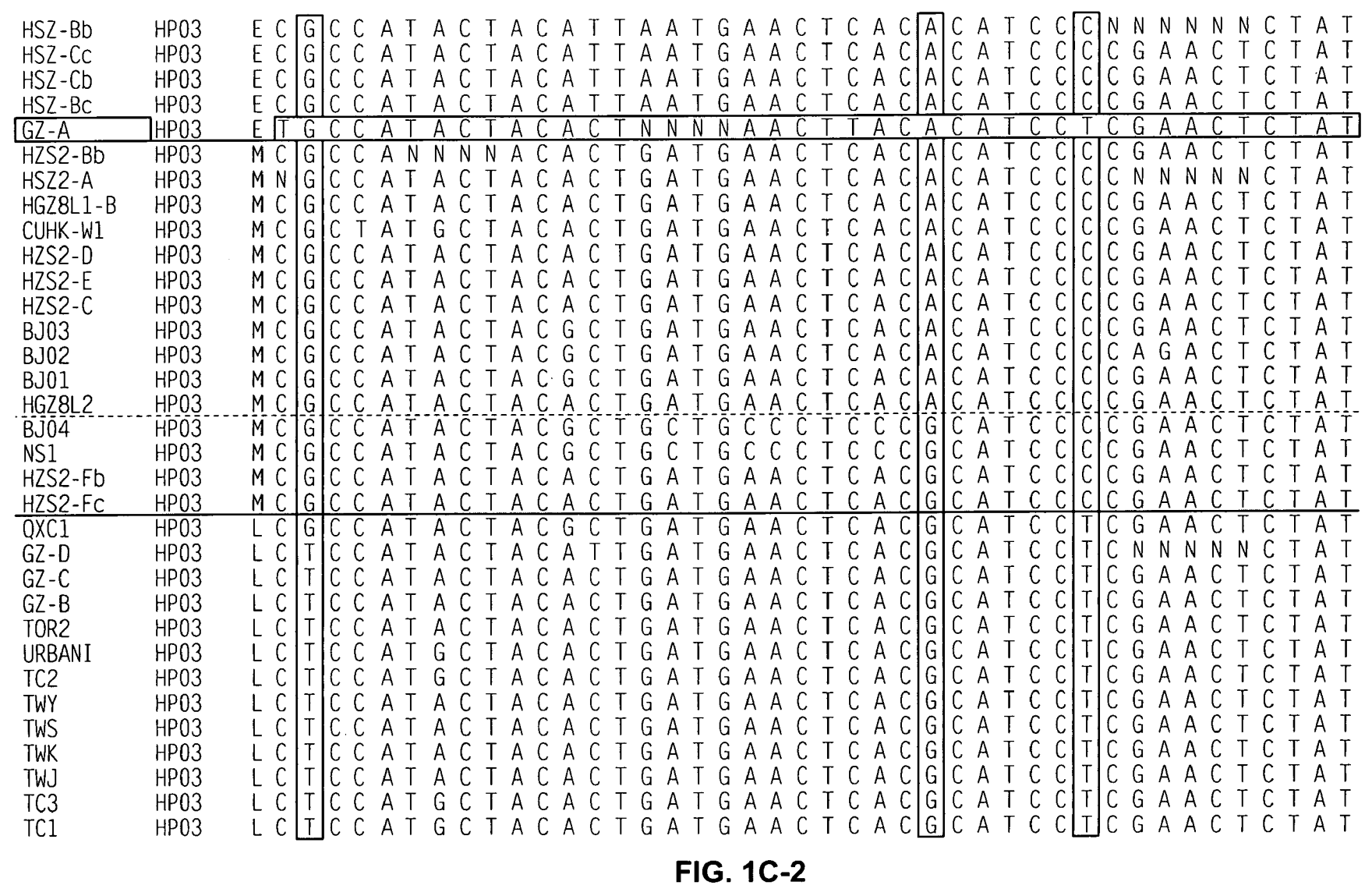
Figure 1D-2:
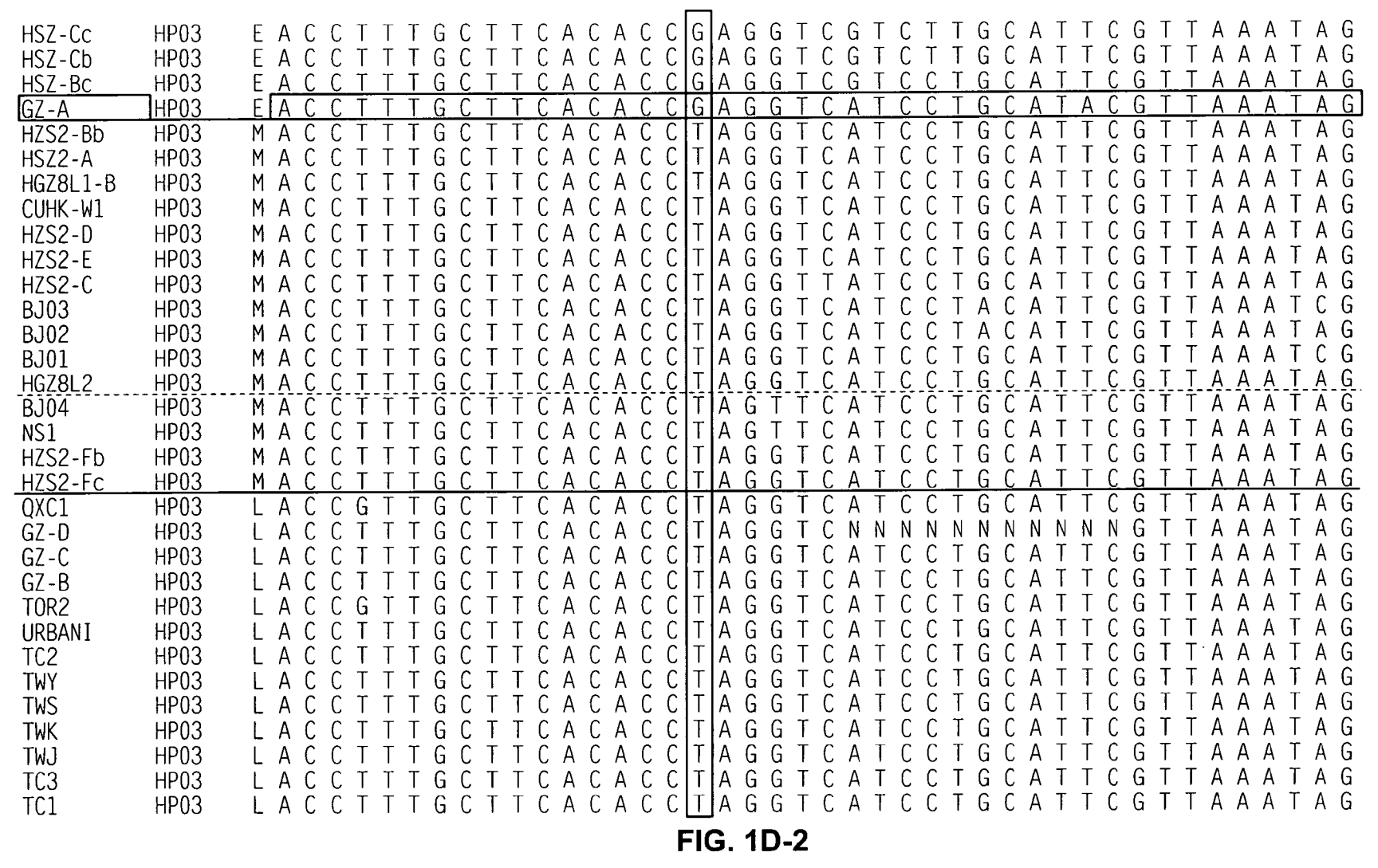
Figure 1E-2:
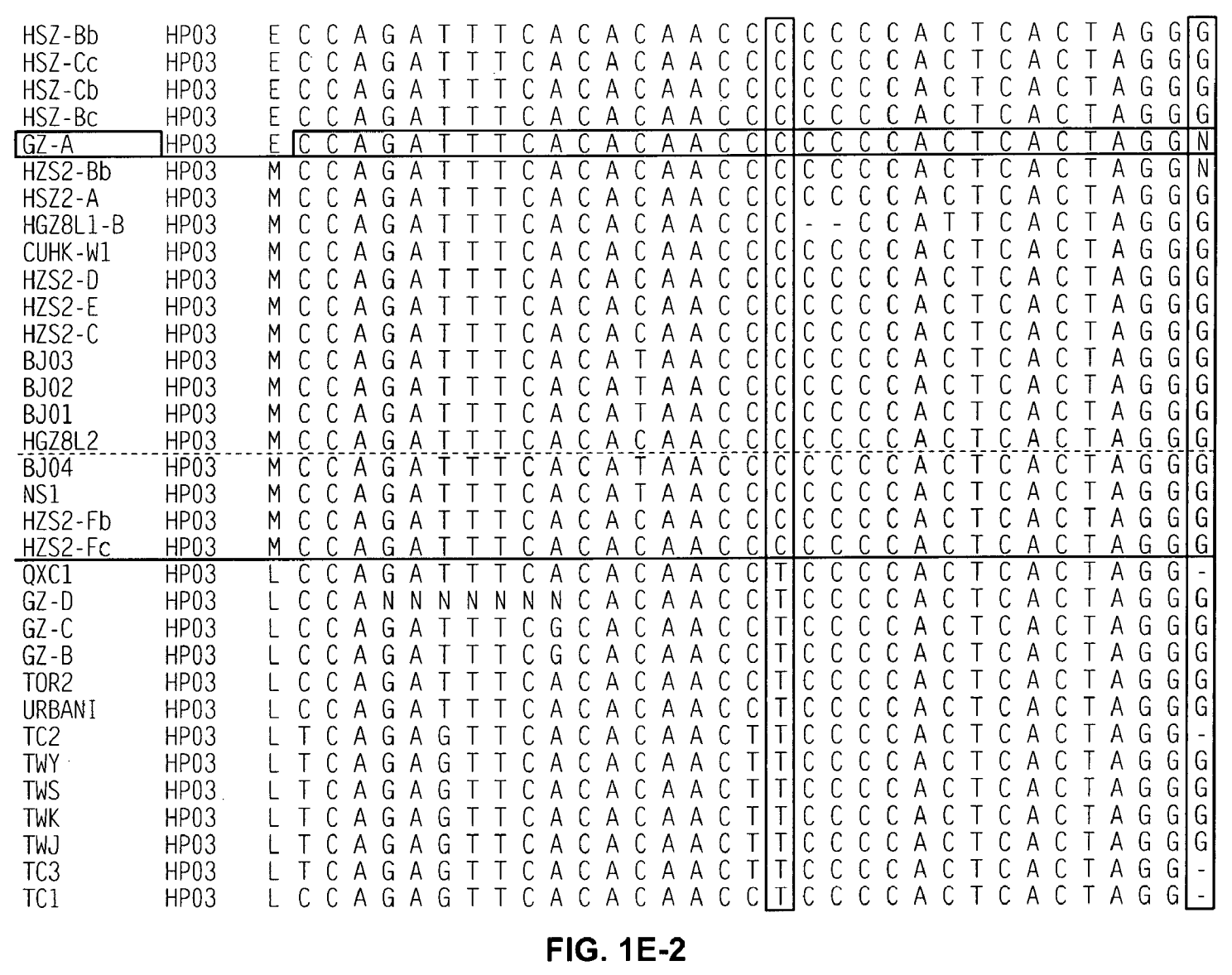
Figure 1F-1:
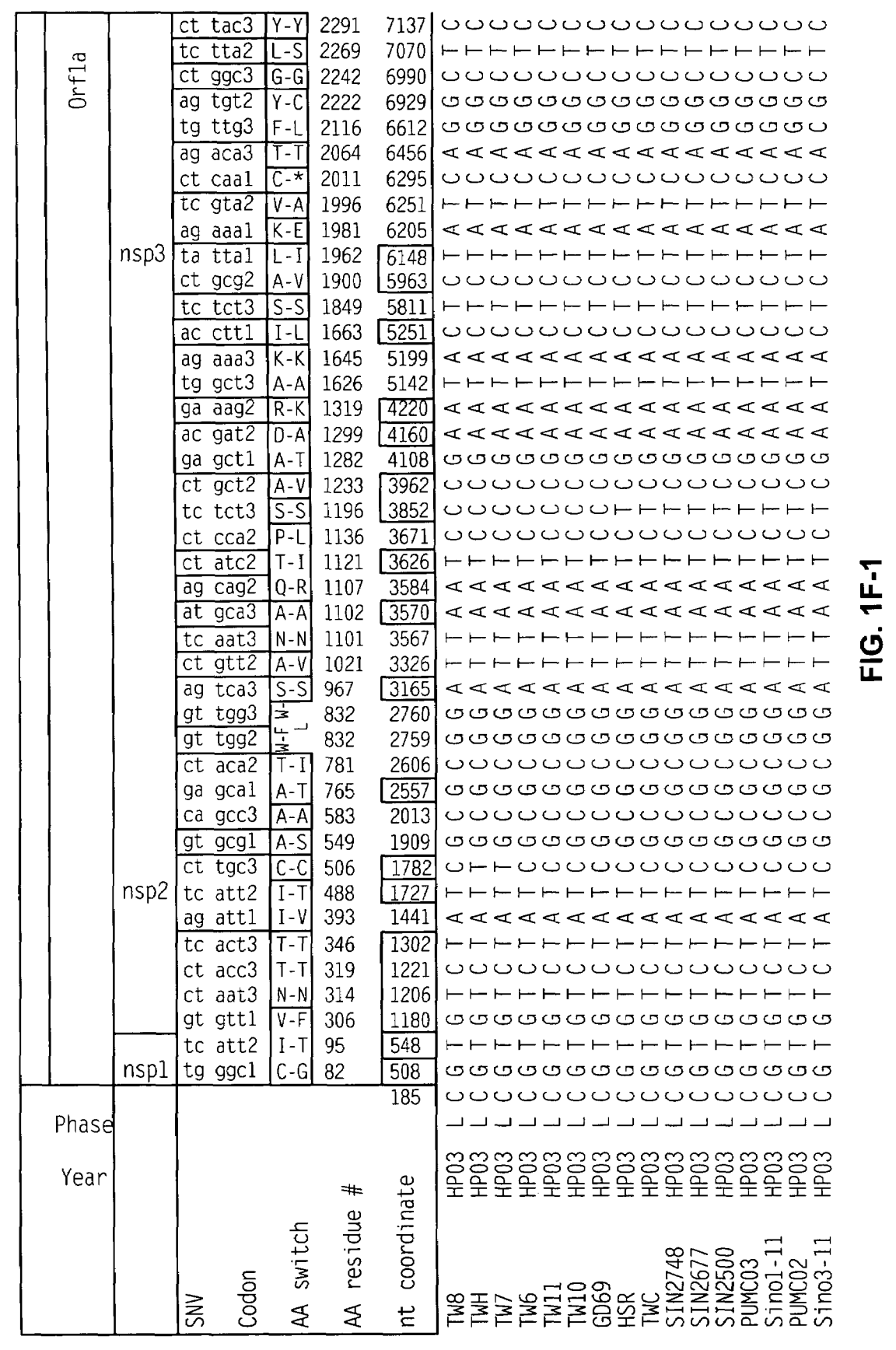
Figure 1F-2:
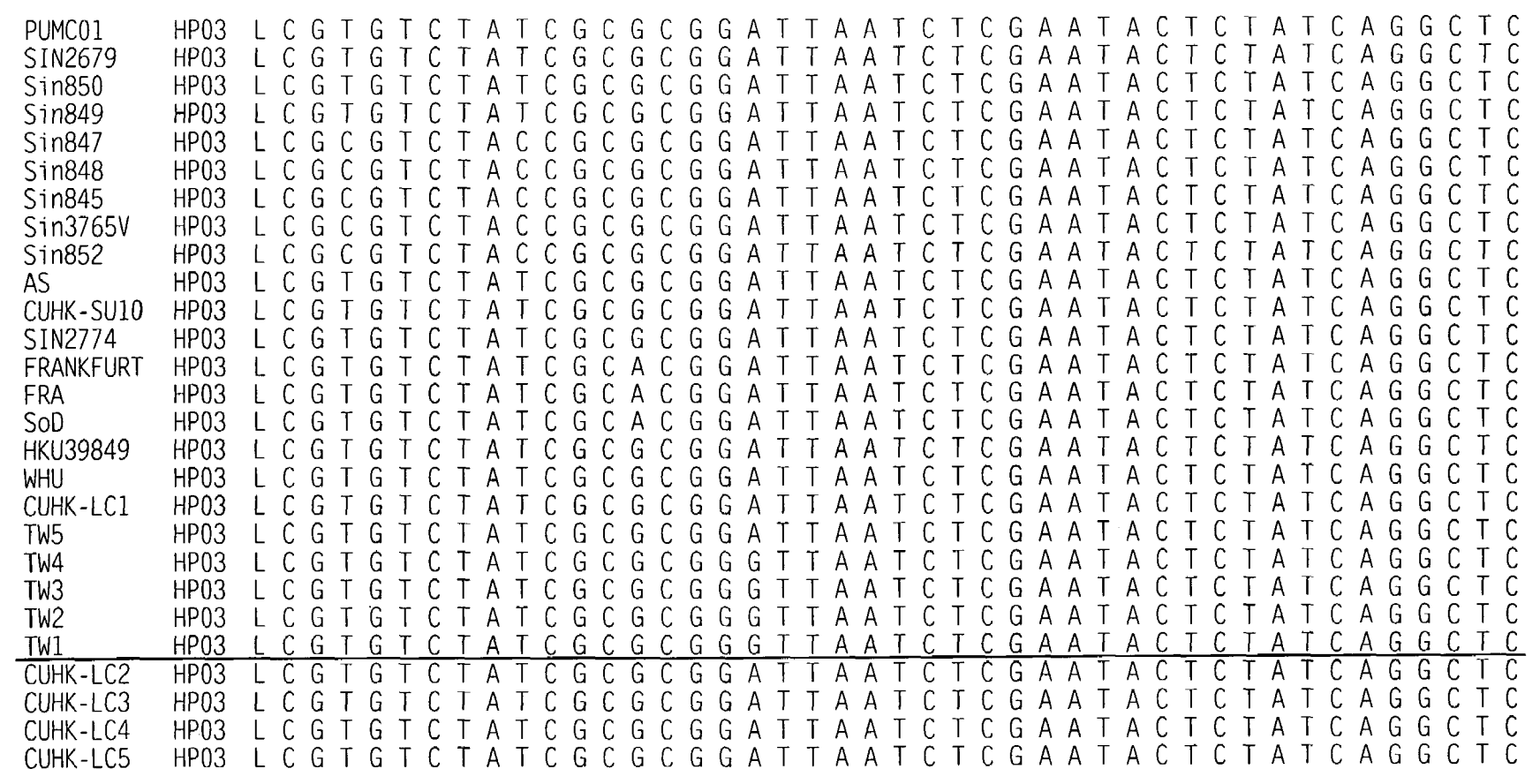
Figure 1G-2:
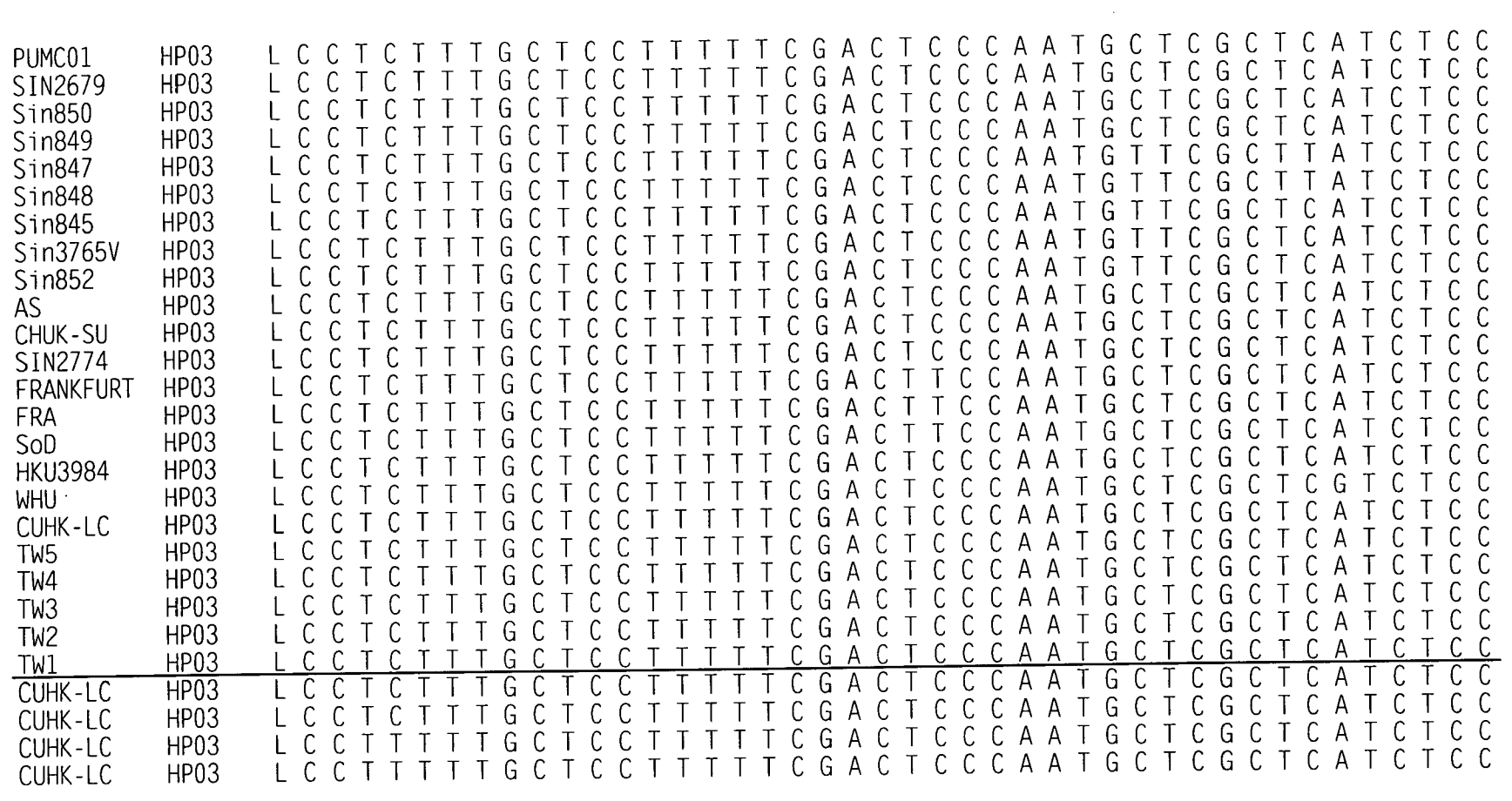
Figure 1H-2:
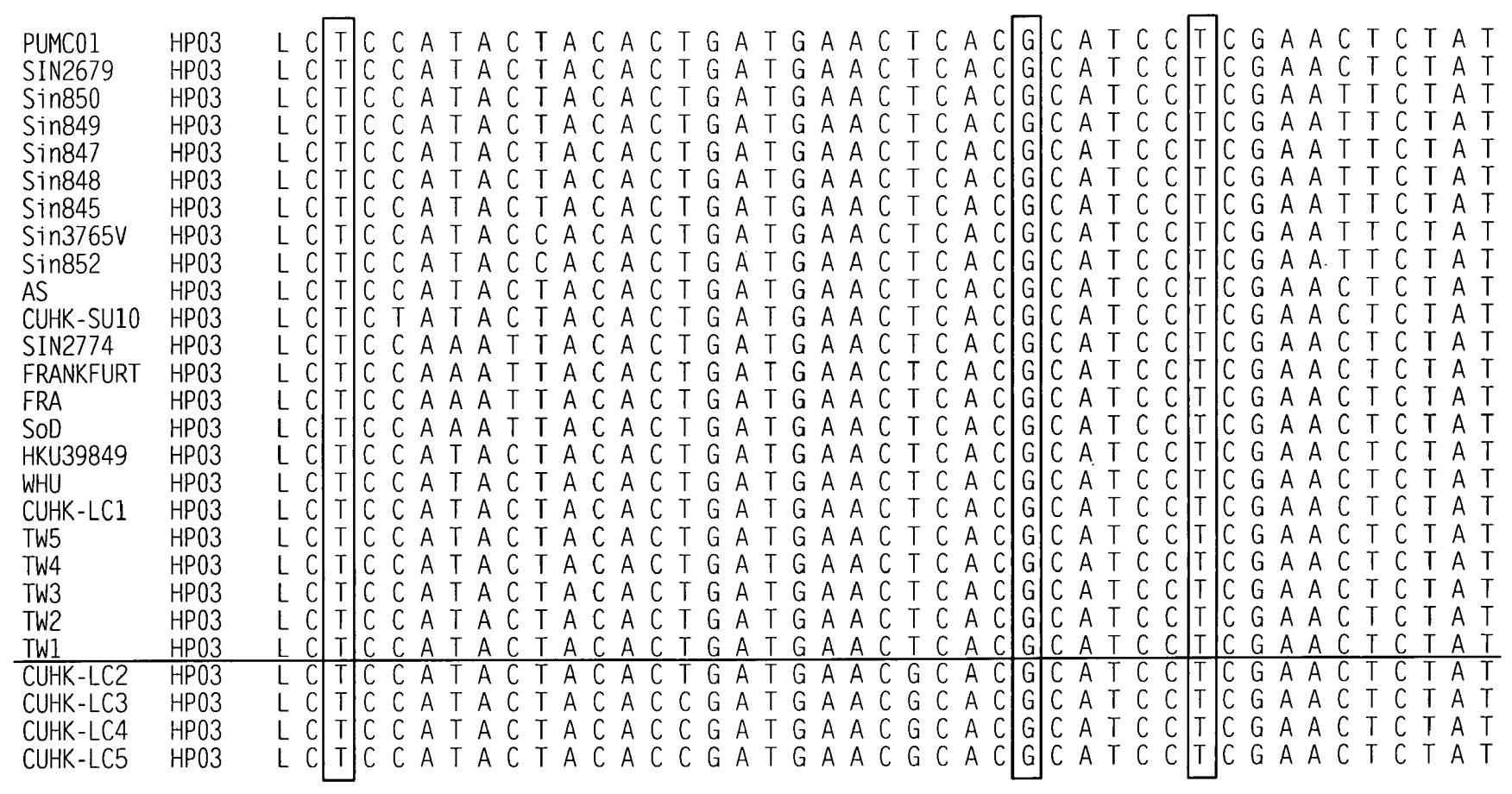
Figure 1I-2:
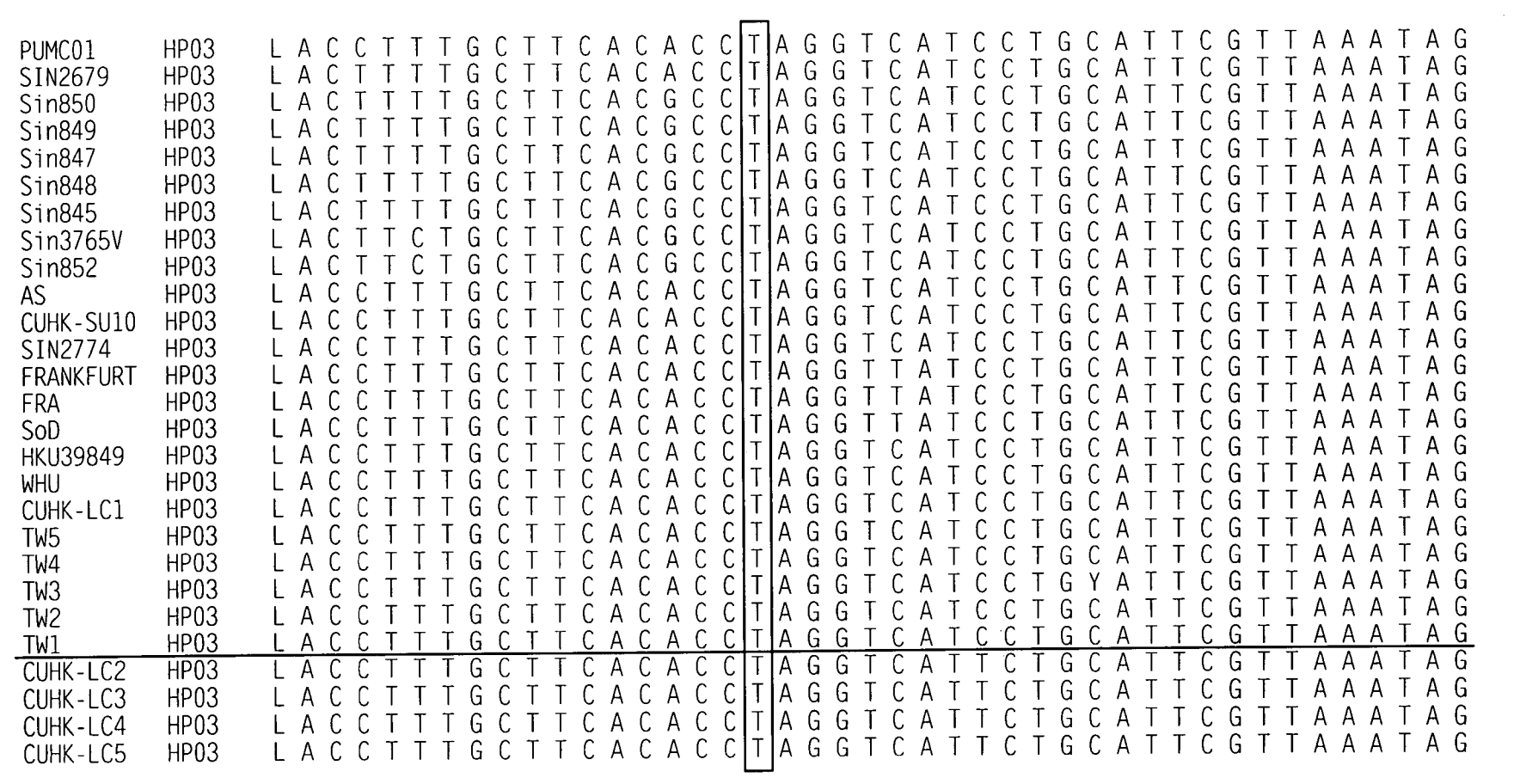
Figure 1J-2:
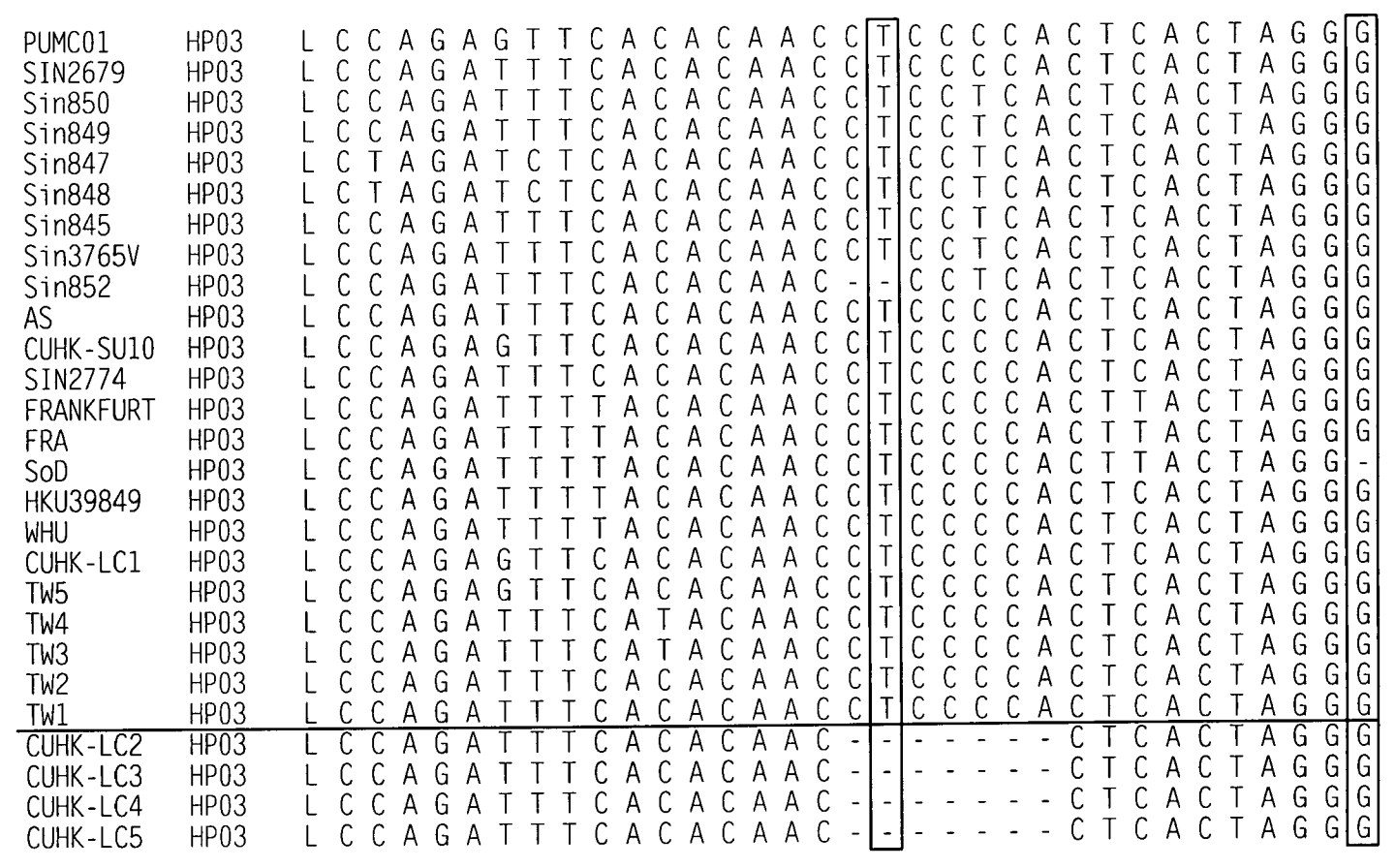

FIGS. 1A-J show the single nucleotide variations (SNVs) for 92 SARS-CoV and SARS-CoV-like coronaviral sequences. Specifically, FIGS. 1A-J show the alignment of 2 human SARS-CoV RNA sequences from the 2003-2004 outbreak (the "HP04" sequences), 3 SARS-CoV-like palm civet RNA sequences obtained in this same period (the "PC04" sequences), 2 SARS-CoV-like palm civet RNA sequences obtained during the period of the 2002-2003 outbreak (the "PC03" sequences), 14 early-stage SARS-CoV RNA sequences from the 2002-2003 outbreak (the "HP03-E" sequences), 15 middle-stage SARS-CoV RNA sequences from the 2002-2003 outbreak (the "HP03-M" sequences), and 56 late-stage SARS-CoV RNA sequences from the 2002-2003 outbreak (the "HP03-L" sequences). Note that FIGS. 1A-E provide a list of all single nucleotide variations (SNVs) for the HP04, PC04, PC03, HP03-E, and HP03-M groups; the 56-member HP03-L group is described in the last 13 lines of FIGS. 1A-E and in FIGS. 1F-J. Early, middle, and late-stage determinations were performed as described in Example 1. Sequence alignments were performed as described in Example 1, using the GZ02 SARS-CoV sequence (SEQ ID NO:1) as the reference sequence. Rows 1 and 2 of the figure show the protein-coding regions of the SARS-CoV RNA. Row 3 shows the SNVs for each position in the table, with the first of the two nucleotides show that of the GZ02 reference sequence. Thus, for example, position 508 is either the T of the GZ02 sequence or other sequences as shown, or the G of the non-GZ02 sequences also indicated for this position in the figure. Row 4 shows the triplet codon containing this SNV, with the number at the end of the triplet codon indicating the exact position in the triplet which contains the SNV. Thus, for example, the "ggc1" shown in this row for position 508 indicates that the first position of the triplet corresponds to the 508 SNV, i.e., that the allowable variant codons corresponding to the 508 SNV are either TGC or GGC. Row 5 shows the single letter amino acid abbreviations corresponding to these two triplets, i.e., for the 508 SNV, C (corresponding to TGC) or G (corresponding to GGC). Row 6 shows the amino acid residue in the appropriate protein product of the coronaviral RNA corresponding to the triplet codon. Row 7 shows the nucleotide coordinate for the SNV, with the numbering indicated relative to the GZ02 reference sequence (SEQ ID NO:1). Finally, the vertically shaded columns at positions 17564, 21721, 22222, 23823, and 27827 are used to highlight these positions; see Example 1 and elsewhere in the text for a detailed discussion of the use of these positions in the present invention. Note that the "N" entries in the figure refer to nucleotides with undetermined identity.

FIGS. 2A-H show a summary of the data of FIGS. 1A-J. Specifically, FIGS. 2A-H show the occurrence in some or all of each of the possible SARS-CoV or SARS-CoV-like groups of FIGS. 1A-J (i.e., HP04, PC04, PC03, HP03-E, HP03-M, and HP03-L) of each of the nucleotides shown in column 2 at the SNV position indicated in column 1. Thus, for example, FIG. 2A shows that a T nucleotide at the 508 SNV occurs only in the HP03-E group, and only in some (but not all) of the members of this group. By contrast, FIG. 2A shows that a T nucleotide at the 1909 SNV occurs in two groups, PC03 and HP03-E, with all members of the PC03 group having this value, but only some of the members of the HP03-E group having this value. FIGS. 2A-H also indicate SNV positions which are characteristic for all members of a single group of FIGS. 1A-J, i.e., situations in which a particular nucleotide at a particular SNV position occurs in only one of the HP04, PC04, PC03, HP03-E, HP03-M, and HP03-L groups, and occurs in all members of that particular group. In these figures, "EE" indicates the "early-early" group referred to in the text, with inclusion in this group requiring that the particular nucleotide at a particular SNV position occur in all of the members of two groups, the HP04 and PC04 groups. In these figures, "E" indicates the "earliest stage" HP04/PC04/PC03/HP03-E group also referred to in the text, with inclusion in this group requiring that the particular nucleotide at a particular SNV position occur in all of the members of the four groups HP04, PC04, PC03, and HP03-E. Note that only a G nucleotide at the 23823 position is indicative of this four-member group.

FIG. 4 shows the predicted coding sequence changes caused by the major deletion events in the Orf7b-Orf8 region of the SARS-CoV genome. The amino acid sequences of the Orf7b, Orf8 (8a and 8b) and N proteins as predicted for the major SARS-CoV deletion variants are listed in the figure. Corresponding nucleotide coordinates for each predicted open reading frame are based on the GZ02 SARS-CoV sequence (SEQ ID NO:1).

DETAILED DESCRIPTION OF THE INVENTION

Figure 3:
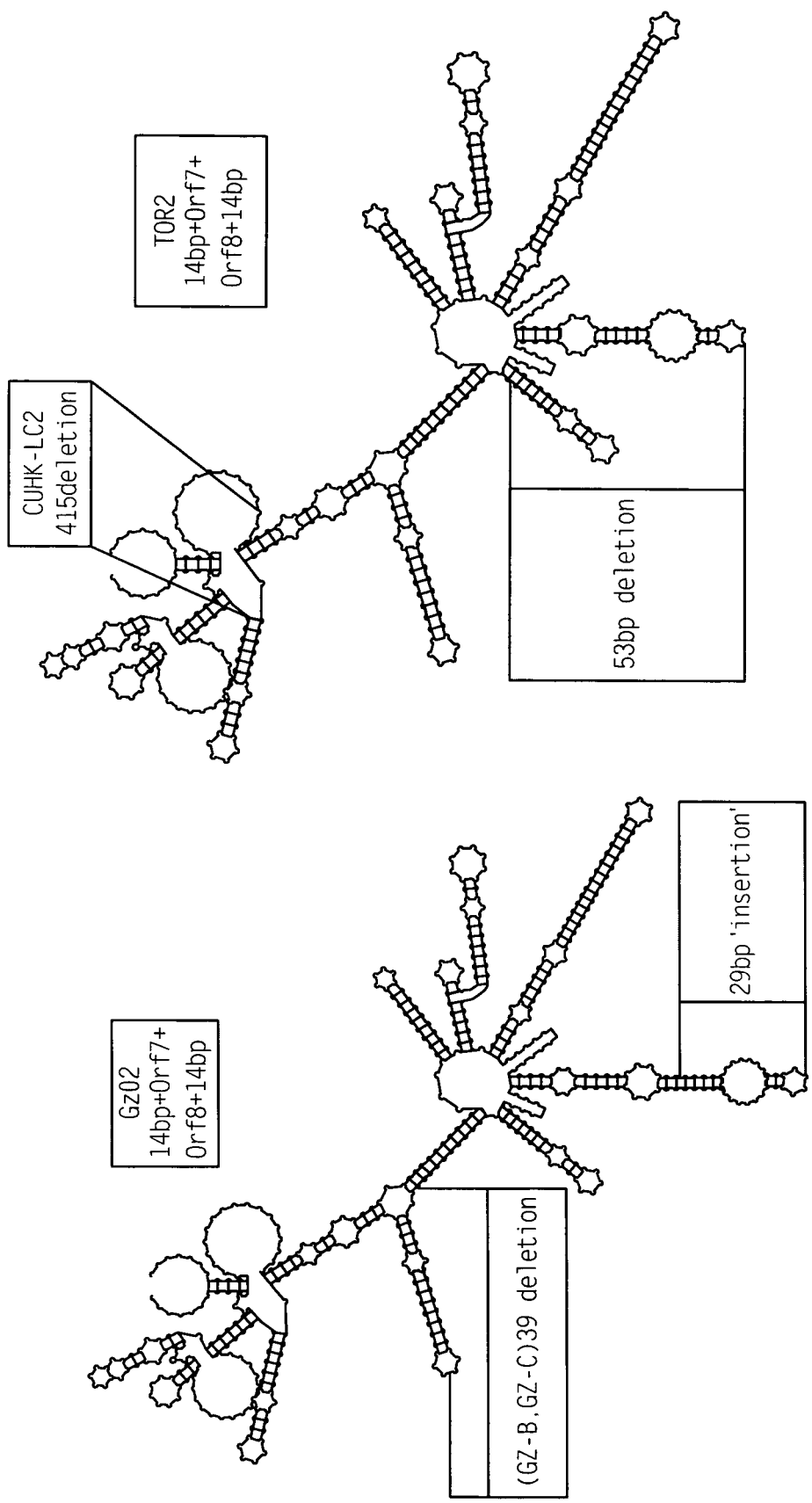
FIG. 3 shows the predicted RNA secondary structure of the Orf7b-Orf8 region of the SARSCoV genome. SARS-CoV genotypic variations caused by major deletion events were observed on a number of occasions during the epidemic. All such deletions were confined to the Orf7b-Orf8 region. The genomic locations of the major deletions observed in this study are indicated on the predicted RNA secondary structures of the longest SARS-CoV genotype (left panel) and the genotype with the 29-nt deletion (right panel). The former genotype is represented by GZ02 (SEQ ID NO:1) while the latter is represented by TOR2 (accession number AY274119 available at the website ncbi.nlm.nih.gov/entrez). This latter genotype predominated for the remainder of the epidemic from the middle phase onwards. For both panels, the illustrated region starts from 14 nucleotides upstream to the start of the predicted Orf7 to 14 nucleotides downstream to the end of Orf8. The illustrated region corresponds to nucleotide positions 27288 to 28161 on GZ02 (SEQ ID NO:1) and nucleotide positions 27259 to 28132 on TOR2. The prediction was made using the VIENNARNA:RNAfold software (available at the website bioweb.pasteur.fr/). GZ-B and GZ-C are two genotypes obtained from two Guangzhou patients with disease onset from mid-March but demonstrated a 39-nt deletion.

The present invention is directed to: the characterization of different SARS-CoV strains occurring at different stages of a SARS outbreak; the identification of stage-specific molecular markers characteristic of one or more of these different stages of a SARS outbreak; to the sequences of SARS-CoV and SARS-CoV like coronaviral strains from these different stages; to vectors, cells, and animals containing these sequences; to the use of the nucleotide and polypeptide sequences of these strains; and, to the development of vaccines based on these sequences.

As used herein, the term "stage-specific molecular marker" (synonymously, "stage-specific marker," "stage-specific nucleotide marker," "molecular marker," "marker," etc.) refers to single or multiple nucleotide positions that are characteristic of one or more members of the different groups of SARS-CoV and SARS-CoV-like strains that occur at different stages of a SARS outbreak. As used herein, stage-specific molecular markers are intended to include both single nucleotide variants (SNVs), and also insertions and deletions in the SARS-CoV or SARS-CoV-like genome.

A stage-specific molecular marker is said to be characteristic of one or more members of the different groups of SARS-CoV and SARS-CoV-like strains that occur at different stages of a SARS outbreak when its occurs in some but not all of these groups. As is shown in FIG. 1 and diagrammatically in FIG. 2, some of the stage-specific molecular markers of the invention occur in only one group, while others occur in more than one group. As these figures also show, a stage-specific molecular marker of the invention need not occur in all members of a particular group, and may instead occur in a subset of the members of a group, including as few as only one member of a particular group.

Although the present invention is directed to the characterization of different SARS-CoV strains occurring at different stages of a SARS outbreak, SARS-CoV strains obtained from the earliest infected patients in a SARS outbreak are of particular interest herein. Thus, as is discussed in detail in Example 1, the present invention is based on a sequence analysis of the SARS-CoV strains obtained from patients in the early, middle, and late stages of the 2002-2003 SARS outbreak, where, for the purposes of this 2002-2003 outbreak: "early-stage" (synonymously, "early phase") refers to the period from the first emergence of SARS to the first documented superspreader event; "middle-stage" (synonymously, "middle phase") refers to the ensuing events up to the first cluster of SARS cases in a hotel (Hotel M) in Hong Kong; and, "late-stage" (synonymously, "late phase") refers to cases following this Hotel M cluster.

As discussed in detail in Example 2, the present invention is also based on a sequence analysis of the SARS-CoV strains obtained from two patients of the 2003-2004 SARS outbreak. As Example 2 demonstrates, this additional sequence analysis allows for the definition of a "very early" stage (synonymously, "early-early" stage) of SARS coronavirus. As used herein the term "earliest stage" refers to the combination of "early-early" and "early" stage coronaviral strains, i.e., both "early-early" and "early" stage strains are intended to be subsumed within this term. Finally, as discussed in detail in Examples 1 and 2, the present invention is also based on palm civet SARS-CoV-like coronavirus sequences obtained during both the 2002-2003 and 2003-2004 SARS outbreak periods, with these sequences used to better define the nature of the virus in the earliest stages of infection in humans.

Thus the present invention is based on SARS-CoV coronavirus sequences from both the 2002-2003 and 2003-2004 SARS outbreaks and, additionally, on palm civet SARS-CoV-like sequences from these same two periods. In the present invention, the following nomenclature is used to identify these four groups of sequences: "HP03" is used to refer to SARS-CoV strains obtained from human patients of the 2002-2003 outbreak; "HP04" is used to refer to SARS-CoV strains obtained from human patients of the 2003-2004 outbreak; "PC03" is used to refer to SARS-CoV-like strains obtained from palm civets during the period of the 2002-2003 outbreak; and, "PC04" is used to refer to SARS-CoV-like strains obtained from palm civets during the period of the 2003-2004 outbreak. In addition, as described in Example 1, the SARS-CoV strains of the 2002-2003 outbreak (i.e., the HP03 strains) are further classified into "early," "middle," and "late" stages, which are represented herein as the "HP03-E," "HP03-M," and "HP03-L" strains, respectively.

Although detailed analyses of these data are presented in Examples 1 and 2 as provided elsewhere herein, a number of points relevant to the present invention will be summarized here. These summary points are not intended as limiting of the present invention, and represent a subset of the aspects of the present invention that are discussed at greater length elsewhere herein, and in particular in Examples 1 and 2.

First, the comparison of the RNA sequences of the HP03-E, HP03-M, HP03-L, and PC03 SARS-CoV and SARS-CoV-like coronaviral groups presented in Example 1 identifies a variety of stage-specific molecular markers characteristic of these groups. Examples of these markers are provided in both the deletion/insertion sequences and the single nucleotide variations (SNVs) of FIGS. 1 and 2, and are discussed in detail in the "SARS Coronavirus Stage-Specific Markers" section below. Of note is the fact that a pentet of SNV positions are particularly informative in such classifications, namely the SNVs at positions 17564, 21721, 22222, 23823, and 27827 of the SARS-CoV sequence. As for elsewhere in the present invention, these sequence positions are given relative to the GZ02 HP03-E reference sequence (SEQ ID NO:1), unless otherwise noted.

Sequence Identifiers

The present invention refers to a number of sequence identifiers. In this regard: SEQ ID NO:1 refers to the CZ02 reference sequence used as the basis for the SARS-CoV and SARS-CoV-like RNA sequences given throughout the (the) specification; SEQ ID NO:2 refers to the 29 nucleotide insertion corresponding to positions 27884-27912 of the GZ02 reference sequence; SEQ ID NO:3 refers to the 53 nucleotide deletion spanning nucleotides 27858-27883 and 27912-27939 of the GZ02 reference sequence; SEQ ID NO:4 refers to the nucleotide and corresponding amino acid sequences of the spike ("S") protein, which occurs at nucleotides 21492-25259 of the GZ02 reference sequence; SEQ ID NO:5 is the S protein amino acid sequence; SEQ ID NO:6 is the sense PCR primer of Example 3; and, SEQ ID NQ:7 is the anti-sense PCR primer of Example 3. SEQ ID NO:8 refers to the amino acid sequence of Orf7b present in SARS-CoV deletion variants GZ02, TOR2, HGZ8LI-B, and CUHK-LC2, spanning nucleotides 27635-27769 of the GZ02 reference sequence; SEQ ID NO:9 refers to the amino acid sequence of the Orf8a and Orf8b of SARS-CoV deletion variant GZ02, spanning nucleotides 27776-28144 of the GZ02 reference sequence; SEQ ID NO:10 refers to the nudeocausid protein present in SARS-CoV deletion variants GZ02, TOR2, HGZ8LI-B and GZ-C, GZ-B, spanning nucleotides 28146-29414 of the GZ02 reference sequence; SEQ ID NO:11 refers to the amino acid sequence of Orf8a of the TOR2 SARS-CoV deletion variant, spanning nucleotides 27776-27924 of the GZ02 reference sequence; SEQ ID NO:12 refers to the amino acid sequence of Orf8b of the TOR2 SARS-CoV deletion variant, spanning nucleotides 27861-28144 of the GZ02 reference sequence; SEQ ID NO:13 refers to the amino acid sequence of Orf8a of the HGZ8LI-B SARS-CoV deletion variant spanning nucleotides 27776-27963 of the GZ02 reference sequence; SEQ ID NO:14 refers to the nucleocapsid protein sequence of the CUHK-LC2 SARS-CoV deletion variant, spanning nucleotides 27635-29414 of the GZ02 reference sequence; and SEQ ID NO:15 refers to the amino acid sequence of Orf7b of the GZ-C, GZ-B SARS-CoV deletion variant, spanning nucleotides 27638-27844 of the GZ02 reference sequence.

SARS Coronavirus Stage-Specific Molecular Markers

One embodiment of the present invention is directed to the use of the data obtained in the sequence comparisons of the novel SARS-CoV and SARS-CoV-like sequences of the present invention to identify insertions, deletions, and single nucleotide variations (SNV) that are characteristic for each stage of SARS virus, i.e., that serve as molecular markers for the different strains characteristic of the earliest stages (including both "early-early" and "early" stages), middle, and late stages of an outbreak.

Thus as is described in Example 1, the present invention provides for the comparison of 63 SARS-CoV and SARS- CoV-like sequences, including the following previously uncharacterized sequences: GZ02 (SEQ ID NO:1), HGZ8L1-A, HSZ-Cc, HSZ-A, HSZ-Bb, HSZ-Cb, HSZ-Bc, HGZ8L1-B, ZS-A, ZS-B, ZS-C, HZS2-D, HZS2-E, HZS2-C, HZS2-Bb, HZS2-A (all HP03-E sequences); HGZ8L-2, HZS2-Fc, HZS2-Fb (all HP03-M sequences); and, GZ-D, GZ-B, GZ-C, CUHK-LC2, CUHK-LC3, CUHK-LC4, and CUHK-LC5 (all HP03-L sequences).

As is described in Example 1 and shown in FIGS. 1-5, these comparisons provide a number of insertions/deletions (FIGS. 2-5) and SNVs (FIGS. 1-2 and 5) that may be used to classify any particular SARS-CoV or SARS-CoV-like sequence within the HP03-E, HP03-M, HP03-L, and PC03 groups provided in this Example. Although these data do not include the HP04 and PC04 data of Example 2, they are also applicable to these groups of SARS-CoV and SARS-CoV-like strains.

Thus with regard to the insertions/deletions of Example 1 these data show an insertion of 29 nucleotides (CCTACTG-GTTACCAACCTGAATGGAATAT; SEQ ID NO:2) in the Orf8 region (this insert is part of the GZ02 reference sequence (SEQ ID NO:1) at positions 27884-27912, i.e., immediately after position 27883 at which the insertion occurs; the Orf8 region itself spans nucleotides 21637-28147 of the GZ02 sequence) in seven of the HP03-E SARS-CoV strains (GZ02, HGZ8L1-A, HSZ-A, HSZ-Bb, HSZ-Bc, HSZ-Cb and HSZ-Cc; in Example 1 the HSZ-Bb and HSZ-Bc strains are summarized as HSZ-B, and the HSZ-Cb and HSZ-Cc strains are summarized as HSZ-C), i.e., the same sequence in this region as observed for the PC03 sequences originally characterized by Guan et al. (*Science* 302:276 (2003)). By the middle phase of the HP03 outbreak, however, the characterized SARS-CoV strains lack this 29 nucleotide insertion (see, e.g., Rota et al., *Science* 300:1394 (2003); Marra et al., *Science* 300:1399 (2003); Ruan et al., *Lancet* 361:1779 (2003)). Thus the presence of the 29 nucleotide insertion of SEQ ID NO:2 at position 27883 may be used in the identification of a SARS-CoV sequence as an early-stage sequence, i.e., this 29 nucleotide sequence serves as an example of what is termed herein to be an "insertion early-stage-specific molecular marker."

Also as described in Example 1, a lung biopsy of a patient from the middle phase of the 2002-2004 outbreak (i.e., HP03-M) was found to contain two SARS-CoV genotypes. In both genotypes the 29 nucleotide deletion was observed; unique to this patient, however, was the presence of an additional 53 nucleotide deletion bracketing either side of the region of the 29 nucleotide deletion (i.e., AACCTCAT-GTGCTTGAAGATCCTTGTAAGGTACAA-CACTAGGGGTAATACTTA (SEQ ID NO:3) spanning nucleotides 27858-27883 and 27912-27939 of the GZ02 sequence (SEQ ID NO:1)) in some (but not all) of the SARS-CoV clones obtained from this patient and analyzed by sequencing. Specifically, 17 of 27 clones from this patient had sequences lacking these 53 nucleotides, while the remaining 10 clones had the 53 nucleotides in this position, i.e., had the same sequence in this region as was observed for other SARS-CoV HP03-M strains. Finally, an 82 nucleotide deletion representing both the 29 and 53 nucleotide deletions was found in four more of the HP03-E strains (ZS-A, ZS-B, ZS-C, and HGZ8L1-B). Thus these 53 and 82 (i.e., 29+53) nucleotide deletions may potentially also be used in the classification of SARS-CoV strains, i.e., for the staging of a SARS-CoV strain, similarly to the staging described above for the 29 nucleotide sequence. Thus these deletions serve as examples of what are termed herein to be "deletion early-stage-specific molecular markers."

Figure 6:
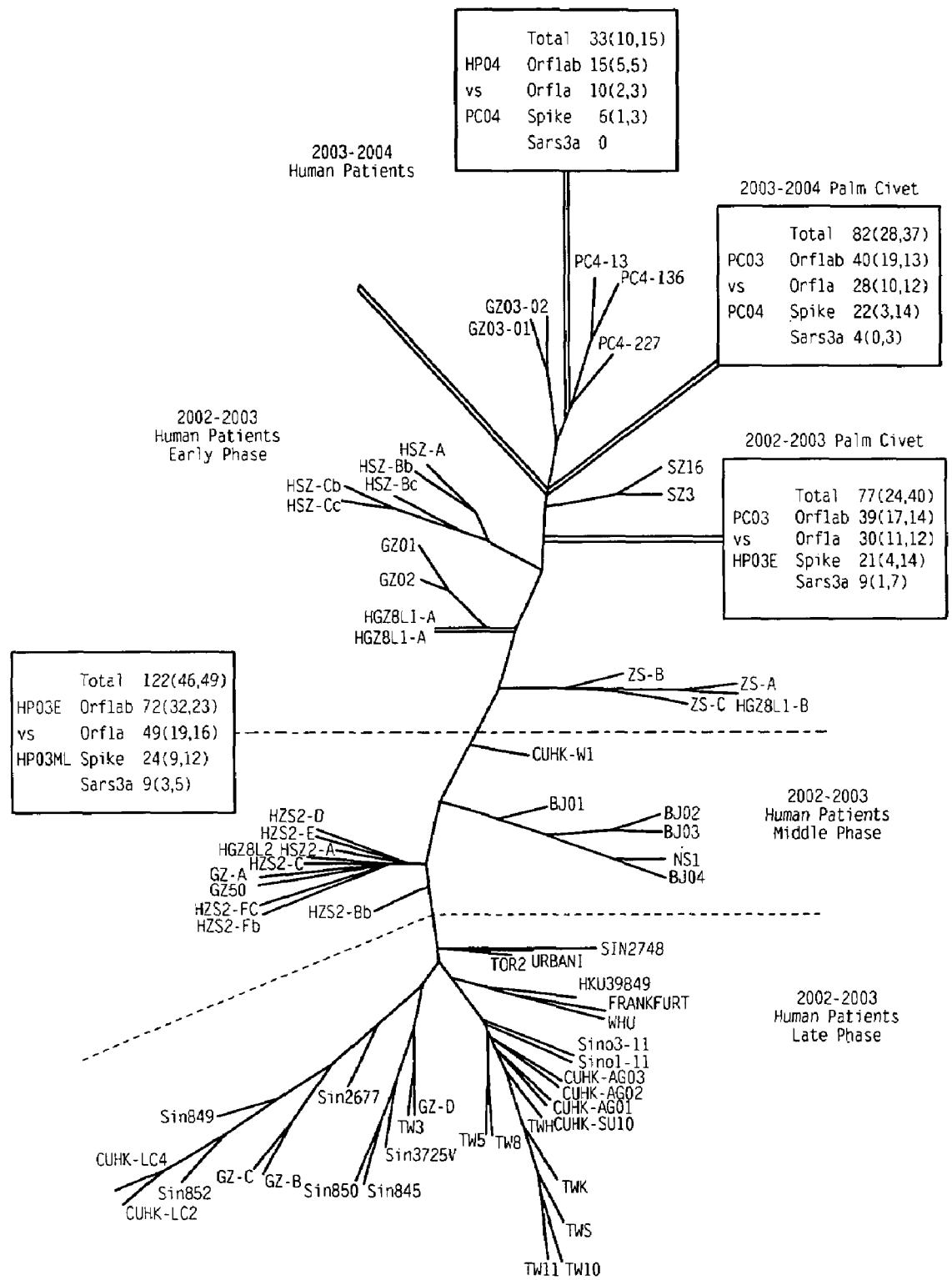
FIG. 6 shows the genotype clustering of SARS-CoV and SARS-CoV-like coronaviruses from the outbreaks of 2002-2003 and 2003-2004. Specifically, an unrooted phylogenetic tree of SARS-CoV and SARS-CoV-like coronaviruses genomes was constructed based on the data of Examples 1 and 2. The map distance between individual sequences represents the extent of genotypic difference. To highlight the variations between neighboring clusters, the total number of single nucleotide variations (SNVs) as well as the numbers of synonymous and non-synonymous mutations (causing drastic amino acid changes) present in at least two independent samples are shown in the boxes.

With regard to the use of the SNVs of the present invention in staging of SARS-CoV strains, both Examples 1 and 2 provide a variety of SNVs that are useful for such staging (i.e., serve as what are termed to be "SNV stage-specific molecular markers"), with Example 2 supplementing the data of Example 1. Specifically, Example 2 provides an analysis of 5 additional coronavirus sequences: 2 SARS-CoV sequences obtained from two of the four patients of the 2003-2004 SARS outbreak in Guangzhou (GZ03-02 and GZ03-01); and, 3 palm civet SARS-CoV-like sequences obtained from palm civets in the Guangzhou food market during the same period (PC4-13, PC4-136, and PC4-227). As shown in FIG. 6 and described in Example 2, these sequences are exceptional in that they are more closely related to one another than they are to either of the two HP03-E or PC03 outgroups (i.e., GZ03-02, GZ03-01, PC4-13, PC4-136, and PC4-227 all group together on the unrooted phylogenetic tree shown in FIG. 6; see also FIGS. 7A-C for a similar analysis using the Spike, sars3a, or nsp3 sequence regions, respectively). These data suggest an "early-early" stage containing the PC04 and HP04 sequences; see elsewhere herein for a complete discussion.

FIGS. 1 and 2 summarize the combined data of Examples 1 and 2 regarding SNVs useful in the present invention. Specifically, FIG. 1 provides the SNVs for 92 SARS-CoV and SARS-CoV-like coronaviral sequences, with all 6 groups identified in Examples 1 and 2 provided in this Figure (i.e., HP04, PC04, PC03, HP03-E, HP03-M, and HP03-L).

The skilled artisan will recognize that any nucleotide that is present in some of these groups and absent in others will act as a molecular marker either in light of its presence in one or more groups or, alternatively, in light of its absence in one or more groups. Thus the occurrence of a C at position 4160 in the GZ02 reference sequence (SEQ ID NO:1) is an example of a molecular marker of use in identifying SARS-CoV sequences falling into the HP04 group, as is shown both in FIG. 1 and in FIG. 2. Referring to FIG. 1, it is apparent that position 4160 is a C for both the HP04 sequences; for all other sequences in the remaining groups (PC04, PC03, HP03-E, HP03-M, and HP03-L), this position is an A. This pattern is also shown graphically in FIG. 2, where only the column labeled "HP04" in the section labeled "Nucleotide Present in All Members of Group Below" is indicated, thereby indicating that this nucleotide (C) at this position 4160 is predictive of a sequence falling within the HP04 group of SARS-CoV strains. On the basis of the observed pattern in the data of FIGS. 1 and 2, it is clear that a new sequence containing a C in this position must be a member of the HP04 group of strains; alternatively, either the presence of an A in this position or the absence of a C would indicate the new sequence belonged to one of the 5 remaining groups of strains (i.e., PC04, PC03, HP03-E, HP03-M, or HP03-L).

FIG. 2 shows a number of nucleotides in this category, i.e., nucleotides which are present in all members of only one of the six groups HP04, PC04, PC03, HP03-E, HP03-M, and HP03-L, and which when present may therefore be used to indicate the membership of the sequence containing that nucleotide in the particular group which the nucleotide designates. Specifically, FIG. 2 provides non-limiting examples of SNVs indicative of: HP04 (T at position 185; C at position 4160; T at position 14151; C at position 20885; and, T at position 27869); PC04 (T at position 17390); PC03 (T at position 3671; T at position 6456; A at position 22172;

A at position 22273; C at position 23310; T at position 23593; G at position 23718; T at position 23752; G at position 24171); and, T at position 25544); HP03-E (G at position 4220); and, HP03-L (T at position 27827).

Although the present invention contemplates the molecular markers described above as being particularly useful in identifying the stage of a SARS coronavirus strain or SARS-CoV-like strain, the invention is also directed to any SNV at any position that can be used to assist in the identification (staging) of a SARS-CoV or SARS-CoV-like sequence. For example, the present invention specifically contemplates markers which, while associated only with a particular group of SARS coronavirus strains, occur only in some members of that group. A strain containing a C at position 1727, for example, is from the data of FIGS. 1 and 2 a member of the HP03-L group; however, unlike the markers discussed above, because only some members of the HP03-L group have a C in this position, the absence of a C in this position is not conclusive as to group membership.

Also explicitly contemplated herein are molecular markers which occur in all members of multiple groups (e.g., the "EE" markers discussed below), as well as molecular markers which occur in some members of multiple groups (e.g., the occurrence of a T at position 9404), and markers which occur in some members of some groups and all members of others (e.g., a C at position 9479). As discussed above, the skilled artisan will recognize that the requirement for a suitable molecular marker useful for staging is satisfied by any insertion(s), deletion(s), SNV(s), or combination or combinations thereof which allow one of ordinary skill in the art to discriminate between the different groups of SARS-CoV and SARS-CoV-like strains. Thus, for example, a nucleotide that is present in all sequences of every group at a particular position is not suitable as a molecular marker, nor is a nucleotide that is found in at least some sequences in every group suitable as a marker.

Although the present invention contemplates molecular markers for identifying membership in one of the six groups of strains PC04, PC03, HP03-E, HP03-M, and HP03-L identified in Examples 1 and 2, the present invention is also directed to the identification of two other groups of strains referred to in these Examples, namely, the "early-early" and "earliest stage" groups of the Examples. Thus as described in Example 2, based on the data obtained for the PC04 and HP04 SARS-CoV-like and SARS-CoV strains, the HP03-E strains should more appropriately be characterized as the "relatively late stage of the early phase," with the PC04/HP04 groups together representing the "early-early" stage of the coronaviral evolution in humans. Markers suitable for identifying coronaviruses that are members of this "EE" group are shown in FIG. 2, and include, but are not limited to: A at position 2013; T at position 2606; T at position 2760; C at position 3567; G at position 3584; A at position 4108; G at position 5142; C at position 5811; T at position 6990; T at position 7137; C at position 7881; C at position 9335; A at position 10977; C at position 12119; G at position 13760; A at position 14117; C at position 14300; T at position 17374; G at position 19406; T at position 21907; G at position 21931; T at position 22874; C at position 22906; G at position 22930; G at position 23719; T at position 23785; C at position 25031; A at position 25341; G at position 25356; A at position 25693; G at position 26436; T at position 27425; A at position 27893; and, G at position 29022. Similarly, "earliest stage" coronviral sequences are those falling in the group containing the HP04, PC04, PC03, and HP03-E sequences. An example of an SNV marker suitable for identifying this group is the G at position 23823 shown under the "E" column in FIG. 2.

Figure 5:
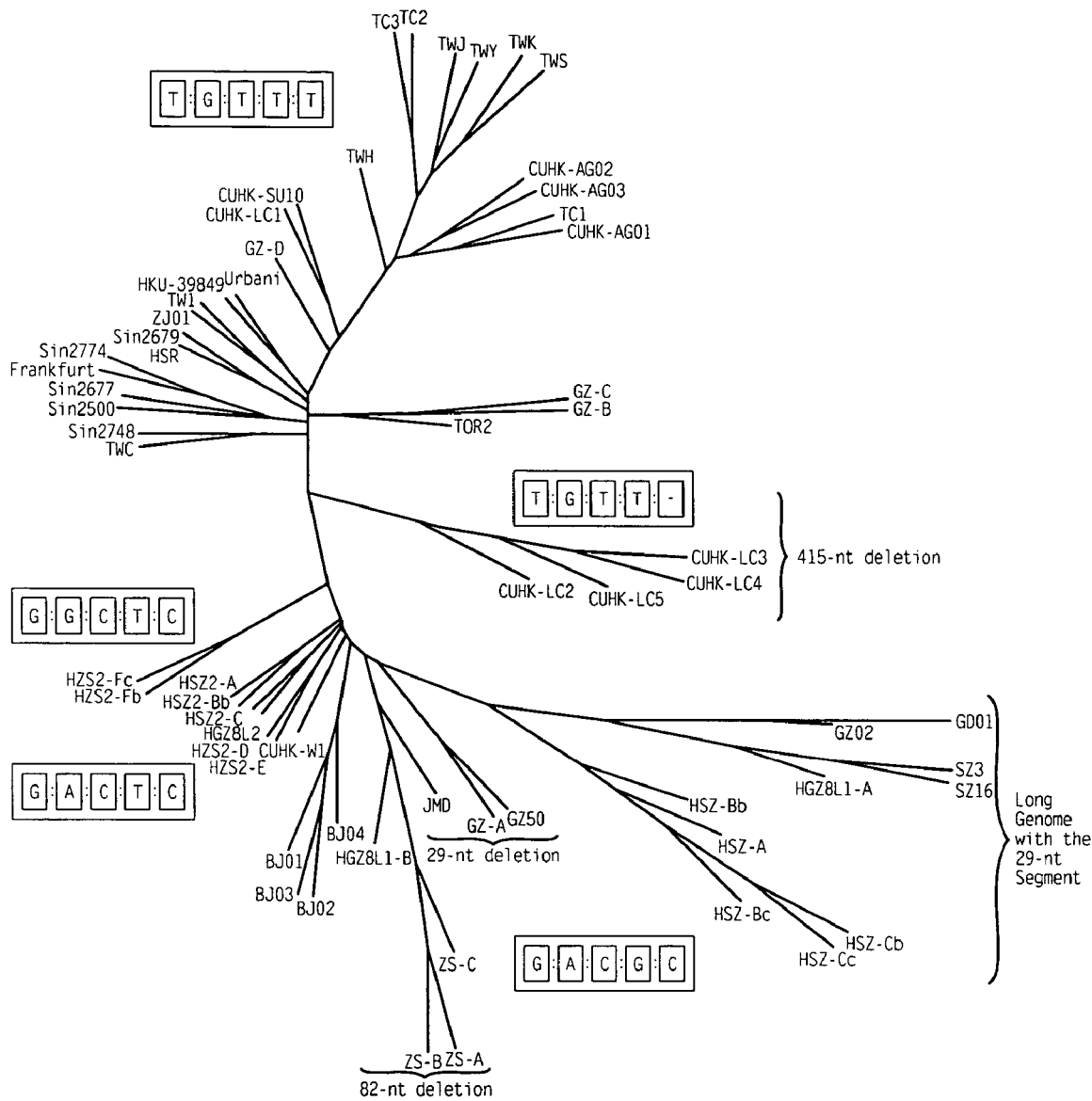
FIG. 5 shows the genotype clustering of SARS-CoV during the course of the epidemic. An unrooted phylogenetic tree of SARS-CoV was constructed from 61 human SARS-CoV genomes and two SARS-like coronavirus sequences from palm civets. Only those variant sequences (including deletions) that were present in at least two independent samples were used for tree construction. The map distance between individual sequences represents the extent of genotypic difference. The 5-nt motifs (see Example 1) that characterized the phylogenetically related genotypes are boxed. The genomic sequences are named in concordance with their GenBank nomenclature. Genotypes with major deletions are marked accordingly. All other genotypes (unmarked) had the 29-nt deletion. This 29-nt deletion was specifically marked for three genotypes, namely GZ-A, JMD, and GZ50, to indicate their special clustering within the early phase isolates.

As discussed in detail in Example 1, one set of SNVs of particular relevance in the present invention is the pentet of SNVs at positions 17564, 21721, 22222, 23823, and 27827 relative to the GZ02 reference sequence (SEQ ID NO:1) (see also FIG. 5). These positions are shown by the corresponding shaded columns in FIG. 1, and have the values shown in the Table 1 below for each of the groups HP04, PC04, PC03, HP03-E, HP03-M, and HP03-L (note that this table is based on the exclusion of the single G nucleotide occurring at position 17564 in the HP03-L strain QXC1, the single T nucleotide occurring at position 22222 in the HP03-E strain GZ-A, and, the unidentified nucleotide "N" occurring at position 23823 in the HSZ-A strain):

TABLE 1

| | Gene | | | | |
|---|---|---|---|---|---|
| | Nsp13 | S | S | S | Sars8a |
| | | | Nucleotide | | |
| | 17564 | 21721 | 22222 | 23823 | 27827 |
| AA | 5767 | 77 | 244 | 778 | 17 |
| AA Switch | E-D | D-G | T-I | D-Y | R-C |
| HP04 | G | A | C | G | C |
| PC04 | G | A | C | G | C |
| PC03 | G | A | C | G | C |
| HP03-E | G | A | C | G | C |
| HP03-M | G | A | C | T | C |
| HP03-L | T | G | T | T | T |

Thus as is shown in Table 1, the following pentets of SNVs at these positions are associated with each of the six SARS-CoV and SARS-CoV-like groups of strains shown above: GACGC (HP04, PC04, PC03, HP03-E); GACTC (HP03-M); and, TGTTT (HP03-L). Thus this pentet may be used as the basis for distinguishing these groups.

Alternatively, these positions may be used singly, or in various other combinations with each other or with other SNVs or insertions/deletions to classify SARS-CoV or SARS-CoV-like sequences. For example, the presence of a T at position 17564 is indicative of an HP03-L sequence, the presence of a T at position 23823 indicates membership in either the HP03-M or HP03-L groupings, etc.

The present invention also contemplates molecular markers within the region of the SARS-CoV or SARS-CoV-like coronavirus genome encoding the coronaviral Spike ("S") protein (SEQ ID NOS:4 and 5; the S protein is encoded in the GZ02 reference sequence (SEQ ID NO:1) at nucleotides 21492-25259)). This protein is a major component of the interaction between the coronavirus and the host, and mutations in this protein can therefore be expected to closely correlated with the infectivity of the coronavirus. Based on the data of FIGS. 1 and 2, as well as the preceding discussion, SNVs at positions 22570, 22927-22928, 22930 and 23316-23317 of the nucleotide sequence of the SARS coronaviral genome encoding the S protein may also have utility as specific markers for staging SARS-CoV and SARS-CoV-like strains.

Thus a C at position 22570 is characteristic of the HP04, PC04, and PC03 groups (see FIGS. 1 and 2), and therefore can be used to identify sequences falling into this set of strains. With regard to positions 22927-22928, this pair of SNVs represents a diad which is either AT (corresponding to Asn) for all SARS-affected individuals, or GA/AA (corresponding to Arg or Lys, i.e., to a positively-charged amino acid) for 4 of the 5 palm civet sequences determined (i.e., 22927-212928 is AT only for one palm civet sequence, the PC04 PC-227 sequence. See FIG. 1). This observation suggests that the change from the predominant palm civet GA/AA diad to the AT diad found in all human cases may be important to the successful propagation of the coronavirus in humans. Therefore, it is likely that this diad at 22927-22928 will be useful as a molecular marker for staging and, possibly, as a proxy for viral infectivity or success in a human host.

Similarly, at positions 23316-23317 there are only two observed diads: TT, which predominates in the "early-early" group PC04/HP04 (of the five sequences in this group, only one, that of the HP04 sequence GZ03-02 is GC instead of TT); and, GC which is present in all of the members of the PC03, HP03-E, HP03-M, and HP03-L groups. Thus, as for the 22927-22928 diad, the SNVs at 23316-23317 may be useful as a marker for staging or as a proxy for infectivity or survival/reproduction in a human host.

Further evidence for the utility of the diad pairs discussed above is provided by modeling studies suggesting their proximity to regions of the S protein of functional significance. Thus the present invention contemplates those nucleotide positions corresponding to important functional regions of one or more of the SARS-CoV or SARS-CoV-like proteins as being particularly useful, in light of their likely evolutionary constraints and/or selection pressures. For the S protein, structural modeling suggests that the amino acids in the region of amino acids 311-487 (corresponding to nucleotides 22422-22951 of the reference GZ02 sequence (SEQ ID NO:1)) are involved in the interaction of this protein with its receptor protein, ACE2. Modeling studies also suggest that another region of the S protein at amino acids 577-613 (corresponding to nucleotides 22422-22951) is important in the formation of trimers of the S protein. Thus in light of the contemplated importance of such functional regions in the present invention, the role of these two diad regions in staging is likely even apart from the other evidence for such utility given above.

Also with regard to the insertions/deletions and SNVs discussed above, although the present invention contemplates the use of any of the insertions/deletions and SNVs detailed in the preceding section, in the figures, or in the Examples, the skilled artisan will understand that some of these markers are expected to be of particular utility in the staging discussed in this section. For example, nucleotide changes that result in changed (non-synonymous) amino acids are expected to be under greater selection pressures than those which result in synonymous changes. Therefore it is likely that in some situations those nucleotide changes which result in non-synonymous amino acid changes will be of greater utility than those which cause synonymous changes. Similarly, nucleotide positions which encode amino acids of proteins of the coronavirus that are under selection pressure are also expected to be of potentially particular importance, as discussed above. Therefore, one of ordinary skill in the art of molecular marker selection would know to pick particular markers based not only on the extensive data provided herein, but also on the basis of such additional considerations as discussed.

After identifying particular insertion(s)/deletion(s) or SNV(s) that are useful as stage-specific molecular markers as described above, it is necessary to determine the presence or absence of such stage-specific markers in a SARS-CoV or SARS-CoV-like sequence of interest.

In this regard it will first be necessary to obtain the RNA sequence of interest, either directly from a patient as isolated SARS-CoV or SARS-CoV-like coronaviral RNA, or from cultures of cells infected with the SARS-CoV or SARS-CoV-like coronaviral strain from which the sequence of interest is to be obtained. Such purification and culturing methods are described elsewhere herein, and are routine to one of ordinary skill in the art.

After obtaining the RNA sequence of interest, an analysis can be conducted directly, using various RNA-based methods such as RT-PCR, or via an isolated cDNA produced using reverse transcriptase in conditions that are also well-known to the skilled artisan. In the latter case the cDNA may be analyzed by a variety of techniques discussed below.

In light of the above discussion, and in view of subsequent discussions of the proteins contemplated herein, it is therefore clear that the present invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably, culture medium represents less than about 30%, 20%, 10%, or 5% (by dry weight) of chemical precursors or non-protein of interest chemicals.

As discussed, one method of analysis contemplated herein is based on the direct analysis of the SARS-CoV or SARS-CoV-like coronaviral RNA using techniques including RT-PCR, while another method of analysis contemplated is an analysis based on PCR amplification of the isolated cDNA obtained from the RNA by reverse transcription.

In a PCR approach, oligonucleotide primers can be designed for use in PCR reactions to amplify corresponding DNA sequences from coronaviral cDNA. Methods for designing PCR primers or RT-PCR primers and PCR amplification are generally known in the art and are disclosed in Sambrook et al. (1989) Molecular Cloning. A Laboratory Manual (2d ed., Cold Spring Harbor Laboratory Press, Plainview, N.Y.). Known methods of PCR include, but are not limited to, methods using paired primers, nested primers, single specific primers, degenerate primers, gene-specific primers, vector-specific primers, partially-mismatched primers, and the like.

In PCR amplification, sense and anti-sense primers are hybridized to the sequence of interest, which is then amplified in an amplification reaction. Thus the present invention contemplates the use of various hybridization techniques for PCR reactions, as well as for other analytical methods known to one of ordinary skill.

In hybridization, all or part of a known nucleotide sequence is used as a probe that selectively hybridizes to other corresponding nucleotide sequences, e.g., a SARS-CoV or SARS-CoV-like coronaviral cDNA sequence. In general hybridization probes may be genomic DNA fragments, cDNA fragments, RNA fragments, or other oligonucleotides, as appropriate, and may be labeled with a detectable group such as $^{32}P$, or any other detectable marker. Thus, for example, probes for hybridization can be made by labeling synthetic oligonucleotides based on the coronaviral sequences of the invention. Methods for preparation of probes for hybridization and PCR are generally known in the art and are disclosed in Sambrook et al. (1989) Molecular Cloning: A Laboratory Manual (2d ed., Cold Spring Harbor Laboratory Press, Plainview, N.Y.).

An important parameter in hybridizations is the specificity of hybridization between the template and probes. Thus to achieve specific hybridization under a variety of conditions, such probes include sequences that are unique to the desired region of the coronaviral sequence, and are preferably at least about 10 nucleotides in length, and most preferably at least about 20 nucleotides in length. In PCR reactions, such probes may be used to amplify corresponding coronaviral sequence regions of interest, or as a diagnostic assay to determine the presence of particular sequence regions or individual nucleotides in a coronaviral template nucleotide sequence.

Hybridizations may be carried out under different conditions of stringency, for example under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 0.50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, with the critical factors being the ionic strength and temperature of the final wash solution. For DNA-DNA hybrids, the $T_m$ can be approximated from the equation of Meinkoth and Wahl (*Anal Biochem.* 138:267 (1984)): $T_m$=81.5° C.+16.6 (log M)+0.41(% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with about 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); and, low stringency conditions can utilize a hybridization and/or wash at 11, 12, 13, 14, 15, or 20° C. lower than the thermal melting point ($T_m$). Using the equation, hybridization and wash compositions, and desired $T_m$ those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, N.Y.); and Ausubel et al., eds. (1995) Current Protocols in Molecular Biology, Chapter 2 (Greene Publishing and Wiley-Interscience, New York). See also Sambrook et al. (1989) Molecular Cloning: A Laboratory Manual (2d ed., Cold Spring Harbor Laboratory Press, Plainview, N.Y.).

In order to determine the presence or absence of a molecular marker in the SARS-CoV or SARS-CoV-like sequence of interest it will additionally be necessary to determine the position of each nucleotide in the SARS-CoV or SARS-CoV-like sequence of interest relative to the positions of the stage-specific molecular markers described herein, which are themselves given relative to the GZ02 reference sequence (SEQ ID NO:1). In this regard the skilled artisan will understand that it will be necessary to align the SARS-CoV or SARS-CoV-like sequence of interest with the GZ02 reference sequence, using any of the well-known methods for such aligments, as are described elsewhere herein. Such an alignment will allow for the correlation of each position in the SARS-CoV or SARS-CoV-like sequence of interest with the corresponding position of the GZ02 sequence.

Although the present invention contemplates a variety of embodiments for detecting insertion(s)/deletion(s) or. SNV(s) of interest, one non-limiting embodiment of particular interest is a kit for analyzing these insertion(s)/deletion(s) or SNV(s). Thus based on the present disclosure, it is possible to specifically PCR-amplify regions of the SARS-CoV or SARS-CoV-like coronaviral genome that contain the insertion(s)/deletion(s) or SNV(s) of interest, and then analyze the resulting material by sequencing or other methods known to the skilled artisan. Example 3 provides for one such kit.

SARS Coronavirus Nucleotide Sequences

Another embodiment of the present invention is directed to the SARS coronaviral nucleotide sequences characteristic of the HP04, PC04, PC03, HP03-E, HP03-M, and HP03-L groups, and particularly to the nucleotide sequences characteristic of earliest stage SARS-CoV sequences (i.e., "early-early" and "early" stages), as well as closely-related SARS-CoV-like sequences. The availability of these sequences allows for the more complete study of the characteristics of the SARS-CoV or SARS-CoV-like coronaviruses during their evolution, and particularly during their earliest stages of their evolution, i.e., shortly after crossing the species barrier from its non-human source into humans. These earliest stages are of particular interest in the present invention, in light of the reduced virulence and infectivity of coronaviruses from these stages (e.g., the HP04 strains of 2002-2004; see Example 2).

Thus the present invention is directed to sequences characteristic of the HP04, PC04, PC03, HP03-E, HP03-M, and HP03-L groups. These sequences may be obtained by substituting the SNVs provided in FIG. 1 and the insertions/deletions provided elsewhere herein into the GZ02 reference sequence provided in SEQ ID NO:1. Thus, for example, with regard to SNVs, the sequence of GZ03-02 may be obtained by substituting into the GZ02 reference sequence a T nucleotide at position 185, a G nucleotide at position 508, a C nucleotide at position 1302, etc., as, determined by a comparison of the rows in FIG. 1 corresponding to the GZ02 and GZ03-02 sequences.

In one aspect, the present invention is directed to the exact sequences of the SARS-CoV and SARS-CoV-like coronaviral strains provided in FIG. 1, which may be obtained as described above. In another aspect, the present invention is directed to sequences related to these sequences either by % identity (synonymously, "% similarity"), by the presence of particular nucleotide(s), insertion(s), and/or deletion(s) at particular positions, or by all of these criteria.

With regard to % identity, the following terms are used to describe the sequence relationships between two or more nucleic acids, polynucleotides, or polypeptides: "reference sequence"; "comparison window"; "sequence identity"; "percentage of sequence identity"; and, "substantial identity." Note that this discussion is explicitly intended to encompass both the nucleotide sequences discussed in this section, and the polypeptides of the next section.

Thus as used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. Thus reference sequences of the present invention include SARS-CoV and SARS-CoV-like sequences, as well as subsets of these sequences, such as fragments or variants. By "fragment" is intended a portion of a nucleotide or amino acid sequence of the present invention; by "variants" is intended substantially similar sequences.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches. The present invention contemplates that analogous considerations will apply to polypeptide sequences.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) CABIOS 4:11-17; the local homology algorithm of Smith et al. (1981) Adv. Appl. Math. 2:482; the homology alignment algorithm of Needleman and Wunsch (1970) J. Mol. Biol. 48:443-453; the search-for-similarity-method of Pearson and Lipman (1988) Proc. Natl. Acad. Sci. 85:2444-2448; and, the algorithm of Karlin and Altschul (1990) Proc. Natl. Acad. Sci. USA 872264, modified as in Karlin and Altschul (1993) Proc. Natl. Acad. Sci. USA 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

For purposes of the present invention, comparison of nucleotide or protein sequences for determination of percent sequence identity to the promoter sequence or the anitpathogenic sequences disclosed herein is preferably made using the Clustal W program (Version 1.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

An additional indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) J. Mol. Biol. 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

With regard to the coronavirus nucletotide sequences of the invention, as discussed above such sequences are contemplated to include both the exact sequences presented herein (e.g., the strains in FIG. 1), and also sequences that are related to these sequences by the presence of particular nucleotide(s), insertion(s), or deletion(s) at particular positions, by % identity, or by all of these criteria.

Thus, in one embodiment, the present invention contemplates sequences that are fixed at one or more of the SNV positions of FIG. 1, and/or the insertion/deletions characterized elsewhere herein, but that are allowed to vary at all other non-fixed positions. While it is theoretically possible for such sequences to be fixed at only a single position, it is preferable to have a sequence fixed at multiple positions, in order to limit the size of the resulting genus of RNA species defined by this mixture of fixed and variable positions.

In this regard, one embodiment of the present invention is directed to genuses of sequences that have some or all of the hallmark characteristics of one of the groups of SARS-CoV and SARS-CoV-like strains of the invention (e.g., HP04, PC04, HP03-E, HP03-M, HP03-L, "EE," and "E," as defined elsewhere herein). Thus for example, the present invention contemplates a genus of SARS-CoV RNA sequences (and viruses resulting from assembly with such sequences, cells containing such viruses, etc., as described below) defined by having a base SARS-CoV RNA sequence such as the GZ02 reference sequence (SEQ ID NO:1) which has been modified at some or all of the appropriate positions so as to possess some or all of the characteristic SNVs, insertions, and deletions of a particular group or groups of strains of the invention.

Thus for example the appropriate positions in the GZ02 sequence may be modified to contain some or all of the nucleotides shown in FIG. 2 as being characteristic of the "early-early" ("EE") group of HP04/PC04. Thus the GZ02 sequence would have its usual sequence throughout its length, apart from one or more of the following positions, which would be assigned as follows: A at position 2013; T at position 2606; T at position 2760; C at position 3567; G at position-3584; A at position 4108; G at position 5142; C at position 5811; T at position 6990; T at position 7137; C at position 7881; C at position 9335; A at position 10977; C at position 12119; G at position 13760; A at position 14117; C at position 14300; T at position 17374; G at position 19406; T at position 21907; G at position 21931; T at position 22874; C at position 22906; G at position 22930; G at position 23719; T at position 23785; C at position 25031; A at position 25341; G at position 25356; A at position 25693; G at position 26436; T at position 27425; A at position 27893; and, G at position 29022.

Similarly, the pentet of positions provided in Table 1 may also be used as the basis for creating such genuses of sequences. Consider, for example, a GZ02 sequence with position 17564=T, 21721=G, 22222=T, 23823=T, and 27827=T. Solely with regard to these SNVs (i.e., omitting from consideration any insertions/deletions), this sequence possesses some of the hallmarks of an HP03-L sequence; i.e., any classification of this novel sequence based on a test of this pentet of nucleotides would indicate it to fall within the HP03-L category.

As mentioned above, although the nucleotide sequences of all of the groups defined herein are of interest, the earliest stage groups are of particular interest in light of the reduced virulence and infectivity of coronaviruses from these stages (e.g., the HP04 strains of 2002-2004; see Example 2). Thus the present invention is particularly directed to the nucleotide sequences characteristic of these groups, e.g., nucleotide sequences containing the insertions/delections/SNVs which are the hallmarks for the "early-early" (HP04/PC04) and/or "early" (HP04/PC04/PC03/HP03-E) stages. Thus sequences with, for example, the pentet shown in Table 1 as being characteristic of the "early" stages (position 17564=G, 21721=A, 22222=C, 23823=G, and 27827=C) and with the base sequence of, e.g., GZ02, are preferred. In this example, sequences with this pentet of fixed positions, and with the remaining positions those of, e.g., GZ02, but varied so that the sequence is of high % identity to the base GZ02 sequence, are particularly preferred, as described below.

The present invention contemplates that the embodiments given above may include both those embodiments in which the base sequence is unvaried except for the hallmark insertions/deletions/SNVs etc. introduced as described, and those embodiments in which those positions of the base sequence which are not fixed by the hallmark insertions/deletions/SNVs etc. are allowed to vary. In this latter case, the present invention contemplates as particularly useful those genuses of RNA species in which this variation of the base sequence is limited, i.e., to situations where the % identity between the novel sequence obtained by variation (and containing the fixed positions) is relatively high. Thus for example, the present invention contemplates situations in which the % identity between the non-fixed positions of the base sequence and the original base sequence is at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%. This % identity may be judged by an alignment over the entire length of the SARS-CoV or SARS-CoV-like RNA sequence (i.e., over the approximately 29,000 bases of the RNA sequence), or it may be determined over a shorter length of the sequence, for example, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, etc. (i.e., continuing by increments of 10 nucleotides up to the maximum length of the RNA). This % identity may be calculated by one of the algorithms described elsewhere herein; alternatively, it may be calculated as the number of different nucleotides per 100 nucleotides, such that a % identity of 99.9% would refer to no more than 1 nucleotide difference per 1000 nucleotides.

The present invention contemplates not only the sequences discussed above, but also the assembly of SARS-CoV or SARS-CoV-like coronaviruses containing these sequences, as well as vectors containing all or parts (fragments) of these sequences, as well as cells or animals containing these vectors or sequences. Methods for producing these constructs, cells, animals, etc., are well-known to the skilled artisan. For an example of assembly of a SARS coronavirus particle from a template cDNA see, e.g., Yount et al. (*Proc. Natl. Acad. Sci. U.S.A.* 100:12995 (2003)).

SARS Coronavirus Proteins

Another embodiment of the present invention is directed to amino acid sequences (synonymously, "polypeptides") encoded by the SARS-CoV or SARS-CoV-like nucleotide sequences of the present invention, as well as to vectors containing these amino acid-encoding nucleotide sequences, cells containing these vectors, and animals containing these nucleotide sequences, vectors, or cells.

Any of the proteins encoded by the SARS-CoV or SARS-CoV-like coronavirus are contemplated for use in the present invention. For SARS-CoV the following proteins have been identified: orf1ab, orf1a, S, sars3a, sars3b, E, M, sars6, sars7a, N, sars9b, and nsp1-16. The beginning and ending nucleotides for each of these proteins relative to the GZ02 reference sequence (SEQ ID NO:1) are as follows: orf1ab (265-13398,13398-21485); orf1a (265-13413); S (21492-25259); sars3a (25268-26092); sars3b (25689-26153); E (26117-26347); M (26398-27063); sars6 (26913-27265); sars7a (27273-27641); sars7b (27638-27772); N (27779-29417); sars9b (28159-28455); nsp1 (265-804); nsp2 (805-2718); nsp3 (2719-8484); nsp4 (8485-9984); nsp5 (9985-10902); nsp6 (10903-11772); nsp7 (11773-12021); nsp8 (12022-12615); nsp9 (12616-12954); nsp10(12955-13371); nsp 11(13372-13410); nsp12 (13372-13398, 13398-16166); nsp23 (16167-17969); nsp14 (17970-19550); nsp15 (19551-20588); and, nsp16 (920589-21482).

Analogous to the SARS-CoV and SARS-CoV-like nucleotide sequences of the invention discussed in the previous section, the amino acid sequences of the present invention include the exact amino acid sequences obtained by introducing the changes shown in FIG. 1 into the amino acid sequences encoded by the GZ02 reference sequence (SEQ ID NO:1). The amino acid sequences of the invention-also include amino acid sequences that are related to these exact sequences, but are different as a result of the introduction or removal of insertions/deletions/SNVs into the SARS-CoV or SARS-CoV-like coronaviral RNA that encodes these proteins, as well as additional changes added to other (non-fixed) positions which preserve a high % identity between the novel protein sequence and the sequence of the protein encoded in the original GZ02 reference sequence (i.e., the base amino acid sequence).

Thus for example, the present invention contemplates situations in which the % identity between the non-fixed positions of the novel amino acid sequence and the original (base) amino acid sequence is at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%. This % identity may be judged by an alignment over the entire length of the amino acid sequence, or it may be determined over a shorter length of the sequence, for example, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, etc. (i.e., continuing by increments of 10 amino acid residues up to the maximum length of the polypeptide of interest). This % identity may be calculated by one of the algorithms described elsewhere herein; alternatively, it may also be calculated as the number of different amino acids per 100 nucleotides, such that a % identity of 99% would refer to no more than 1 amino acid difference per 1000 nucleotides.

One protein of particular interest in the present invention is the S protein. As discussed previously, this protein mediates the interaction of the coronavirus with a host cellular receptor. Therefore this protein is of high importance in both the virulence and infectivity of a SARS coronavirus. Since the HP03-L stage is correlated with generally increased infectivity and virulence, particularly in relation to the HP04 and other earliest stage sequences, the present invention specifically contemplates S protein amino acid sequences that contain the hallmark amino acids that correspond to each of these stages. With regard to the pentet of Table 1, for example, 3 of the SNVs listed fall within the region of the nucleotide sequence encoding the S protein (21721, 22222, and 23823). Thus the present invention contemplates S proteins characteristic of either the HP04/PC04/PC03/HP03-E group (i.e., with residue 77=D, residue 244 T, and residue 778=D), the HP03-L group (i.e., with residue 77=G, residue 244=I, and residue 778=Y), or the (intermediate) HP03-M group (i.e., with residue 77=D, residue 244 T, and residue 778=Y). These proteins are fixed at these positions; at the remaining positions they may either be fixed (e.g., corresponding to the base sequence) or they may be varied so as to preserve a high % identity to the base sequence, as discussed above.

As discussed elsewhere herein, the SNVs at positions 22570, 22927-22928, 22930 and 23316-23317 of the nucleotide sequence of the SARS coronaviral genome encoding the S protein may be used as staging markers. In addition, the corresponding changes in amino acid as a result of mutations at these positions (namely 360 F→S☐479 N →R or K☐480 D→G☐609 A→L) may cause reduction in infectivity of SARS virus without affecting the immunogenicity of the S protein. Therefore the present invention also contemplates S protein sequences containing these amino acids in fixed positions, with the other positions either those of the base polypeptide sequence, or the base polypeptide sequence varied as described elsewhere herein (e.g., having a set % identity to the original base polypeptide sequence).

The amino acid positions of the S protein described above provide examples of what are referred to herein as "stage-specific amino acids," i.e., amino acids which serve to indicate stage-specificity in a manner analogous to the stage-specific nucleotide markers described previously. Thus a "stage-specific amino acid" is an amino acid that is encoded by the SARS-CoV or SARS-CoV-like genomes of some, but not all, of the groups of SARS-CoV or SARS-CoV-like strains presented elsewhere herein. Table 1 provides four examples of such stage-specific amino acids: the D amino acid residue corresponding to amino acid position 5767 of Orf1ab, which is specific for the HP03-L stage; the G amino acid residue corresponding to amino acid position 77 of the S protein, which is specific for the HP03-L stage; the I amino acid residue corresponding to amino acid position 244 of the S protein, which is specific for the HP03-L stage; and, the C amino acid residue corresponding to amino acid position 17 of the sars8a protein, which is specific for the HP03-L stage.

Also contemplated as an additional parameter affecting the allowed variation of a protein sequence is the activity of that sequence. That is, in addition to a requirement that the non-fixed positions of a sequence be varied only to the extent that the sequence retains a particular % identity to the original sequence, the present invention contemplates the possibility of an independent or additional requirement that the sequence be allowed to vary only to the extent that it retains the functionality of the original polypeptide, or, if the sequence in question is a fragment of the polypeptide, that it retains the activity characteristic of that original fragment.

Activity, as contemplated herein, will depend upon the specific protein or portion thereof, and will therefore be assayed by whatever method is commonly used for that particular protein or protein portion. For the S protein, for example, the skilled artisan will understand that appropriate assays include those measuring interaction with the host, or assays that reflect one component activity of the entire protein associated with a particular region of the protein of interest, e.g., interaction with ACE2, etc.

SARS Coronavirus Vaccines

Another embodiment of the present invention is directed to the development of vaccines for the SARS-CoV coronavirus. Thus as discussed elsewhere herein, and particularly in Example 2, the earliest stage SARS coronavirus strains characterized in the present invention are in general less virulent or contagious than are later stage strains of the SARS coronavirus. This observation suggests the particularly great utility, of earliest stage coronavirus in the development of vaccines for the diease. To date, however, vaccine candidates have in general been developed from later stage SARS coronaviral sequences, which are both more readily available and easier to grow than earliest stage strains. Thus one aspect of the present-invention involves the production of vaccines based on these earliest strains, including whole-virus vaccines, and vaccines based on components of these strains, e.g., the S proteins characteristic of these earliest stages of the coronavirus.

As stated above, there are a number of advantages to the use of earliest stage SARS coronaviral strains, or components thereof, in the development of vaccines. First, although middle- or late-stage SARS coronaviral strains are easy to culture, their high virulence and infectivity constitute a high risk for their safe use. In contrast, earliest stage strains, although difficult to culture, are less virulent and contagious, and therefore have an advantageous safety profile. In addition, studies have suggested that the immunity elicited by these earliest stage strains is likely sufficient to neutralize later-occurring strains.

The present invention contemplates vaccines based on whole-coronavirus vaccines, including live-attenuated and inactivated coronavirus vaccines. The present invention also contemplates vaccines based on various components of the virus, e.g., based on the S protein. Also contemplated are vaccines-based on antibodies against the coronavirus, or component or components thereof (see, e.g., ter Meulen et al., *Lancet* 363:2139 (2004)). Particularly contemplated in the present invention are those vaccines based on earliest stage coronaviruses, or components thereof.

In the whole-coronavirus vaccines of the present invention, the coronavirus is mixed with the appropriate adjuvant, diluents, and carriers. Physiologically acceptable media that can be used include, but are not limited to, appropriate isoosmotic solutions and phosphate buffers. Vaccines based on components of the coronavirus, such as those based on the earliest stage S protein sequence, as described in the preceding section, are particularly contemplated herein. The construction of a vector containing the nucleotide sequence encoding an earliest phase S protein (i.e., an S protein with residue 77=D, residue 244 T, and residue 778=D; see, e.g., Table 1 above) is described elsewhere herein and would be known to one of ordinary skill in the art. See also Bukreyev et al., *Lancet* 363:2122 (2004).

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., Immunology, Second Ed., 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*.

Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). In a specific embodiment, infra, the vaccine of the present invention is administered intramuscularly in alum. Alternatively, the vaccine of the present invention can be administered subcutaneously, intradermally, intraperitoneally, or via other acceptable vaccine administration routes.

A vaccine formulation may be administered to a subject per se or in the form of a pharmaceutical or therapeutic composition. Pharmaceutical compositions comprising the adjuvant of the invention and an antigen may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen. For purposes of this application, "physiologically acceptable carrier" encompasses carriers that are acceptable for human or animal use without relatively harmful side effects (relative to the condition being treated), as well as diluents, excipients or auxiliaries that are likewise acceptable. Systemic formulations include those designed for administration by injection, e.g. subcutaneous, intradermal, intramuscular or intraperitoneal injection. For injection, the vaccine preparations may be formulated in aqueous solutions, preferably in physiologically compatible buffers such as Hanks's solution, Ringer's solution, phosphate buffered saline, or any other physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

Determination of an effective amount of the vaccine formulation for administration is well within the capabilities of those skilled in the art. An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the vaccine formulations of the invention may be administered in about 1 to 3 doses for a 1-36 week period. Preferably, 1 or 2 doses are administered, at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 pg. Suitable dose range will vary with the route of injection and the size of the patient, but will typically range from about 0.1 mL to about 5 mL.

Example 1

Molecular Evolution of the SARS Coronavirus During the Course of the 2002-2003 SARS Epidemic Severe acute respiratory syndrome (SARS) first emerged in Guangdong Province, China. Subsequently, the SARS coronavirus (SARS-CoV) was identified as the causative agent (Fouchier et al., *Nature* 423:240 (2003); Ksiazek et al, *N. Engl. J Med.* 348:1953 (2003); Drosten et al., *N. Engl. J. Med.* 348:1967 (2003); Rota et al., *Science* 300:1394 (2003); Marra et al., *Science* 300:1399 (2003)). It remains a challenge to establish the relationship between observed genomic variations and the biology of SARS (Rota et al., *Science* 300:1394 (2003); Marra et al., *Science* 300:1399 (2003); Vogel, Science 300:1062 (2003); Ruan et al., *Lancet* 361:1779 (2003); Guan et al., *Science* 302:276 (2003)). Recent molecular epidemiological studies have identified characteristic variant sequences in SARS-CoV for tracking disease transmission (Ruan et al., *Lancet* 361:1779 (2003); Tsui et al., *N. Engl. J. Med.* 349:187 (2003); Chim et al., *Lancet* 362:1807 (2003); Chiu et al., *N. Engl. J. Med.* 349:1875(2003)). Evidence suggests that SARS-CoV emerged from nonhuman sources (Guan et al., *Science* 302:276 (2003); Rest and Mindell, *Infect. Genet. Evol.* 3:219 (2003)). In this study, epidemiological and genetic evidence for viral adaptation to human beings was obtained through molecular investigations of the characteristic viral lineages found in China (Zhong et al., *Lancet* 362:1353 (2003)).

On the basis of epidemiological investigations, the course of the 2002-2003 epidemic was divided into early ("HP03-E"), middle ("HP03-M"), and late ("HP03-L") phases. The early phase is defined as the period from the first emergence of SARS to the first documented superspreader event (SSE) (Zhong et al., *Lancet* 362:1353 (2003)). The middle phase refers to the ensuing events up to the first cluster of SARS cases in hotel M in Hong Kong (Tsang et al., *N. Engl. J. Med.* 348:1977 (2003)). Cases following this cluster fall into the late phase.

The early phase was initially characterized by a series of seemingly independent cases. Eleven index cases that had arisen locally in the absence of any contact history were identified from different geographical locations within Guangdong Province. This phenomenon was observed from the retrospectively identified SARS index patient from the city of Foshan (onset date, 16 Nov. 2002) (Zhong et al., Lancet 362:1353 (2003)) through to an index patient from the city of Dongguan (onset date, 10 Mar. 2003). All of these cases were confined to regions directly west of Guangzhou, the capital city of Guangdong Province, and to the city of Shenzhen in the south, with no cases being reported to the north or east of Guangzhou. This region, the Pearl River Delta, has enjoyed rapid economic development since the late 1970s, leading to the adoption of culinary habits requiring exotic animals. Seven of these 11 cases had documented contact with wild animals. In contrast to the apparently independent seeding of the earliest cases, the rest of the epidemic was characterized by SSEs and clusters of cases that were epidemiologically linked (Chim et al., Lancet 362:1807 (2003); Chiu et al., N. Engl. J. Med. 349:1875 (2003); Zhong et al., Lancet 362:1353 (2003); Tsang et al., N. Engl. J. Med. 348:1977 (2003); Lee et al., N. Engl. J. Med. 348:1986 (2003)).

The first major SARS outbreak occurred in a hospital, HZS-2, in the city of Guangzhou, beginning on 31 Jan. 2003 where an SSE was identified to be associated with more than 130 primary and secondary infections, of which 106 were hospital-acquired cases. Doctor A, a nephrologist who worked in this hospital, visited Hong Kong and stayed in Hotel M on 21 Feb. 2003. Other visitors to the hotel later became infected with SARS-CoV (Zhong et al., Lancet 362:1353 (2003); Tsang et al., N. Engl. J. Med. 348:1977 (2003)). This led to the transmission of SARS to Vietnam, Canada, Singapore, and the United States (Centers for Disease Control and Prevention, Morb. Mortal. Wkly. Rep. 52, 241 (2003)), with two further SSEs in Hong Kong, each resulting in the virus being transmitted to >100 contacts (Chim et al., Lancet 362:1807 (2003); Lee et al., N. Engl. J. Med. 348:1986 (2003)).

Genomic sequence data for SARS-CoV were largely derived from isolates linked to the Hotel M cluster (Vogel, Science 300:1062 (2003)), hence they were predominantly from the late phase of the epidemic. 29 SARS-CoV genomic sequences were determined from 22 patients from Guangdong Province with disease onset dates in all three phases of the epidemic, and from two patients from the late phase in Hong Kong. To eliminate mutational noise, it was assumed that sequence variants associated with common ancestry, but not arising in cell culture, should be seen in multiple isolates (Ruan et al., Lancet 361:1779 (2003)). Meanwhile, critical genomic variations or complete genome sequences of certain virus isolates were verified by sequencing the reverse transcription polymerase chain reaction (RT-PCR) products derived directly from patient specimens. The genomic sequences obtained were compared with 32 human SARS-CoV sequences and two SARS-like coronavirus sequences from Himalayan palm civets (Paguma larvata) available at GenBank (see the website ncbi.nlm.nih.gov/entrez). Thus the following 63 sequences were compared: SZ3, SZ16, GZ02 (SEQ ID NO:1), GD01, HGZ8L1-A, HSZ-Cc, HSZ-A, HSZ-Bb, HSZ-Cb, HSZ-Bc, GZ50, GZ-A, JMD, HGZ8L1-B, ZS-A, ZS-B, ZS-C, BJ04, BJ03, BJ02, BJ01, CUHK-W1, HZS2-D, HZS2-E, HZS2-C, HGZ8L2, HZS2-Bb, HZS2-A, HZS2-Fc, HZS2-Fb, TWC, Sin2679, ZJ01, HSR, TW1, HKU-39849, GZ-D, Urbani, Sin2748, Sin2677, Sin2500, Frankfurt, Sin2774, CUHK-Su10, CUHK-LC1, CUHK-AG01, CUHK-AGO 2, CUHK-AGO3, TWH, TC1, TWY, TWS, TWK, TWJ, TC3, TC2, GZ-B, GZ-C, TOR2, CUHK-LC2, CUHK-LC3, CUHK-LC4, and CUHK-LC5.

Only two major genotypes predominated during the early phase of the epidemic. Five isolates were found to contain a 29-nucleotide (nt) sequence that is absent in most of the publicly available SARS-CoV sequences, whereas another four isolates showed a previously unreported 82-nt deletion in the same region of the genome, Orf8 (Snijder et. al., J. Mol. Biol 331, 991 (2003)) (see FIGS. 3 and 4). The former sequence is represented by the GZ02 isolate (SEQ ID NO:1), and is used as the reference for annotation throughout this study. All of the isolates exhibiting this sequence (GZ02, HGZ8L1-A, HSZ-A, HSZ-B, and HSZ-C; see FIG. 5) were obtained from patients with contact histories traceable to some of the earliest independent cases in Guangzhou and were not detected in any of the later isolates. It is noteworthy that this sequence with the 29-nt segment is identical to the genomic sequence of coronaviruses isolated from animals in a Shenzhen live animal market (Guan et al., Science 302:276 (2003)).

Three of the SARS-CoV genome sequences (ZS-A, ZS-B, and ZS-C; see FIG. 5) with the 82-nt deletion were obtained from samples of very early cases from Zhongshan city. This 82-nt deletion was further confirmed by RT-PCR directly on an additional stool sample. A sequence with an identical 82-nt deletion has also been observed in coronaviruses isolated from farmed civets in Hubei Province, China. Specifically, SARS-like coronaviruses were isolated from palm civets farmed domestically in Hubei Province, China, by Hu et al. at the Wuhan Institute of Virology, Chinese Academy of Sciences. Partial genome sequencing revealed an 82-nt deletion within the Orf8 region, which is identical to that found in human SARS-CoV isolates from the early patients of Zhongshan, Guangdong Province, China. Contamination can be ruled out because no human SARS-CoV isolate with the 82-nt deletion has ever been found in that institute or has been-isolated in that region of China. It is thus interesting to note that both sequences of the early phase were identified from other mammalian hosts. They provided a link to support the notion that early human infection of SARS-CoV may have originated from wild animals (Guan et al., Science 302:276 (2003); Rest and Mindell, Infect. Genet. Evol. 3:219 (2003)).

In contrast to the early phase, a SARS-CoV sequence with the 29-nt deletion was observed during the middle phase that dominated the viral population for the rest of the epidemic (Rota et al., Science 300:1394 (2003); Marra et al., Science 300:1399 (2003); Ruan et al., Lancet 361:1779 (2003)). Although this shift in genome size might be due to chance, deletion events appeared to be overrepresented in the Orf8 region. A fourth sequence with the 82-nt deletion was obtained from a Guangzhou patient (HGZ8L 1-B), who was infected in the same ward as one of the patients where the longest sequence was obtained (HGZ8L 1-A) (see above). Furthermore, a lung biopsy of a patient from the middle phase was found to contain two SARS-CoV genotypes, with the 29-nt and the 82-nt deletions, respectively. Remarkably, another genotype with a 415-nt deletion resulting in the loss of the whole Orf8 region was isolated and confirmed in two Hong Kong patients with disease onset from mid-May 2003 (see FIGS. 3 and 5). Specifically, the SARS-CoV sequence with the 415-nt deletion (CUHK-LC2, CUHK-LC3, CUHK-LC4, and CUHK-LC5) was obtained from two SARS patients whose disease was linked to a late cluster of SARS cases in Hong Kong. Both patients had disease onset in mid-May 2003. The CUHK-LC2 sequence was initially obtained from the culture isolate of a throat wash specimen of an infected hospital health care worker and was later confirmed from the same specimen directly. CUHK-LC3, CUHK-LC4, and CUHK-LC5 were obtained from three different nasal swab specimens both directly and from the culture supernatants of an elderly patient who acquired SARS in the same hospital.

Because the majority of deletions observed in the SARS-CoV genome occurred in the Orf8 region with no apparent effect on the survival of the virus, it is tempting to suggest that this region is either noncoding or coding for a functionally unimportant putative protein. On the other hand, it is interesting to note that antiparallel reverse symmetrical sequences were readily predicted around the deletion sites (see FIG. 3), which might account for the high deletion rates in this region. Whether such hairpin structures actually play a role in regulating either RNA replication or mRNA transcription in SARS-CoV is a subject for future studies.

Besides the deletion variants, 299 single-nucleotide variations (SNVs) were detected among the 63 sequences. Eighty-five of these variant loci were seen in more than one of the human SARS-CoV sequences. Among them, 52 were predicted to cause amino acid changes (nonsynonymous variations). When the epidemiologically determined transmission paths and SNV genotype data are combined, markers for genotypes characteristic of different lineages are evident (see FIG. 5).

Viruses of the early phase have the characteristic motif of G:A:C:G:C at the GZ02 reference nucleotide residues 17,564,21,721, 22,222, 23,823, and 27,827, with the bold SNVs matching the C:G:C:C motif identified previously (Ruan et al., *Lancet* 361:1779 (2003)) (see FIG. 5). This motifis shared by almost all early Guangzhou and Zhongshan isolates together with the animal SARS-like coronavirus isolates (SZ3 and SZ16) (Guan et al., *Science* 276 (2003)). Along with the disappearance of viruses containing the 29-nt segment, the middle phase of the epidemic was characterized by the occurrence of genotypes with the G:A:C:T:C motif (see FIG. 5). All of the middle-phase genotypes demonstrate this common motif but can be further classified into two variant groups on the basis of other SNVs. One group was represented by the isolates related to the Hospital HZS-2 outbreak (HZS2-A, HZS2-B, HZS2-C, HZS2-D, HZS2-E, and HGZ8L-2). The other group was represented by the Hong Kong CUHK-W1 isolate that originated from Shenzhen (Tsui et al., *N. Engl. J. Med.* 349:187 (2003)) together with the early Beijing isolates BJ01, BJ02, and BJ03, traceable to Guangdong. The transition between the characteristic motifs of the early and middle phases represented a G→T transversion at nucleotide residue 23,823 and is predicted to cause an Asp→Tyr change at amino acid residue 778 of the spike (S) protein (see FIG. 1).

An additional A→G transition at nucleotide 21,721 (see FIG. 5) was identified in one isolate from a secondarily infected patient from Hospital HZS-2 with disease onset on 7 Feb. 2003 (HZS2-Fc) (see FIG. 5). This sequence was additionally confirmed by direct sequencing of the RT-PCR product from an oropharyngeal swab of this patient (HZS2-Fb). This mutation is predicted to cause an $Asp^{77}$→Gly amino acid switch in the S protein (FIG. S4), and the G:G:C:T:C motif is so far genotypically the closest sequence to that of the Hotel M outbreak (T:G:T:T:T) (see FIG. 5) (Tsang et al., *N. Engl. J. Med.* 348:1977 (2003)). Epidemiologically, this patient is potentially linked to the Hotel M outbreak through her contact with Doctor A during the first 3 days of illness. Thus, Doctor A was possibly infected with this viral variant.

Additionally, one G→T transversion and two C→T transitions at nucleotide residues 17,564, 22,222, and 27,827 are observed in the Hotel M-associated SARS-CoV genotypes (see FIG. 5). These SNVs are predicted to cause amino acid switches in the nonstructural polyprotein ($Glu^{1389}$→Asp), the S protein ($Thr^{244}$→Ile), and Orf8a($Arg^{17}$→Cys), respectively. This T:G:T:T:T motif is shared by the sequences of all isolates infected from and after the Hotel M cluster (Ruan et al., *Lancet* 361:1779 (2003)), including the Hong Kong Amoy Gardens isolates(Chim et al., *Lancet* 362:1807 (2003)) and the more recent isolates from Zhejiang (ZJ01), Taiwan (Chiu et al., *N. Engl. J. Med.* 349:1875 (2003)), and Guangdong (GZ-B, GZ-C, and GZ-D) (see FIG. 5). This motif is also conserved in the late 415-nt deletion variant in Hong Kong with the exception of nucleotide 27,827, which falls within the deleted segment discussed previously. Thus, surprisingly few genotypes predominated during the late phase of the epidemic.

The characteristically high mutation rate of RNA viruses (Lai and Holmes, in *Fields Virology*, Knipe and Howley, Eds. (Lippincott Williams & Wilkins, New York, ed. 4, 2001), chap. 35) may give rise to strains with increased virulence (Brown et al., *Proc. Natl. Acad. Sci. U.S.A.* 98, 6883 (2001)) that can either escape host defenses (Seo et al., *Nature Med.* 8:950 (2002)) or change their tissue tropism (Rasschaert et al., *J. Gen. Virol.* 71:2599 (1990)). In this regard, it was observed that the neutral mutation rate for SARS-CoV during this epidemic was almost constant, and was estimated to be $8.26\times10^{-6}$ ($\pm2.16\times10^{-6}$) $nt^{-1}$ $day^{-1}$. This is similar to the values obtained for known RNA viruses and is about one-third that for the human immunodeficiency virus (L1 et al., *Mol. Biol. Evol.* 5:313 (1988); Drake and Holland, *Proc. Natl. Acad. Sci. U.S.A.* 96:13910 (1999)). In contrast to the constant rate of synonymous variations, the nonsynonymous mutation rates were variable for the three epidemic phases. The predicted domains of the S protein responsible for viral host receptor recognition or internalization (Luo et al., *J. Virol.* 73:8152-(1999)) were those that underwent the most extensive amino acid substitutions.

Between the coronavirus sequences of the palm civets (SZ3 or SZ16) and each of the human SARS-CoV sequences, the ratios of the rates of nonsynonymous to synonymous changes (Ka/Ks) for the S gene sequences were always greater than 1, indicating an overall positive selection pressure. However, pairwise analysis of the Ka/Ks for the genotypes in each epidemic group shows that the average Ka/Ks for the early phase was significantly larger than that for the middle phase, which in turn was significantly larger than the ratio for the late phase, which in fact was significantly less than 1. These data indicate that the S gene showed the strongest positive selection pressures initially, with subsequent purifying selections and eventual stabilization. For Orf1a, a pattern similar to that for the S gene was observed. In contrast, Orf1b (nt coordinate: 13,398 to 21,485) seems to be undergoing purifying selection during the whole course of the epidemic. Indeed, it is the most conserved genomic region of SARS-CoV (Ruan et al., *Lancet* 361:1779 (2003)).

The present analysis thus suggests that adaptive pressures operated on the SARS-CoV genome but stabilized during the late phase of the epidemic with the emergence of a predominant genotype. Alternatively, sampling bias for cases related to SSEs (Bush et al., *Proc. Natl. Acad. Sci. U.S.A.* 97:6974 (2000)) may distort the data. Such strategies may, however, be justifiable from a public health perspective, as the viral genotypes associated with the SSEs are the most epidemiologically important. To explore the possibility of bias, the date for the most recent common ancestor of the samples available was estimated. On the basis of the observed neutral mutation rate, this date was estimated to lie in mid-November 2002 (95% confidence interval: early June 2002 and late December 2002). This result is consistent with the onset date of 16 Nov. 2002 for the earliest index patient from Foshan (Zhong et al., *Lancet* 362:1353 (2003)) and supports the finding that the early, middle, and late phase genotypes represent different stages of evolution of the same viral lineage. This is further evident from the remarkable correlation between the molecular clustering and epidemiological grouping of the genotypes throughout the epidemic (see FIG. 5).

In tracing the molecular evolution of SARS-CoV in China, it was observed that the epidemic started and ended with deletion events, together with a progressive slowing of the nonsynonymous mutation rates and a common genotype that predominated during the latter part of the epidemic. The mechanistic explanation for the selective adaptation and purification processes that led to such genomic evolutionary changes in SARS-CoV requires further work (Ewald, *J. Urban Health* 75-480 (1998)). Nonetheless, this study has provided valuable clues to aid further investigation of this remarkable evolutionary tale.

In summary, then, in this Example sixty-one SARS coronavirus genomic sequences derived from the early, middle, and late phases of the severe acute respiratory syndrome (SARS) epidemic were analyzed together with two viral sequences from palm civets. Genotypes characteristic of each phase were discovered, and the earliest genotypes were similar to the animal SARS-like coronaviruses. Major deletions were observed in the Orf8 region of the genome, both at the start and the end of the epidemic. The neutral mutation rate of the viral genome was constant but the amino acid substitution rate of the coding sequences slowed during the course of the epidemic. The spike protein showed the strongest initial responses to positive selection pressures, followed by subsequent purifying selection and eventual stabilization.

Materials and Methods

A. Epidemiological Investigations

Official epidemiological records of the Guangdong Center for Disease Control and Prevention (GDCDCP), which represented an aggregate of the regular SARS epidemiology reports submitted by the local Centers for Disease Control and Prevention of individual cities, were reviewed. The contact and clinical histories of all of the early seemingly independent index cases and several key cases (e.g. HZS2-F) were reconfirmed either by review of hospital patient records or direct interview with the patients and/or the physicians-in-charge. In particular, eleven index cases from seven cities located in the Pearl River Delta region of Guangdong Province (FIG. 1 and FIG. S1), which occurred prior to the first superspreader event of a Guangzhou hospital, HZS-2, were investigated in detail.

The majority of the specimens were collected by the virologists of GDCDCP, with the remaining samples collected by the staffs of local hospital or Guangzhou Center for Disease Control and Prevention.

B. Sequencing Strategy and Procedures

Viral RNA templates were isolated either from the culture supernatants of VeroE6 cells that showed cytopathic effects or directly from patients' specimens of SARS cases (including serum, stool, oropharyngeal swabs, nasal pharyngeal aspirates or autopsy lung tissues). RNA was extracted with the QIAamp viral RNA mini kit (Qiagen, Valencia, Calif., USA) or TRIZOL Reagent (GIBCOBRL). The double-strand cDNA was synthesized with the SuperScript II cDNA system (Invitrogen, Carlsbad, Calif., USA) or RNA PCR Kit (AMV) Ver.2.1 (Takara, Dalian China). To amplify the genomic sequences of the SARS-CoV, 53 sets of nested primers were designed based on the TOR2 sequence. The nested PCR fragments were directly sequenced in both forward and reverse directions on the ABI-3700 DNA sequencer (Applied Biosystems, Foster City, Calif., USA) with 2- to 4-fold redundancy. For GZ02, PCR primers were designed to cover the whole genome in every 1 kb interval with 200 bp overlap with the adjacent fragment based on the TOR2 sequence. PCR products were sequenced using ABI BigDye Terminator Cycle Sequencing Kit on ABI-377. All of the nucleotide sequence variations of GZ02, which differ from that of the human SARS-CoV sequences available at GenBank as of June 2003, in particular, TOR2 and GZ01 (the sequence of an independent viral isolate from the same patient as GZ02 and currently renamed as GD01) sequences (including the 29-bp segment), were re-sequenced from RNA extractions from the same lung tissue specimen of that patient and the 5' end sequence was completed. The PHRED/PHRAP/CONSED software, (University of Washington, Seattle, Wash., USA; available at the website phred.org) was used for base calling, assembly, and editing. The assembled genome sequence was checked manually for accuracy and the regions with poor quality were re-sequenced. For data analysis, the nucleotide coordinate of GZ02 (SEQ ID NO:1) was used as a reference.

C. Sequence Alignments

Sequence alignments were generated using CLUSTALW 1.83 with the Gonnet nuclear acid comparison matrix for the sequences analyzed.

Example 2

Cross-host Evolution of SARS Coronavirus in Palm Civet and Humans

The coronaviruses isolated from a number of Himalayan palm civets (*Paguma larvata*) and a raccoon dog (*Nyctereutes procyonoides*) at a Shenzhen food market during the severe acute respiratory syndrome (SARS) epidemic of 2003 (April) were named SARS coronavirus-like coronaviruses ("SARS-CoV-like" coronaviruses) when it was observed that they displayed 99.8% sequence homology with the human SARS-CoV (Guan et al., *Science* 302:276 (2003)). However, recent analyses of palm civet and other wild animals in the Guangzhou food market of late 2003 suggested that in these animals SARS-CoV-like coronaviral loads and sequence variations were greater than those observed previously in these animals.

The molecular investigation of the characteristic viral lineages of the 2002-2003 Chinese SARS epidemic discussed in Example 1 above provides epidemiological and genetic evidence for viral adaptation to human beings. Although an animal origin of the infection has been suggested, neither direct evidence nor clues about the molecular mechanisms that enable the virus to switch hosts have been available. In this Example, the sequence data of viruses obtained from recent (2003-2004) human and palm civet infections were used to delineate the characteristics of the cross-host evolution of the SARS-CoV over a short period of time. This is an essential step for understanding the genetic process of adaptation of the SARS coronavirus to humans, and is critically important to developing procedures for treating and ultimately preventing SARS.

Between Dec. 16, 2003 and Jan. 8, 2004, a total of 4 patients were hospitalized in the city of Guangzhou, Guangdong Province, China, with flu-like syndromes later diagnosed as confirmed SARS. No patient had contact with other SARS cases nor had contact with each other. However, all of these patients had direct contact history with wild animals (palm civets and house rat) in geographically restricted areas. They all had very mild symptoms, much less severe than those displayed by most patients during the previous epidemic. None of their close contacts were infected. In summary, these four cases occurred independently and seemed to have little infectivity towards other human beings.

Specimens were collected during the 2003-2004 outbreak in Guangzhou, with nearly complete SARS-CoV viral genome sequences from the first and the second of the four human patients. Related SARS-CoV-like coronaviruses were similarly obtained from two palm civets of Guangzhou food market and one sample from an animal cage at a restaurant in the area (Restaurant TDL).

The viral sequences of the 2003-2004 outbreak were compared with those identified from the 2002-2003 epidemic, as shown in FIG. 6. All of them were characterized as bearing the 29 bp segment marker in orf8a as in the viruses of PC03 and the Guangzhou lineage of HP03E, e.g., GZ02 (See Example 1: see also Chinese SARS Molecular Epidemiology Consortium, *Science* 303:1666 (2004)). A total of 202 single nucleotide variations (SNVs) with multiple occurrences were identified. Beside 2 non-coding variations and 72 synonymous variations, 89 of the remaining 128 nonsynonymous mutations may cause drastic amino acid changes in the viral proteins.

The phylogenetic analysis of these viral sequences demonstrated that the genomes of the SCoV from HP04 were almost identical to those of the SARS-CoV-like coronaviruses from PC04 (see FIG. 6). There were 33 SNVs detected among the viruses from PC04 and HP04, which accounts for only 0.11% of the viral genome. In contrast, a total of 77 SNVs was detected among the SCoV genomic sequences of HP03E and PC03, accounting for nearly 0.26% of the the viral genome. Remarkably, no SNV distinguishes the genotype of SCoV from that of the SCoV-like viruses, although 17 out of the 202 SNVs were only observed in animals. Thus, structurally, there is little difference to distinguish these two viruses and functionally, concerning the direct animal contact history of the current patients, it is likely that the same virus can infect both palm civet and human. SARS is indeed a zoonotic disease.

Comparing the genomic sequence variations between PC03 and PC04, the difference was significant. There were 82 SNVs detected among the viruses from palm civets, which accounts for nearly 0.28% of the viral genome. This variation ratio is even higher than that observed between PC03 and HP03-E (see above). To explore further this remarkable observation, the phylogeny of the three most significantly variable protein coding sequences (CDSs), Spike (S), sars3a and nsp3 among palm civets and human patients of the two epidemic was analyzed using the maximum likelihood estimation (Yang, *Mol. Biol. Evol.* 15:568 (1998)) (see FIGS. 7A-C).

Figure 7A:
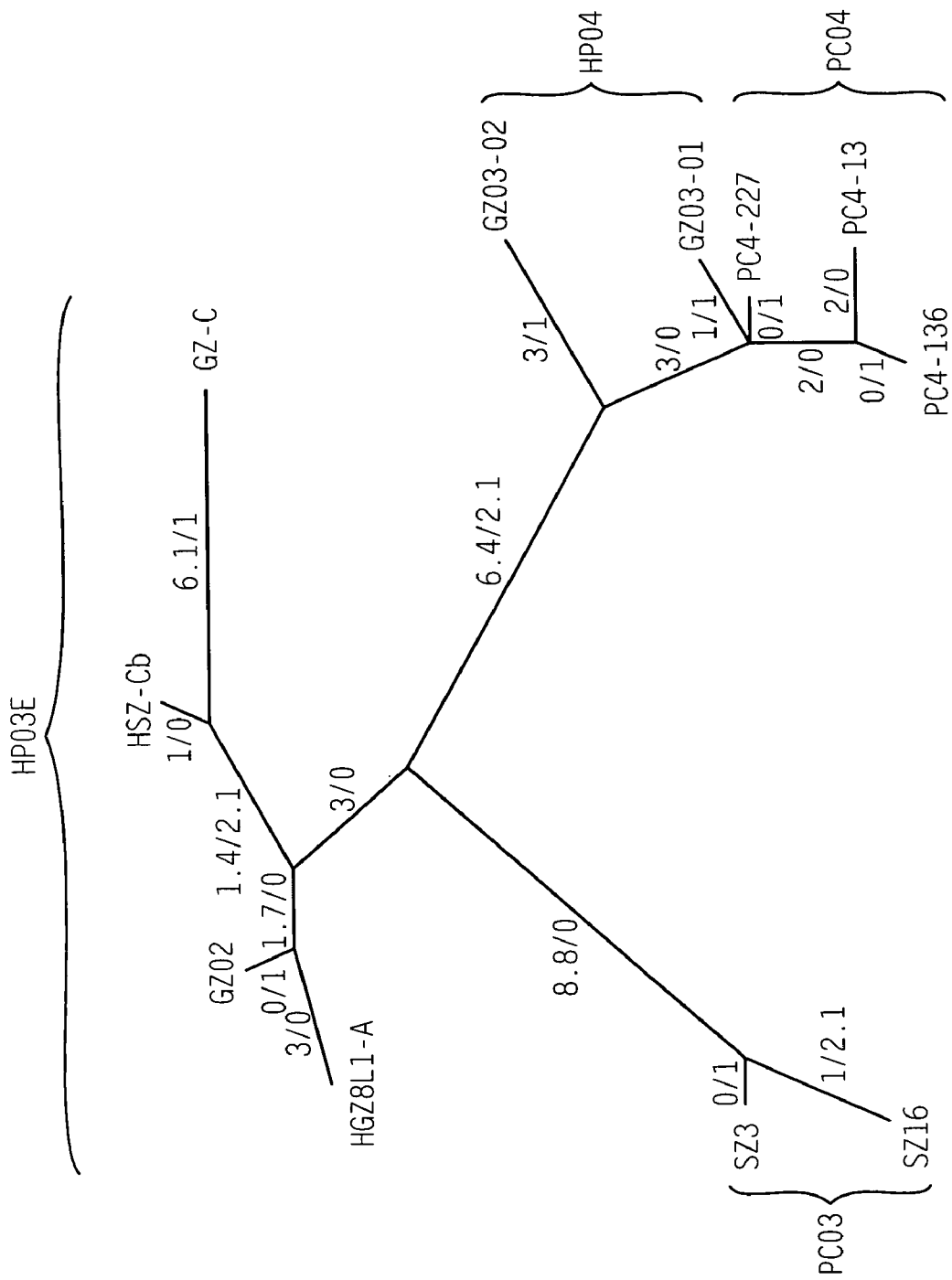
FIGS. 7A-C shows the phylogeny of the most variable genes, Spike (FIG. 7A), sars3a (FIG. 7B), and nsp3 (FIG. 7C) in the SARS-CoV and SARS-CoV-like coronaviral samples from the early HP03-E cases of the 2002-2003 SARS outbreak, from the new HP04 cases of the 2003-2004 outbreak, and from the PC03 and PC04 palm civet sequences. The two numbers shown along each branch are the maximum-likelihood estimates of, respectively, the number of synonymous and nonsynonymous substitutions for each entire gene along that branch. In each tree, a different $d_N/d_S$ ratio is assumed for each branch. The branch length is proportional to the total number of substitutions between sequences.

As shown in FIG. 7A, the S gene sequence has evolved particularly fast, under positive Darwinian selection. First, from the ancestor node of PC03 to the node of HP03-E, the nonsynonymous/synonymous (A/S) ratio is 11.8/0, which corresponds to $\omega=\infty$ ($\omega$: ratio of nonsynonymous and synonymous rates). This confirmed the previous conclusion of Example 1 (see also Chinese SARS Molecular Epidemiology Consortium, *Science* 303:1666 (2004)) that during the virus transmission from palm civet to human, the S gene experienced strong positive selection and improvement in order to adapt to its human host. Within the HP03-E, in most branches, a very high A/S ratio was observed, again suggesting that the S gene was still evolving, having not yet reached its maximum adaptation to human.

Second, from the ancestor node of PC03 to the node of PC04, the A/S ratio is 18.2/2.1 ($\omega=2.68$). This demonstrates that the S gene is also under positive selection pressure during animal to animal transmission. In this regard, it is likely that the SARS-CoV of the current epidemic has evolved to a more virulent form in palm civets, i.e., better adapted to its host. This is supported by the fact that it was much easier to obtain SARS-CoV samples for whole genome sequencing from Guangzhou food market during 2003-2004 period than during the 2002-2003 epidemic (data not show). Interestingly, the ancestor nodes of PC04 and HP04 are the same, indicating that unlike during the 2002-2003 epidemic, these viruses did not have a chance to diverge for enough time, although in the patient GZ03-02, they already accumulated some amino acid changes (A/S=6/1). Because PC03 and PC04 do not belong to the same lineage, these comparisons also implied that the transmission of the virus from animal to human did occur independently.

The significant difference for the level of genomic variation between PC03/HP03-E and PC04/HP04 should be stressed along with the difference of the infectivity of the human SARS cases. In sharp contrast to the 2002-2003 epidemic, no further infection was reported for any of the HP04 cases, while the earliest retrospectively identified SARS patients of the 2002-2003 epidemic infected 2 close contacts directly and 3 others secondarily (see Example 1; see also Chinese SARS Molecular Epidemiology Consortium, *Science* 303:1666 (2004)). Therefore, the so called "early phase" of the 2002-2003 SARS, i.e., HP03-E, should be more accurately described as a "relatively late stage of the early phase," as they have already shown fairly severe symptoms and significant infectivity towards human contacts.

Although the HP03E and HP04 were not from the same lineage of SCoV, the A/S ratio between their ancestor nodes is 9.4/2.1 ($\omega=10.39$). This high ratio further confirmed the idea of positive selection in the early human infection period and implied that HP04, to certain extent, represented the "true" early phase of the virus, i.e., the "very early" or "early-early" phase. In parallel, the A/S or $\omega$ ratio decreased during the course of the epidemic, which suggests that purifying selection began to dominate when the virus had, adapted to the host, as discussed in Example 1 above.

Figure 7B:
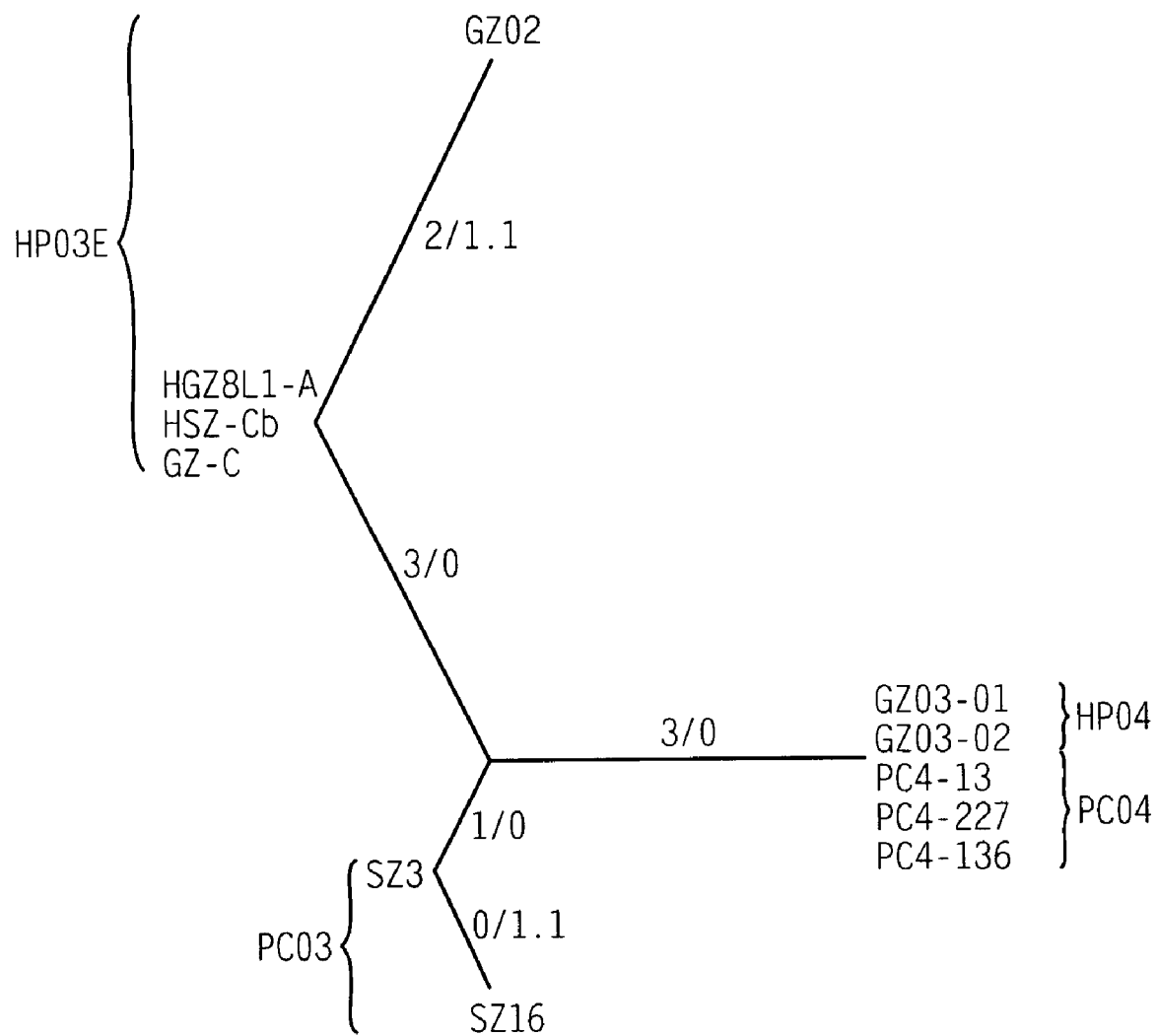
Figure 7C:
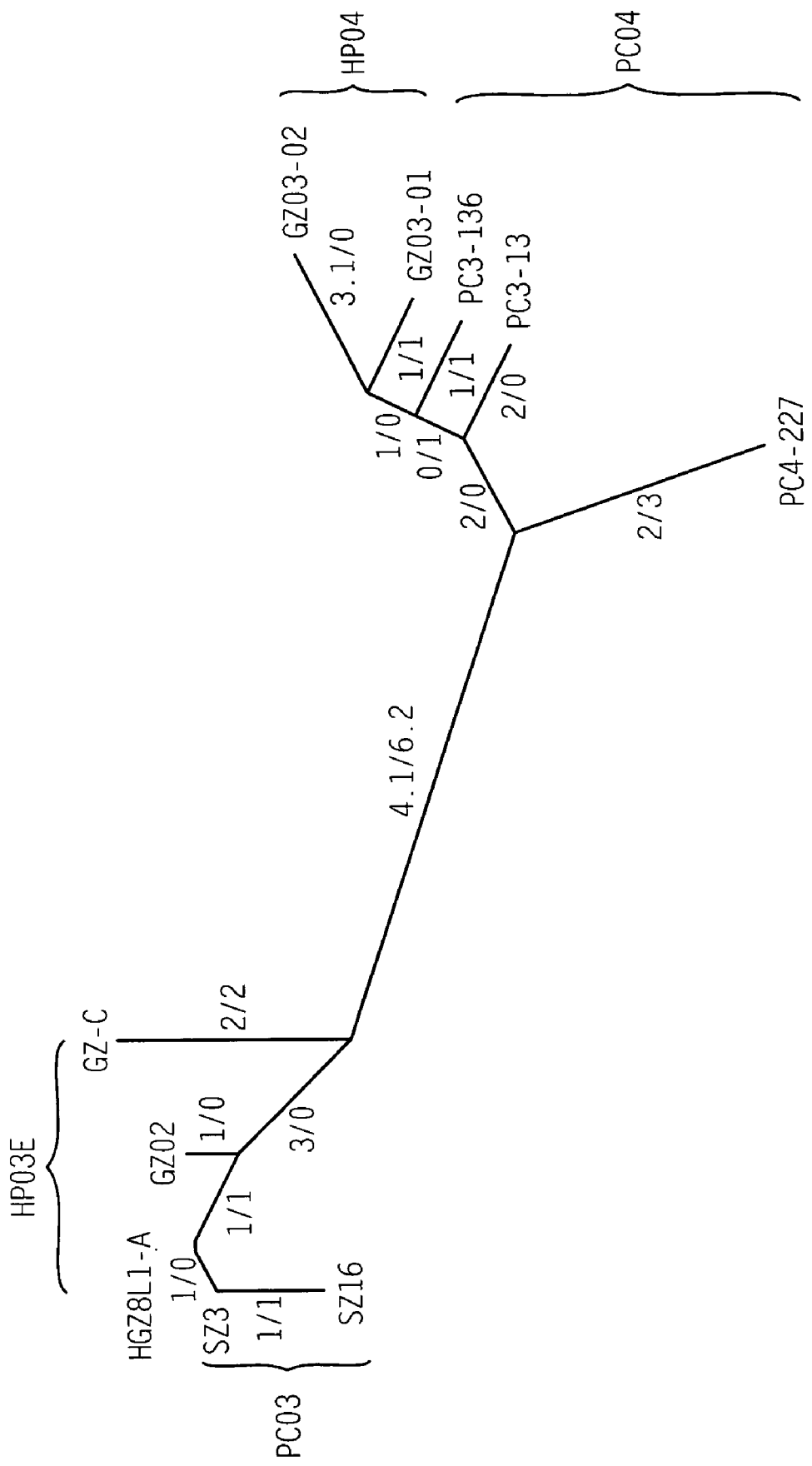

It has been known that the sars3a CDS was expressed and translated into a membrane associated viral structure protein (Zeng et al., *J. Mol. Biol.* in press), while it evolves rapidly, in synergy with the S protein. Therefore, it is not surprising that its evolution showed the same trifurcating tree for the four epidemic groups as that for the S gene, as is shown in FIG. 7B. Combining the three lineages, connecting the ancestor nodes of the four groups, the A/S ratio is 7/0 (there is no synonymous changes) between group HP03-E and HP04. In contrast, there is no single change among palm civets and human beings of the current epidemic. Therefore, it seems that amino acid changes in sars3a are critical to enable human to human (or even animal to animal) transmission and may result in increasing infectiousness during the early period of human to human transmission.

The phylogenetic tree of nsp3 (see FIG. 7C) is largely different from that of Spike or sars3a. The PC03 is very close to HP03-E but relatively more diverging from those of new cases. This suggests that this gene may be under different evolutionary forces from that for Spike and sars3a genes. In the lineage connecting the ancestor node of HP03-E and HP04 (or PC04), the A/S ratio is only. 4.1/6.2 (($\omega$=0.227), which does not show any positive selection signature. It is worth pointing out that in new cases, there is one mutation at nucleotide 6295 leading to a stop codon in the nsp3 CDS of the orf1a, which might account for the mild clinical symptoms and the apparent weak infectivity of this episode.

The Spike protein is responsible for receptor binding and thus, is the fastest evolving protein of SARS-CoV over the epidemic from animal to human. Out of the 17 SNVs observed in animals, 10 are located in the S gene. Among them, 7 were observed in the current epidemic, 1 was observed in the previous epidemic, and 2 were observed in both. With 7 more S gene sequences from samples of the third patient of the current epidemic and of 6 palm civets from Guangzhou food market added for analysis, no further changes were found in the SNV patterns. The three dimensional structure of the S protein simulated by Niccolai et al. (Bernini et al., submitted) was used to better understand the molecular mechanism driving the mutations of the S gene over the course of the epidemic. Although mutations are dispersed over the whole protein, i.e., the S1 and S2 domains, the exposed top or the buried interior, etc., the majority of the mutations are located in the S1 domain (31 out of 48 total SNVs), particularly in the region predicted to constitute the ACE2 receptor binding site, 11 SNVs corresponding to 10 amino acids. Among them, except for 2 synonymous variations, 7 out of the 9 non-synonymous mutations may cause drastic amino acid changes. Two of these non-synonymous mutations, at postions 22422 and 22549, occurred during the 2002-2003 epidemic and represented evolutionary steps in human hosts, while the remaining 5 fell into 3 categories. First, mutations at the second and third nucleotides (22927 and 22928) of codon 479 may cause changes corresponding to 3 different amino acid residues (K, R, or N). Although all of these codons were found in the palm civet samples, only the aat codon for N was found in all the human samples as well as some 2003-2004 palm civet samples. Second, the c→t switch of nt 22570 causing the S→F mutation of codon 360 distinguishes the virus of 2002-2003 epidemic (HP03) from all the other viruses isolated from palm civet (PC03 and PC04) as well as human patients of the 2003-2004' outbreak (HP04). Third, the g→a switch of nt 22930 causing the G→D mutation of codon 480 distinguishes the virus of 2002-2003 (PC03 and HP03) from those of 2003-2004 (PC04 and HP04), regardless of sources.

Although concerted mutation events are extremely rare, the second case was observed for nts 23316 and 23317 encoding amino acid residue 609, which is predicted to be buried at the interface of S proteins. This tta→gca switch causing an L→A mutation is one of a few nonsynonymous mutations that nearly distinguishes the virus of 2002-2003 from those of 2003-2004, disregarding either their human or animal sources. This event is the more remarkable because it also goes in the direction of G+C enrichment, a feature that is usually extremely rare in viruses, for metabolic reasons (Rocha and Danchin, *Trends Genet.* 18:291 (2002)). This indicates that this change, which may modify the relative orientation of the S1 and S2 domains, plays a major role either in the stability of the protein, or in its ability to interact with its target receptor.

In summary, the unfortunate recurrence of SARS at the end of year 2003 provided an opportunity to witness the variation/adaptation behaviour of the etiological agent of the disease. The new SARS-CoV did not derive from the preceding episode, but very likely from a common ancestor, which does not harbor the deletion that marks most of the virulent forms of SCoV for the 2002-2003 epidemic. The fates of the virus inside the human host and in palm civets are similar, i.e., the virus is not yet adapted to its new hosts, making it fast-evolving (possibly into more highly contagious and/or virulent forms); and, in general, the infection is mild. Therefore, humans working with wild animals are often seropositive for the SARS-CoV without noticeable severe symptoms (see Guan et al., *Science* 302:276 (2003)). These data point to a common source of disease lingering in the environment that is presumably both adapted to its natural host and able to come into contact with humans and/or animals. It may have a fairly high probability of mutation under favorable conditions to a form causing SARS in humans. This situation is expected to yield an unusual epidemic pattern, since a proportion of humans may have been immunized against an innocuous form of the virus, so that distribution of the disease, when it happens, is expected to be highly uneven. These data thus strongly suggest the need for further research on the discovery of coronaviruses in animals, in particular in the Guangdong region.

Example 3

SNV Diagnostic Kit

Coronviruses are isolated and cultured from patient samples, including samples obtained from patient phlegm, excrement or tissues. Coronaviral RNA is prepared from these cultures, and cDNA is obtained using reverse transcription. Alternatively, cDNA may be directed obtained from patient samples by reverse transcription without intermediate culturing. This procedure will be particularly important for SARS-CoV or SARS-CoV-like coronaviral strains which are difficult to culture (e.g., which propagate poorly on VeroE6 cells).

PCR reactions are then performed on the cDNA obtained as above, with primers chosen depending upon the insertion(s)/deletion(s) or SNV(s) to be analyzed. For SNVs at positions 22222, 22570, 22927-22928, 22930, 23316-23317, and 23823, for example, one set of suitable primers is the sense primer GCACCCCACCTGCTCTTAATTGT-TATTGGC (SEQ ID NO:6) and the anti-sense primer TAT-TAAAGAGCAAGTCCTCAATAAAAGACC (SEQ ID NO:7). The selection of such primers is based on standard considerations used for PCR amplifications, as would be well-known to one of ordinary skill in the art of such amplifications.

In order to conduct the PCR reaction, primers are diluted to 1 μmol/μl in a solution containing the template cDNA. Amplified PCR fragments are purified and analyzed by sequencing or gel electrophoresis as appropriate.

While the present invention has been described with reference to its preferred embodiments, one of one of ordinary skill in the relevant art will understand that the present invention is not intended to be limited by these preferred embodiments, and is instead contemplated to include all embodiments consistent with the spirit and scope of the present invention as defined by the appended claims.

What is claimed is:

1. A method for detecting an early-stage SARS coronavirus comprising:

providing a sample suspected of containing the early stage SARS coronavirus; and identifying the presence of at least one early-stage-specific molecular marker in a viral RNA, using a protocol comprising preparing coronaviral RNA from the sample, and obtaining cDNA using reverse transcription, wherein the early-stage-specific molecular marker is selected from the group consisting of: an insertion early-stage-specific molecular marker, a deletion early-stage-specific molecular marker, and at least one single nucleotide variation (SNV) early-stage-specific molecular marker, wherein the SNV early-stage-specific molecular marker is C at position 4220.

2. A method for detecting an early-stage SARS coronavirus comprising:

providing a sample suspected of containing the early stage SARS coronavirus, and identifying the presence of at least one early-stage-specific molecular marker in a viral RNA, using a protocol comprising preparing coronaviral RNA from the sample, and obtaining cDNA using reverse transcription, wherein the early-stage-specific molecular marker is selected from the group consisting of: an insertion early-stage-specific molecular marker, a deletion early-stage-specific molecular marker, and at least one single nucleotide variation (SNV) early-stage-specific molecular marker, wherein the at least one SNV is selected from the group of molecular markers consisting of C at position 4220 and C at position 23823.

3. The method of claim 2, wherein the SNV early-stage-specific molecular marker is C at position 4220.

4. A method for detecting an early-stage SARS coronavirus in a patient comprising: obtaining a sample from the patient suspected of containing an early-stage SARS coronavirus;

isolating viral RNA and obtaining cDNA by reverse transcription, determining the nucleotide present at the position corresponding to 4220 in SEQ ID NO: 1, wherein the presence of the nucleotide C at the position indicates an early-stage SARS coronavirus.

5. A method for detecting an early-stage SARS coronavirus comprising:
  obtaining a sample from the patient suspected of containing an early-stage SARS coronavirus;
  isolating viral RNA and obtaining cDNA by reverse transcription,
  determining the nucleotide present at the positions corresponding to 4220 and 23823 in SEQ ID NO: 1, wherein the presence of the nucleotide C at the positions indicates an early-stage SARS coronavirus.

6. The method of claim 5, wherein the presence of the nucleotide C at position 4220 indicates an early-stage SARS coronavirus.

* * * * *

SEQUENCE LISTING

<160> NUMBER OF SEQ ID NOS: 7

<210> SEQ ID NO 1
<211> LENGTH: 29760
<212> TYPE: DNA
<213> ORGANISM: SARS Coronavirus

<400> SEQUENCE: 1

| | | | | | | |
|---|---|---|---|---|---|---|
| atattaggtt | tttacctacc | caggaaaagc | caaccaacct | cgatctcttg | tagatctgtt | 60 |
| ctctaaacga | actttaaaat | ctgtgtagct | gtcgctcggc | tgcatgccta | gtgcacctac | 120 |
| gcagtataaa | caataataaa | ttttactgtc | gttgacaaga | aacgagtaac | tcgtccctct | 180 |
| tctgcagact | gcttacggtt | tcgtccgtgt | tgcagtcgat | catcagcata | cctaggtttc | 240 |
| gtccgggtgt | gaccgaaagg | taagatggag | agccttgttc | ttggtgtcaa | cgagaaaaca | 300 |
| cacgtccaac | tcagtttgcc | tgtccttcag | gttagacg | tgctagtgcg | tggcttcggg | 360 |
| gactctgtgg | aagaggccct | atcggaggca | cgtgaacacc | tcaaaaatgg | cacttgtggt | 420 |
| ctagtagagc | tggaaaaagg | cgtactgccc | cagcttgaac | agccctatgt | gttcattaaa | 480 |
| cgttctgatg | ccttaagcac | caatcactgc | cacaaggtcg | ttgagctggt | tgcagaaatg | 540 |
| gacggcattc | agtacggtcg | tagcggtata | acactgggag | tactcgtgcc | acatgtgggc | 600 |
| gaaaccccaa | ttgcataccg | caatgttctt | cttcgtaaga | acggtaataa | gggagccggt | 660 |
| ggtcatagct | atggcatcga | tctaaagtct | tatgacttag | gtgacgagct | tggcactgat | 720 |
| cccattgaag | attatgaaca | aaactggaac | actaagcatg | gcagtggtgc | actccgtgaa | 780 |
| ctcactcgtg | agctcaatgg | aggtgcagtc | actcgctatg | tcgacaacaa | tttctgtggc | 840 |
| ccagatgggt | accctcttga | ttgcatcaaa | gattttctcg | cacgcgcggg | caagtcaatg | 900 |
| tgcactcttt | ccgaacaact | tgattacatc | gagtcgaaga | gaggtgtcta | ctgctgccgt | 960 |
| gaccatgagc | atgaaattgc | ctggttcact | gagcgctctg | ataagagcta | cgagcaccag | 1020 |
| acacccttcg | aaattaagag | tgccaagaaa | tttgacactt | tcaaagggga | atgcccaaag | 1080 |
| tttgtgtttc | ctcttaactc | aaaagtcaaa | gtcattcaac | cacgtgttga | aagaaaaag | 1140 |
| actgagggtt | tcatggggcg | tatacgctct | gtgtaccctg | ttgcatctcc | acaggagtgt | 1200 |
| aacaacatgc | acttgtctac | cttgatgaaa | tgtaatcatt | gcgatgaagt | tcatggcag | 1260 |
| acgtgcgact | ttctgaaagc | cacttgtgaa | cattgtggca | ctgaaaattt | agttattgaa | 1320 |
| ggacctacta | catgtgggta | cctacctact | aatgctgtag | tgaaaatgcc | atgtcctgcc | 1380 |
| tgtcaagacc | cagagattgg | acctgagcat | agtgttgcag | attatcacaa | ccactcaaac | 1440 |
| attgaaactc | gactccgcaa | gggaggtagg | actagatgtt | ttggaggctg | tgtgtttgcc | 1500 |
| tatgttggct | gctataataa | gcgtgcctac | tgggttcctc | gtgctagtgc | tgatattggc | 1560 |
| tcaggccata | ctggcattac | tggtgacaat | gtggagacct | tgaatgagga | tctccttgag | 1620 |
| atactgagtc | gtgaacgtgt | taacattaac | attgttggcg | attttcattt | gaatgaagag | 1680 |
| gttgccatca | ttttggcatc | tttctctgct | tctacaagtg | cctttattga | cactataaag | 1740 |
| agtcttgatt | acaagtcttt | caaaaccatt | gttgagtcct | gcggtaacta | taagttacc | 1800 |
| aagggaaagc | ccgtaaaagg | tgcttggaac | attggacaac | agagatcagt | tttaacacca | 1860 |
| ctgtgtggtt | ttccctcaca | ggctgctggt | gttatcagat | caatttttgc | gcgcacactt | 1920 |
| gatgcagcaa | accactcaat | tcctgatttg | caaagagcag | ctgtcaccat | acttgatggt | 1980 |
| atttctgaac | agtcattacg | tcttgtcgac | gccatggttt | atacttcaga | cctgctcacc | 2040 |

-continued

```
aacagtgtca ttattatggc atatgtaact ggtggtcttg tacaacagac ttctcagtgg    2100
ttgtctaatc tttttgggcac tactgttgaa aaactcaggc ctatctttga atggattgag   2160
gcgaaactta gtgcaggagt tgaatttctc aaggatgctt gggagattct caaatttctc   2220
attacaggtg tttttgacat cgtcaagggt caaatacagg ttgcttcaga taacatcaag   2280
gattgtgtaa aatgcttcat tgatgttgtt aacaaggcac tcgaaatgtg cattgatcaa   2340
gtcactatcg ctgcgcaaa gttgcgatca ctcaacttag gtgaagtctt catcgctcaa    2400
agcaagggac tttaccgtca gtgtatacgt ggcaaggagc agctgcaact actcatgcct   2460
cttaaggcac caaaagaagt aacctttctt gaaggtgatt cacatgacac agtacttacc   2520
tctgaggagg ttgttctcaa gaacggtgaa ctcgaagcac tcgagacgcc cgttgatagc   2580
ttcacaaatg gagctatcgt tggcacacca gtctgtgtaa atggcctcat gctcttagag   2640
attaaggaca agaacaata ctgcgcattg tctcctggtt tactggctac aaacaatgtc    2700
tttcgcttaa aaggggggtgc accaattaaa ggtgtaacct ttggagaaga tactgtttgg   2760
gaagttcaag gttacaagaa tgtgagaatc acatttgagc ttgatgaacg tgttgacaaa   2820
gtgcttaatg aaaagtgctc tgtctacact gttgaatccg gtaccgaagt tactgagttt   2880
gcatgtgttg tagcagaggc tgttgtgaag actttacaac cagtttctga tctccttacc   2940
aacatgggta ttgatcttga tgagtggagt gtagctacat tctacttatt tgatgatgct   3000
ggtgaagaaa acttttcatc acgtatgtat tgttccttt accctccaga tgaggaagaa    3060
gaggacgatg cagagtgtga ggaagaagaa attgatgaaa cctgtgaaca tgagtacggt   3120
acagaggatg attatcaagg tctccctctg gaatttggtg cctcagctga aacagttcga   3180
gttgaggaag aagaagagga agactggctg atgatgacta ctgagcaatc agagattgag   3240
ccagaaccag aacctacacc tgaagaacca gttaatcagt ttactggtta ttttaaaact   3300
actgacaatg ttgccattaa aatgtgctgac atcgttaagg aggcacaaag tgctaatcct   3360
atggtgattg taaatgctgc taacatacac ctgaaacatg gtggtggtgt agcaggtgca   3420
ctcaacaagg caaccaatgg tgccatgcaa aaggagagtg atgattacat taagctaaat   3480
ggccctctta cagtaggagg gtcttgtttg ctttctggac ataatcttgc taagaagtgt   3540 ctgcatgtt ttggacctaa cctaaatgca ggtgaggaca tccagcttct taaggcagca   3600
tatgaaaatt tcaattcaca ggacacccta cttgcaccat tgttgtcagc aggcatattt   3660
ggtgctaaac cacttcagtc tttacaagtg tgcgtgcaga cggttcgtac acaggtttat   3720
attgcagtca atgacaaagc tctttatgag caggttgtca tggattatct tgataacctg   3780
aagcctagag tggaagcacc taaacaagag gagccaccaa acacagaaga ttccaaaact   3840
gaggagaaat ctgtcgtaca aagcctgtc gatgtgaagc caaaaattaa ggcctgcatt   3900
gatgaggtta ccacaacact ggaagaaact aagtttctta ccaataagtt actcttgttt   3960
gctgatatca atggtaagct ttaccatgat tctcagaaca tgcttagagg tgaagatatg   4020
tctttccttg agaaggatgc accttacatg taggtgatg ttatcactag tggtgatatc   4080
acttgtgttg taatacccctc caaaaaggct ggtggcacta ctgagatgct ctcaagagct   4140
ttgaagaaag tgccagttga tgagtatata accacgtacc ctggacaagg atgtgctggt   4200
tatacacttg aggaagctag gactgctctt aagaaatgca atctgcatt ttatgtacta    4260 ccttcagaag cacctaatgc taaggaagag attctaggaa ctgtatcctg gaatttgaga   4320
gaaatgcttg ctcatgctga agagacaaga aaattaatgc ctatatgcat ggatgttaga   4380
```

```
gccataatgg caaccatcca acgtaagtat aaaggaatta aaattcaaga gggcatcgtt    4440
gactatggtg tccgattctt cttttatact agtaaagagc ctgtagcttc tattattacg    4500
aagctgaact ctctaaatga gccgcttgtc acaatgccaa ttggttatgt gacacatggt    4560
tttaatcttg aagaggctgc gcgctgtatg cgttctctta aagctcctgc cgtagtgtca    4620
gtatcatcac cagatgctgt tactacatat aatggatacc tcacttcgtc atcaaagaca    4680
tctgaggagc actttgtaga aacagtttct ttggctggct cttacagaga ttggtcctat    4740
tcaggacagc gtacagagtt aggtgttgaa tttcttaagc gtggtgacaa aattgtgtac    4800
cacactctgg agagcccgt cgagtttcat cttgacggtg aggttctttc acttgacaaa    4860
ctaaagagtc tcttatccct gcgggaggtt aagactataa agtgttcac aactgtggac    4920 aacactaatc tccacacaca gcttgtggat atgtctatga catatggaca gcagtttggt    4980
ccaacatact tggatggtgc tgatgttaca aaaattaaac ctcatgtaaa tcatgagggt    5040
aagactttct ttgtactacc tagtgatgac acactacgta gtgaagcttt cgagtactac    5100
catactcttg atgagagttt tcttggtagg tacatgtctg ctttaaacca cacaaagaaa    5160
tggaaatttc ctcaagttgg tggtttaact tcaattaaat gggctgataa caattgttat    5220
ttgtctagtg ttttattagc acttcaacag attgaagtca aattcaatgc accagcactt    5280
caagaggctt attatagagc ccgtgctggt gatgctgcta cttttgtgc actcatactc    5340 gcttacagta ataaaactgt tggcgagctt ggtgatgtca gagaaactat gacccatctt    5400
ctacagcatg ctaatttgga atctgcaaag cgagttctta atgtggtgtg taaacattgt    5460
ggtcagaaaa ctactacctt aacgggtgta gaagctgtga tgtatatggg tactctatct    5520
tatgataatc ttaagacagg tgtttccatt ccatgtgtgt gtggtcgtga tgctacacaa    5580
tatctagtac aacaagagtc ttcttttgtt atgatgtctg caccacctgc tgagtataaa    5640
ttacagcaag gtacattctt atgtgcgaat gagtacactg gtaactatca gtgtggtcat    5700
tacactcata taactgctaa ggagaccctc tatcgtattg acggagctca ccttacaaag    5760
atgtcagagt acaaaggacc agtgactgat gttttctaca aggaaacatc ttacactaca    5820
accatcaagc ctgtgtcgta taactcgat ggagttactt acacagagat tgaaccaaaa    5880
ttggatgggt attataaaaa ggataatgct tactatacag agcagcctat agaccttgta    5940
ccaactcaac cattaccaaa tgcgagtttt gataatttca actcacatg ttctaacaca    6000 aaatttgctg atgatttaaa tcaaatgaca ggcttcacaa agccagcttc acgagagcta    6060
tctgtcacat tcttcccaga cttgaatggc gatgtagtgg ctattgacta tagacactat    6120
tcagcgagtt tcaagaaagg tgctaaatta ctgcataagc caattgtttg gcacattaac    6180
caggctacaa ccaagacaac gttcaaacca aacacttggt gtttacgttg tctttggagt    6240
acaaagccag tagatacttc aaattcattt gaagttctgg cagtagaaga cacacaagga    6300
atggacaatc ttgcttgtga agtcaacaa cccacctctg aagaagtagt ggaaaatcct    6360
accatacaga aggaagtcat agagtgtgac gtgaaaacta ccgaagttgt aggcaatgtc    6420
atacttaaac catcagatga aggtgttaaa gtaacacaag agttaggtca tgaggatctt    6480
atggctgctt atgtggaaaa cacaagcatt accattaaga aacctaatga gctttcacta    6540
gccttaggtt taaaaacaat tgccactcat ggtattgctg caattaatag tgttccttgg    6600
agtaaaattt ttgcttatgt caaaccattc ttaggacaag cagcaattac aacatcaaat    6660
tgcgctaaga gattagcaca acgtgtgttt aacaattata tgccttatgt gtttacatta    6720
ttgttccaat tgtgtacttt tactaaaagt accaattcta gaattagagc ttcactacct    6780
```

```
acaactattg ctaaaaatag tgttaagagt gttgctaaat tatgtttgga tgccggcatt    6840
aattatgtga agtcacccaa attttctaaa ttgttcacaa tcgctatgtg gctattgttg    6900
ttaagtattt gcttaggttc tctaatctat gtaactgctg cttttggtgt actcttatct    6960
aattttggtg ctccttctta ttgtaatggc gttagagaat tgtatcttaa ttcgtctaac    7020
gttactacta tggatttctg tgaaggttct tttccttgca gcatttgttt aagtggatta    7080
gactcccttg attcttatcc agctcttgaa accattcagg tgacgatttc atcgtacaag    7140
ctagacttga caattttagg tctggccgct gagtgggttt ggcatatat gttgttcaca     7200 aaattctttt atttattagg tctttcagct ataatgcagg tgttctttgg ctattttgct    7260
agtcatttca tcagcaattc ttggctcatg tggtttatca ttagtattgt acaaatggca    7320
cccgtttctg caatggttag gatgtacatc ttctttgctt ctttctacta catatggaag    7380
agctatgttc atatcatgga tggttgcacc tcttcgactt gcatgatgtg ctataagcgc    7440
aatcgtgcca cacgcgttga gtgtacaact attgttaatg gcatgaagag atctttctat    7500
gtctatgcaa atggaggccg tggcttctgc aagactcaca attggaattg tctcaattgt    7560
gacacatttt gcactggtag tacattcatt agtgatgaag ttgctcgtga tttgtcactc    7620
cagtttaaaa gaccaatcaa ccctactgac cagtcatcgt atattgttga tagtgttgct    7680
gtgaaaaatg gcgcgcttca cctctacttt gacaaggctg gtcaaaagac ctatgagaga    7740
catccgctct cccatttttgt caatttagac aatttgagag ctaacaacac taaaggttca    7800
ctgcctatta atgtcatagt ttttgatggc aagtccaaat gcgacgagtc tgcttctaag    7860
tctgcttctg tgtactacag tcagctgatg tgccaaccta ttctgttgct tgaccaagct    7920
cttgtatcag acgttggaga tagtactgaa gtttccgtta agatgtttga tgcttatgtc    7980
gacacctttt cagcaacttt tagtgttcct atggaaaaac ttaaggcact tgttgctaca    8040
gctcacagcg agttagcaaa gggtgtagct ttagatggtg tcctttctac attcgtgtca    8100
gctgcccgac aagtgttgt tgataccgat gttgacacaa aggatgttat tgaatgtctc    8160
aaactttcac atcactctga cttagaagtg acaggtgaca gttgtaacaa tttcatgctc    8220
acctataata aggttgaaaa catgacgccc agagatcttg gcgcatgtat tgactgtaat    8280
gcaaggcata tcaatgccca agtagcaaaa agtcacaatg tttcactcat ctggaatgta    8340
aaagactaca tgtctttatc tgaacagctg cgtaaacaaa ttcgtagtgc tgccaagaag    8400
aacaacatac cttttagact aacttgtgct acaactagac aggttgtcaa tgtcataact    8460
actaaaatct cactcaaggg tggtaagatt gttagtactt ggtttaaact tatgcttaag    8520
gccacattat tgtgcgttct tgctgcattg gtttgttaca tcgttatgcc agtcacataca    8580 ttgtcaatcc atgatggtta cacaaatgaa atcattggtt acaaagccat tcaggatggt    8640
gtcactcgtg acatcatttc tactgatgat tgttttgcaa ataaacatgc tggttttgac    8700
gcatggttta gccagcgtgg tggttcatac aaaaatgaca aaagctgccc tgtagtagct    8760
gctatcatta caagagagat tggtttcata gtgcctggct taccgggtac tgtgttgaga    8820
gcaatcaatg gtgacttctt gcattttcta cctcgtgttt ttagtgctgt tggcaacatt    8880
tgctacacac cttccaaact cattgagtat agtgattttg ctacctctgc ttgcgttctt    8940
gctgcagagt gtacaatttt taaggatgct atgggcaaac ctgtgccata ttgttatgac    9000
actaatttgc tagagggttc tatttcttat agtgagcttc gtccagacac tcgttatgtg    9060
cttatggatg gttccatcat acagtttcct aacatttacc tggagggttc tgttagagta    9120
```

```
gtaacaactt ttgatgctga gtactgtaga catggtacat gcgaaaggtc agaagcaggt    9180
atttgcctat ctaccagtgg tagatgggtt cttaataatg agcattacag agctctatca    9240
ggagttttct gtggtgttga tgcgatgaat ctcatagcta acatctttac tcctcttgtg    9300
caacctgtgg gtgctttaga tgtgtctgct tcagtagtgg ctggtggtat tattgccata    9360
ttggtgactt gtgctgccta ctactttatg aaattcagac gtgcttttgg tgagtacaac    9420
catgttgttg ctgctaatgc acttttgttt ttgatgtctt tcactatact ctgtctggca    9480
ccagcttaca gctttctgcc gggagtctac tcagtctttt acttgtactt gacattctat    9540
ttcaccaatg atgtttcatt cttggctcac cttcaatggt ttgccatgtt ttctcctatt    9600
gtgcctttt ggataacagc aatctatgta ttctgtattt ctctgaagca ctgccattgg    9660
ttctttaaca actatcttag gaaaagagtc atgtttaatg gagttacatt tagtaccttc    9720
gaggaggctg ctttgtgtac ctttttgctc aacaaggaaa tgtacctaaa attgcgtagc    9780
gagacactgt tgccacttac acagtataac aggtatcttg ctctatataa caagtacaag    9840
tatttcagtg gagccttaga tactaccagc tatcgtgaag cagcttgctg ccacttagca    9900
aaggctctaa atgactttag caactcaggt gctgatgttc tctaccaacc accacagaca    9960
tcaatcactt ctgctgttct gcagagtggt tttaggaaaa tggcattccc gtcaggcaaa    10020
gttgaaggat gcatggtaca agtaacctgt ggaactacaa ctcttaatgg attgtggttg    10080
gatgacacag tatactgtcc aagacatgtc atttgcacag cagaagacat gcttaatcct    10140
aactatgaag atctgctcat tcgcaaatcc aaccatagct tccttgttca ggctggcaat    10200
gttcaacttc gtgttattgg ccattctatg caaaattgtc tgcttaggct taaagttgat    10260
acttctaacc ctaagacacc caagtataaa tttgtccgta tccaacctgg tcaaacattt    10320
tcagttctag catgctacaa tggttcacca tctggtgttt atcagtgtgc catgagacct    10380
aatcatacca ttaaaggttc tttccttaat ggatcatgtg gtagtgttgg ttttaacatt    10440
gattatgatt gcgtgtcttt ctgctatatg catcatatgg agcttccaac aggagtacac    10500
gctggtactg acttagaagg taaattctat ggtccatttg ttgacagaca aactgcacag    10560
gctgcaggta cagacacaac cataacatta atgttttggg catggctgta tgctgctgtt    10620
atcaatggtg ataggtggtt tcttaataga ttcaccacta cttttgaatga ctttaacctt    10680
gtggcaatga agtacaacta tgaacctttg acacaagatc atgttgacat attgggacct    10740
ctttctgctc aaacaggaat tgccgtctta gatatgtgtg ctgctttgaa agagctgctg    10800
cagaatggta tgaatggtcg tactatcctt ggtagcacta ttttagaaga tgagtttaca    10860
ccatttgatg ttgttagaca atgctctggt gttaccttcc aagtaagtt caagaaaatt    10920
gttaagggca ctcatcattg gatgcttta acttttttga catcactatt gattcttgtt    10980
caaagtacac agtggtcact gtttttcttt gtttacgaga atgctttctt gccatttact    11040
cttggtatta tggcaattgc tgcatgtgct atgctgcttg ttaagcataa gcacgcattc    11100
ttgtgcttgt ttctgttacc ttctcttgca acagttgctt actttaatat ggtctacatg    11160
cctgctagct gggtgatgcg tatcatgaca tggcttgaat tggctgacac tagcttgtct    11220
ggttataggc ttaaggattg tgttatgtat gcttcagctt tagttttgct tattctcatg    11280
acagctcgcc ctgtttatga tgatgctgct agacgtgttt ggacactgat gaatgtcatt    11340
acacttgttt acaaagtcta ctatggtaat gctttagatc aagctatttc catgtgggcc    11400
ttagttattt ctgtaacctc taactattct ggtgtcgtta cgactatcat gttttttagct    11460
agagctatag tgtttgtgtg tgttgagtat taccccattgt tatttattac tggcaacacc    11520
```

```
ttacagtgta tcatgcttgt ttattgtttc ttaggctatt gttgctgctg ctactttggc   11580
cttttctgtt tactcaaccg ttacttcagg cttactcttg gtgtttatga ctacttggtc   11640
tctacacaag aatttaggta tatgaactcc caggggcttt tgcctcctaa gagtagtatt   11700
gatgctttca agcttaacat taagttgttg ggtattggag gtaaaccatg tatcaaggtt   11760
gctactgtac agtctaaaat gtctgacgta aagtgcacat ctgtggtact gctctcggtt   11820
cttcaacaac ttagagtaga gtcatcttct aaattgtggg cacaatgtgt acaactccac   11880
aatgatattc ttcttgcaaa agacacaact gaagctttcg agaagatggt ttctcttttg   11940
tctgttttgc tatccatgca gggtgctgta gacattaata ggttgtgcga ggaaatgctc   12000
gataaccgtg ctactcttca ggctattgct tcagaattta gttctttacc atcatatgcc   12060
gcttatgcca ctgcccagga ggcctatgag caggctgtag ctaatggtga ttctgaagtc   12120
gttctcaaaa agttaaagaa atctttgaat gtggctaaat ctgagtttga ccgtgatgct   12180
gccatgcaac gcaagttgga aaagatggca gatcaggcta tgacccaaat gtacaaacag   12240
gcaagatctg aggacaagag ggcaaaagta actagtgcta tgcaaacaat gctcttcact   12300
atgcttagga agcttgataa tgatgcactt aacaacatta tcaacaatgc gcgtgatggt   12360
tgtgttccac tcaacatcat accattgact acagcagcca aactcatggt tgttgtccct   12420
gattatggta cctacaagaa cacttgtgat ggtaacacct ttacatatgc atctgcactc   12480
tgggaaatcc agcaagttgt tgatgcggat agcaagattg ttcaacttag tgaaattaac   12540
atggacaatt caccaaattt ggcttggcct cttattgtta cagctctaag agccaactca   12600
gctgttaaac tacagaataa tgaactgagt ccagtagcac tacgacagat gtcctgtgcg   12660
gctggtacca cacaaacagc ttgtactgat gacaatgcac ttgcctacta taacaattcg   12720
aagggaggta ggtttgtgct ggcattacta tcagaccacc aagatctcaa atgggctaga   12780
ttccctaaga gtgatggtac aggtacaatt tacacagaac tggaaccacc ttgtaggttt   12840
gttacagaca caccaaaagg gcctaaagtg aaatacttgt acttcatcaa aggcttaaac   12900
aacctaaata gaggtatggt gctgggcagt ttagctgcta cagtacgtct tcaggctgga   12960
aatgctacag aagtacctgc caattcaact gtgctttcct tctgtgcttt tgcagtagac   13020
cctgctaaag catataagga ttacctagca agtggaggac aaccaatcac caactgtgtg   13080
aagatgttgt gtacacacac tggtacagga caggcaatta ctgtaacacc agaagctaac   13140
atggaccaag agtcctttgg tggtgcttca tgttgtctgt attgtagatg ccacattgac   13200
catccaaatc ctaaaggatt ctgtgacttg aaaggtaagt acgtccaaat acctaccact   13260
tgtgctaatg acccagtggg ttttacactt agaaacacag tctgtaccgt ctgcggaatg   13320
tggaaaggtt atggctgtag ttgtgaccaa ctccgcgaac ccttgatgca gtctgcggat   13380
gcatcaacgt ttttaaacgg gtttgcggtg taagtgcagc ccgtcttaca ccgtgcggca   13440
caggcactag tactgatgtc gtctacaggg cttttgatat ttacaacgaa aaagttgctg   13500
gttttgcaaa gttcctaaaa actaattgct gtcgcttcca ggagaaggat gaggaaggca   13560
atttattaga ctcttacttt gtagttaaga ggcatactat gtctaactac caacatgaag   13620
agactattta aacttggtt aaagattgtc cagcggttgc tgtccatgac ttttttcaagt   13680 ttagagtaga tggtgacatg gtaccacata tatcacgtca gcgtctaact aaatacacaa   13740
tggctgattt agtctatgct ctacgtcatt ttgatgaggg taattgtgat acattaaaag   13800
aaatactcgt cacatacaat tgctgtgatg atgattattt caataagaag gattggtatg   13860
```

```
acttcgtaga gaatcctgac atcttacgcg tatatgctaa cttaggtgag cgtgtacgcc    13920
aatcattatt aaagactgta caattctgcg atgctatgcg tgatgcaggc attgtaggcg    13980
tactgacatt agataatcag gatcttaatg ggaactggta cgatttcggt gatttcgtac    14040
aagtagcacc aggctgcgga gttcctattg tggattcata ttactcattg ctgatgccca    14100
tcctcacttt gactagggca ttggctgctg agtcccatat ggatgctgat ctcgcaaaac    14160
cacttattaa gtgggatttg ctgaaatatg attttacgga agagagactt tgtctcttcg    14220
accgttattt taaatattgg gaccagacat accatcccaa ttgtattaac tgtttggatg    14280
ataggtgtat ccttcattgt gcaaacttta atgtgttatt ttctactgtg tttccaccta    14340
caagttttgg accactagta agaaaaatat ttgtagatgg tgttcctttt gttgtttcaa    14400
ctggatacca ttttcgtgag ttaggagtcg tacataatca ggatgtaaac ttacatagct    14460
cgcgtctcag tttcaaggaa cttttagtgt atgctgctga tccagctatg catgcagctt    14520
ctggcaattt attgctagat aaacgcacta catgcttttc agtagctgca ctaacaaaca    14580
atgttgcttt tcaaactgtc aaacccggta attttaataa agacttttat gactttgctg    14640
tgtctaaagg tttctttaag gaaggaagtt ctgttgaact aaaacacttc ttctttgctc    14700
aggatggcaa cgctgctatc agtgattatg actattatcg ttataatctg ccaacaatgt    14760
gtgatatcag acaactccta ttcgtagttg aagttgttga taaatacttt gattgttacg    14820
atggtggctg tattaatgcc aaccaagtaa tcgttaacaa tctggataaa tcagctggtt    14880
tcccatttaa taaatggggt aaggctagac tttattatga ctcaatgagt tatgaggatc    14940
aagatgcact tttcgcgtat actaagcgta atgtcatccc tactataact caaatgaatc    15000
ttaagtatgc cattagtgca aagaatagag ctcgcaccgt agctggtgtc tctatctgta    15060
gtactatgac aaatagacag tttcatcaga aattattgaa gtcaatagcc gccactagag    15120
gagctactgt ggtaattgga acaagcaagt tttacggtgg ctggcataat atgttaaaaa    15180
ctgtttacag tgatgtagaa actccacacc ttatgggttg ggattatcca aaatgtgaca    15240
gagccatgcc taacatgctt aggataatgg cctctcttgt tcttgctcgc aaacataaca    15300
cttgctgtaa cttatcacac cgtttctaca ggttagctaa cgagtgtgcg caagtattaa    15360
gtgagatggt catgtgtggc ggctcactat atgttaaacc aggtggaaca tcatccggtg    15420
atgctacaac tgcttatgct aatagtgtct ttaacatttg tcaagctgtt acagccaatg    15480
taaatgcact tctttcaact gatggtaata agatagctga caagtatgtc cgcaatctac    15540
aacacaggct ctatgagtgt ctctatagaa atagggatgt tgatcatgaa ttcgtggatg    15600
agttttacgc ttacctgcgt aaacatttct ccatgatgat tctttctgat gatgccgttg    15660
tgtgctataa cagtaactat gcggctcaag gtttagtagc tagcattaag aactttaagg    15720
cagttcttta ttatcaaaat aatgtgttca tgtctgaggc aaaatgttgg actgagactg    15780
accttactaa aggacctcac gaattttgct cacagcatac aatgctagtt aaacaaggag    15840
atgattacgt gtacctgcct tacccagatc catcaagaat attaggcgca ggctgttttg    15900
tcgatgatat tgtcaaaaca gatggtacac ttatgattga aaggttcgtg tcactggcta    15960
ttgatgctta cccacttaca aaacatccta atcaggagta tgctgatgtc tttcacttgt    16020
atttacaata cattagaaag ttacatgatg agcttactgg ccacatgttg gacatgtatt    16080
ccgtaatgct aactaatgat aacacctcac ggtactggga acctgagttt tatgaggcta    16140
tgtacacacc acatacagtc ttgcaggctg taggtgcttg tgtattgtgc aattcacaga    16200
cttcacttcg ttgcggtgcc tgtattagga gaccattcct atgttgcaag tgctgctatg    16260
```

-continued

```
accatgtcat ttcaacatca cacaaattag tgttgtctgt taatccctat gtttgcaatg    16320
ccccaggttg tgatgtcact gatgtgacac aactgtatct aggaggtatg agctattatt    16380
gcaagtcaca taagcctccc attagttttc cattatgtgc taatggtcag ttttttggtt    16440
tatacaaaaa cacatgtgta ggcagtgaca atgtcactga cttcaatgcg atagcaacat    16500
gtgattggac taatgctggc gattacatac ttgccaacac ttgtactgag agactcaagc    16560
ttttcgcagc agaaacgctc aaagccactg aggaaacatt taagctgtca tatggtattg    16620
ccactgtacg cgaagtactc tctgacagag aattgcatct tcatgggag gttggaaaac     16680 ctagaccacc attgaacaga aactatgtct ttactggtta ccgtgtaact aaaaatagta    16740
aagtacagat tggagagtac acctttgaaa aggtgactaa tggtgatgct gttgtgtaca    16800
gaggtactac gacatacaag ttgaatgttg gtgattactt tgtgttgaca tctcacactg    16860
taatgccact tagtgcacct actctagtgc cacaagagca ctatgtgaga attactggct    16920
tgtacccaac actcaacatc tcagatgagt tttctagcaa tgttgcaaat tatcaaaagg    16980
tcggcatgca aaagtactct acactccaag gaccacctgg tactggtaag agtcattttg    17040
ccatcggact tgctctctat tacccatctg ctcgcatagt gtatacggca tgctctcatg    17100
cagctgttga tgccctatgt gaaaaggcat caaaatattt gcccatagat aaatgtagta    17160
gaatcatacc tgcgcgtgcg cgcgtagagt gttttgataa attcaaagtg aattcaacac    17220
tagaacagta tgttttctgc actgtaaatg cattgccaga aacaactgct gacattgtag    17280
tctttgatga aatctctatg ctactaatt atgacttgag tgttgtcaat gctagacttc     17340
gtgcaaaaca ctacgtctat attggcgatc ctgctcaatt accagccccc cgcacattgc    17400
tgactaaagg cacactagaa ccagaatatt ttaattcagt gtgcagactt atgaaaacaa    17460
taggtccaga catgttcctt ggaacttgtc gccgttgtcc tgctgaaatt gttgacactg    17520
tgagtgcttt agtttatgac aataagctaa agcacacaa ggagaagtca gctcaatgct      17580
tcaaaatgtt ctacaaaggt gttattacac atgatgtttc atctgcaatc aacagacctc    17640
aaataggcgt tgtaagagaa tttcttacac gcaatcctgc ttggagaaaa gctgttttta    17700
tctcacctta taattcacag aacgctgtag cttcaaaaat cttaggattg cctacgcaga    17760
ctgttgattc atcacagggt tctgaatatg actatgtcat attcacacaa actactgaaa    17820
cagcacactc ttgtaatgtc aaccgcttca atgtggctat cacaagggca aaaattggca    17880
ttttgtgcat aatgtctgat agagatcttt atgacaaact gcaatttaca agtctagaaa    17940
taccacgtcg caatgtggct acattacaag cagaaatgt aactggactt tttaaggact     18000
gtagtaagat cattactggt cttcatccta cacaggcacc tacacacctc agcgttgata    18060
taaagttcaa gactgaagga ttatgtgttg acatacagg cataccaaag gacatgacct     18120
accgtagact catctctatg atgggtttca aaatgaatta ccaagtcaat ggttacccta    18180
atatgtttat cacccgcgaa gaagctattc gtcacgttcg tgcgtggatt ggctttgatg    18240
tagagggctg tcatgcaact agagatgctg tgggtactaa cctacctctc cagctaggat    18300
tttctacagg tgttaactta gtagctgtac cgactggtta tgttgacact gaaaataaca    18360
cagaattcac cagagttaat gcaaaacctc caccaggtga ccagtttaaa catcttatac    18420
cactcatgta taaggcttg ccctggaatg tagtgcgtat taagatagta caaatgctca     18480
gtgatacact gaaaggattg tcagacagag tcgtgttcgt cctttgggcg catggcttg     18540 agcttacatc aatgaagtac tttgtcaaga ttggacctga aagaacgtgt tgtctgtgtg    18600
```

-continued

```
acaaacgtgc aacttgcttt tctacttcat cagatactta tgcctgctgg aatcattctg    18660
tgggttttga ctatgtctat aacccattta tgattgatgt tcagcagtgg ggctttacgg    18720
gtaaccttca gagtaaccat gaccaacatt gccaggtaca tggaaatgca catgtggcta    18780
gttgtgatgc tatcatgact agatgtttag cagtccatga gtgctttgtt aagcgcgttg    18840
attggtctgt tgaataccct attataggag atgaactgag ggttaattct gcttgcagaa    18900
aagtacaaca catggttgtg aagtctgcat tgcttgctga taagtttcca gttcttcatg    18960
acattggaaa tccaaaggct atcaagtgtg tgcctcaggc tgaagtagaa tggaagttct    19020
acgatgctca gccatgtagt gacaaagctt acaaaataga ggaactcttc tattcttatg    19080
ctacacatca cgataaattc actgatggtg tttgtttgtt ttggaattgt aacgttgatc    19140
gttacccagc caatgcaatt gtgtgtaggt ttgacacaag agtcttgtca aacttgaact    19200
taccaggctg tgatggtggt agtttgtatg tgaataagca tgcattccac actccagctt    19260
tcgataaaag tgcatttact aatttaaagc aattgccttt cttttactat tctgatagtc    19320
cttgtgagtc tcatggcaaa caagtagtgt cggatattga ttatgttcca ctcaaatctg    19380
ctacgtgtat tacacgatgc aatttaggtg gtgctgtttg cagacaccat gcaaatgagt    19440
accgacagta cttggatgca tataatatga tgatttctgc tggatttagc ctatggattt    19500
acaaacaatt tgatacttat aacctgtgga atacatttac caggttacag agtttagaaa    19560
atgtggctta taatgttgtt aataaaggac actttgatgg acacgccggc gaagcacctg    19620
tttccatcat taataatgct gtttacacaa aggtagatgg tattgatgtg gagatctttg    19680
aaaataagac aacacttcct gttaatgttg catttgagct ttgggctaag cgtaacatta    19740
aaccagtgcc agagattaag atactcaata atttgggtgt tgatatcgct gctaatactg    19800
taatctggga ctacaaaaga gaagccccag cacatgtatc tacaataggt gtctgcacaa    19860
tgactgacat tgccaagaaa cctactgaga gtgcttgttc ttcacttact gtcttgtttg    19920
atggtagagt ggaaggacag gtagaccttt ttagaaacgc ccgtaatggt gttttaataa    19980
cagaaggttc agtcaaaggt ctaacacctt caaagggacc agcacaagct agcgtcaatg    20040
gagtcacatt aattggagaa tcagtaaaaa cacagtttaa ctactttaag aaagtagacg    20100
gcattattca acagttgcct gaaacctact ttactcagag cagagactta gaggatttta    20160
agcccagatc acaaatggaa actgactttc tcgagctcgc tatggatgaa ttcatacagc    20220
gatataagct cgagggctat gccttcgaac acatcgttta tggagatttc agtcatggac    20280
aacttggcgg tcttcattta atgataggct agccaagcgc tcacaagat tcaccactta    20340
aattagagga ttttatccct atggacagca cagtgaaaaa ttacttcata acagatgcgc    20400
aaacaggttc atcaaaatgt gtgtgttctg tgattgatct tttacttgat gactttgtcg    20460
agataataaa gtcacaagat tgtcagtga tttcaaaagt ggtcaaggtt acaattgact    20520
atgctgaaat tcattcatg ctttggtgta aggatggaca tgttgaaacc ttctacccaa    20580
aactacaagc aagtcaagcg tggcaaccag tgttgcgat gcctaacttg tacaagatgc    20640
aaagaatgct tcttgaaaag tgtgaccttc agaattatgg tgaaaatgct gttataccaa    20700
aaggaataat gatgaatgtc gcaaagtata ctcaactgtg tcaatactta aatacactta    20760
cttttagctgt accctacaac atgagagtta ttcactttgg tgctggctct gataaaggag    20820
ttgcaccagg tacagctgta ctcagacaat ggttgccaac tggcacacta cttgtcgatt    20880
cagatcttaa tgacttcgtc tccgacgcag attctacttt aattggagac tgtgcaacag    20940
tacatacggc taataaatgg gaccttatta ttagcgatat gtatgacctt aagaccaaac    21000
```

```
atgtgacaaa agagaatgac tctaaagaag ggttttttcac ttatctgtgt ggatttataa    21060
agcaaaaact agccctgggt ggttctatag ctgtaaagat aacagagcat tcttggaatg    21120
ctgacccttta caagcttatg ggccatttct catggtggac agcttttgtt acaaatgtaa    21180
atgcatcatc atcggaagca ttttttaattg gggctaacta tcttggcaag ccgaaggaac    21240
aaattgatgg ctataccatg catgctaact acattttctg gaggaacaca aatcctatcc    21300
agttgtcttc ctattcactc tttgacatga gcaaatttcc tcttaaatta agaggaactg    21360
ctgtaatgtc tcttaaggag aatcaaatca atgatatgat ttattctctt ctggaaaaag    21420
gtaggcttat cattagagaa acaacagag ttgtggtttc aagtgatatt cttgttaata    21480
actaaacgaa catgtttatt ttcttattat ttcttactct cactagtggt agtgaccttg    21540
accggtgcac cacttttgat gatgttcaag ctcctaatta cactcaacat acttcatcta    21600
tgagggggt ttactatcct gatgaaattt ttagatcaga cactctttat ttaactcagg    21660
attttatttct tccatttat tctaatgtta cagggtttca tactattaat catacgtttg    21720
acaaccctgt catacctttt aaggatggta tttattttgc tgccacagag aaatcaaatg    21780
ttgtccgtgg ttgggttttt ggttctacca tgaacaacaa gtcacagtcg gtgattatta    21840
ttaacaattc tactaatgtt gttatacgag catgtaactt tgaattgtgt gacaacccctt    21900
tctttgctgt ttctaaaccc atgggtacac agacacatac tatgatattc gataatgcat    21960
ttaattgcac tttcgagtac atatctgatg ccttttcgct tgatgtttca gaaaagtcag    22020
gtaattttaa acacttacga gagtttgtgt ttaaaaataa agatgggttt ctctatgttt    22080
ataagggcta tcaacctata gatgtagttc gtgatctacc ttctggtttt aacactttga    22140
aacccatttt taagttgcct cttggtatta acattacaaa ttttagagcc attcttacag    22200
ccttttttacc tgctcaagac acttgggca cgtcagctgc agcctatttt gttggctatt    22260
taaagccaac tacattatatg ctcaagtatg atgaaaatgg tacaatcaca gatgctgttg    22320
attgttctca aaatccactt gctgaactca aatgctctgt taagagcttt gagattgaca    22380
aaggaattta ccagacctct aatttcaggg ttgttccctc aagagatgtt gtgagattcc    22440
ctaatattac aaacttgtgt cctttttggag aggttttttaa tgctactaaa ttcccttctg    22500
tctatgcatg ggagaggaaa agaatttcta attgtgttgc tgattactct gtgctctaca    22560
actcaacatt ttttttcaacc tttaagtgct atggcgtttc tgccactaag ttgaatgatc    22620
tttgcttctc caatgtctat gcagattctt ttgtagtcaa gggagatgat gtaagacaaa    22680
tagcgccagg acaaactggt gttattgctg attataatta taaattgcca gatgattttca    22740
tgggttgtgt ccttgcttgg aatactagga acattgatgc tacttcaact ggtaattata    22800
attataaata taggtatctt agacatggca agcttaggcc ctttgagaga gacatatcta    22860
atgtgcctttt ctcccctgat ggcaaaccctt gcacccccacc tgctcttaat tgttattggc    22920
cattaaatga ttatggtttt tacaccacta ctggcattgg ctaccaaccct acagagttg    22980
tagtactttc ttttgaactt ttaaatgcac cggccacggt ttgtggacca aaattatcca    23040
ctgaccttat taagaaccag tgtgtcaatt ttaatttaa tggactcact ggtactggtg    23100
tgttaactcc ttcttcaaag agatttcaac cattttcaaca attggccgt gatgtttctg    23160
atttcactga ttccgttcga gatcctaaaa catctgaaat attagacatt tcaccttgct    23220
cttttggggg tgtaagtgta attacaccctg gaacaaatgc ttcatctgaa gttgctgttc    23280
tatatcaaga tgttaactgc actgatgttt ctacagcaat tcatgcagat caactcacac    23340
```

```
cagcttggcg catatattct actggaaaca atgtattcca gactcaagca ggctgtctta   23400
taggagctga gcatgtcgac acttcttatg agtgcgacat tcctattgga gctggcattt   23460
gtgctagtta ccatacagtt tctttattac gtagtactag ccaaaaatct attgtggctt   23520
atactatgtc tttaggtgct gatagttcaa ttgcttactc taataacacc attgctatac   23580
ctactaactt ttcaattagc attactacag aagtaatgcc tgtttctatg ctaaaacct    23640 ccgtagattg taatatgtac atctgcggag attctactga atgtgctaat ttgcttctcc   23700
aatatggtag cttttgcaca caactaaatc gtgcactctc aggtattgct gctgaacagg   23760
atcgcaacac acgtgaagtg ttcgctcaag tcaaacaaat gtacaaaacc ccaactttga   23820
aagattttgg tggttttaat ttttcacaaa tattacctga ccctctaaag ccaactaaga   23880 ggtctttat tgaggacttg ctctttaata aggtgacact cgctgatgct ggcttcatga    23940
agcaatatgg cgaatgccta ggtgatatta tgctagaga tctcatttgt gcgcagaagt    24000
tcaatggact tacagtgttg ccacctctgc tcactgatga tatgattgct gcctacactg   24060
ctgctctagt tagtggtact gccactgctg gatggacatt tggtgctggc gctgctcttc   24120
aaataccttt tgctatgcaa atggcatata ggttcaatgg cattggagtt acccaaaatg   24180
ttctctatga gaaccaaaaa caaatcgcca accaatttaa caaggcgatt agtcaaattc   24240
aagaatcact tacaacaaca tcaactgcat gggcaagct gcaagacgtt gttaaccaga   24300
atgctcaagc attaaacaca cttgttaaac aacttagctc taattttggt gcaatttcaa   24360
gtgtgctaaa tgatatcctt tcgcgacttg ataaagtcga ggcggaggta caaattgaca   24420
ggttaattac aggcagactt caaagccttc aaacctatgt aacacaacaa ctaatcaggg   24480
ctgctgaaat cagggcttct gctaatcttg ctgctactaa aatgtctgag tgtgttcttg   24540
gacaatcaaa aagagttgac ttttgcggaa agggctacca ccttatgtcc ttcccacaag   24600
cagccccgca tggtgttgtc ttcctacatg tcacgtatgt gccatcccag gagaggaact   24660
tcaccacagc gccagcaatt tgtcatgaag gcaaagcata cttccctcgt gaaggtgttt   24720
ttgtgtttaa tggcacttct tggtttatta cacagaggaa cttctttttct ccacaaataa   24780 ttactacaga caatacattt gtctcaggaa attgtgatgt cgttattggc atcattaaca   24840 acacagtttta tgatcctctg caacctgagc ttgactcatt caagaagag ctggacaagt    24900 acttcaaaaa tcatacatca ccagatgttg atcttggcga catttcaggc attaacgctt   24960
ctgtcgtcaa cattcaagaa gaaattgacc gcctcaatga ggtcgctaaa aatttaaatg   25020
aatcactcat tgaccttcaa gaattgggaa aatatgagca atatattaaa tggccttggt   25080
atgtttggct cggcttcatt gctgactaa ttgccatcgt catggttaca atcttgcttt   25140
gttgcatgac tagttgttgc agttgcctca agggtgcatg ctcttgtggt tcttgctgca   25200
agtttgatga ggatgactct gagccagttc tcaagggtgt caaattacat tacacataaa   25260
cgaacttatg gatttgttta tgagattttt tactcttgga tcaattactg cacagccagt   25320
aaaaattgac aatgcttctc ctgcaagtac tgttcatgct acagcaacga taccgctaca   25380
agcctcactc ccttttcggat ggcttgttat tggcgttgca tttcttgctg ttttttcagag   25440 cgctaccaaa ataattgcgc tcaataaaag atggcagcta gccctttata agggcttcca   25500
gttcatttgc aatttactgc tgctatttgt taccatctat tcacatcttt tgcttgtcgc   25560
tgcaggtatg gaggcgcaat ttttgtacct ctatgccttg atatattttc tacaatgcat   25620
caacgcatgt agaattatta tgagatgttg gctttgttgg aagtgcaaat ccaagaaccc   25680
attactttat gatgccaact actttgtttg ctggcacaca cataactatg actactgtat   25740
```

```
accatataac agtgtcacag atacaattgt cgttactgca ggtgacggca tttcaacacc    25800
aaaactcaaa gaagactacc aaattggtgg ttattctgag gattggcact caggtgttaa    25860
agactatgtc gttgtacatg gctatttcac cgaagtttac taccagcttg agtctacaca    25920
aattactaca gacactggta ttgaaaatgc tacattcttc atctttaaca agcttgttaa    25980
agacccaccg aatgtgcaaa tacacacaat cgacggctct tcaggagttg caaatccagc    26040
aatggatcca atttatgatg agccgacgac gactactagc gtgcctttgt aagcacaaga    26100
aagtgagtac gaacttatgt actcattcgt ttcggaagaa acaggtacgt taatagttaa    26160
tagcgtactt cttttcttg ctttcgtggt attcttgcta gtcacactag ccatccttac    26220
tgcgcttcga ttgtgtgcgt actgctgcaa tattgttaac gtgagtttag taaaaccaac    26280
ggtttacgtc tactcgcgtg ttaaaaatct gaactcttct gaaggagttc ctgatcttct    26340
ggtctaaacg aactaactat tattattatt ctgtttggaa ctttaacatt gcttatcatg    26400
gcagacaacg gtactattac cgttgaggag cttaaacaac tcctggaaca atggaaccta    26460
gtaataggtt tcctattcct agcctggatt atgttactac aatttgccta ttctaatcgg    26520
aacaggtttt tgtacataat aaagcttgtt ttcctctggc tcttgtggcc agtaacactt    26580
gcttgctttg tgcttgctgc tgtctacaga attaattggg tgactggcgg gattgcgatt    26640
gcaatggctt gtattgtagg cttgatgtgg cttagctact tcgttgcttc cttcaggctg    26700
tttgctcgta cccgctcaat gtggtcattc aacccagaaa caaacattct tctcaatgtg    26760
cctctccggg ggacaattgt gaccagaccg ctcatgaaa gtgaacttgt cattggtgct    26820
gtgatcattc gtggtcactt gcgaatggcc ggacactccc tagggcgctg tgacattaag    26880
gacctgccaa aagagatcac tgtggctaca tcacgaacgc tttcttatta caaattagga    26940
gcgtcgcagc gtgtaggcac tgattcaggt tttgctgcat acaaccgcta ccgtattgga    27000
aactataaat taaatacaga ccacgccggt agcaacgaca atattgcttt gctagtacag    27060
taagtgacaa cagatgtttc atcttgttga cttccaggtt acaatagcag agatattgat    27120
tatcattatg aggactttca ggattgctat ttggaatctt gacgttataa taagttcaat    27180
agtgagacaa ttatttaagc ctctaactaa gaagaattat tcggagttag atgatgaaga    27240
acctatggag ttagattatc cataaaacga acatgaaaat tattctcttc ctgacattga    27300
ttgtatttac atcttgcgag ctatatcact atcaggagtg tgttagaggt acgactgtac    27360
tactaaaaga accttgccca tcaggaacat acgagggcaa ttcaccattt caccctcttg    27420
ctgacaataa atttgcacta acttgcacta gcacacactt tgcttttgct tgtgctgacg    27480
gtactcgaca tacctatcag ctgcgtgcaa gatcagtttc accaaaactt ttcatcagac    27540
aagaggaggt tcaacaagag ctctactcgc cacttttct cattgttgct gctctagtat    27600
ttttaatact ttgcttcacc attaagagaa agacagaatg aatgagctca ctttaattga    27660
cttctatttg tgcttttag cctttctgct attccttgtt ttaataatgc ttattatatt    27720
ttggttttca ctcgaaatcc aggatctaga agaaccttgt accaaagtct aaacgaacat    27780
gaaacttctc attgttttga cttgtatttc tctatgcagt tgcatacgca ctgtagtaca    27840
gcgctgtgca tctaataaac ctcatgtgct tgaagatcct tgtcctactg gttaccaacc    27900
tgaatggaat ataaggtaca acactagggg taatacttat agcactgctt ggcttgtgc    27960 tctaggaaag gttttacctt ttcatagatg gcacactatg gttcaaacat gcacacctaa    28020
tgttactatc aactgtcaag atccagctgg tggtgcgctt atagctaggt gttggtacct    28080
```

```
tcatgaaggt caccaaactg ctgcatttag agacgtattt gttgttttaa ataaacgaac    28140
aaattaaaat gtctgataat ggaccccaat caaaccaacg tagtgccccc cgcattacat    28200
ttggtggacc cacagattca actgacaata accagaatgg aggacgcaat ggggcaaggc    28260
caaaacagcg ccgaccccaa ggtttaccca ataatactgc gtcttggttc acagctctca    28320
ctcagcatgg caaggaggaa cttagattcc ctcgaggcca gggcgttcca atcaacacca    28380
atagtggtcc agatgaccaa attggctact accgaagagc tacccgacga gttcgtggtg    28440
gtgacggcaa aatgaaagag ctcagcccca gatggtactt ctattaccta ggaactggcc    28500
cagaagcttc acttccctac ggcgctaaca agaaggcat cgtatgggtt gcaactgagg    28560
gagccttgaa tacacccaaa gaccacattg gcacccgcaa tcctaataac aatgctgcca    28620
ccgtgctaca acttcctcaa ggaacaacat tgccaaaagg cttctacgca gagggaagca    28680
gaggcggcag tcaagcctct tctcgctcct catcacgtag tcgcggtaat tcaagaaatt    28740
caactcctgg cagcagtagg ggaaattctc ctgctcgaat ggctagcgga ggtggtgaaa    28800
ctgccctcgc gctattgctg ctagacagat tgaaccagct tgagagcaaa gtttctggta    28860
aaggccaaca caacaaggc caaactgtca ctaagaaatc tgctgctgag gcatctaaaa    28920
agcctcgcca aaaacgtact gccacaaaac agtacaacgt cactcaagca tttgggagac    28980
gtggtccaga acaaacccaa ggaaatttcg ggaccaaga cctaatcaga caaggaactg    29040
attacaaaca ttggccgcaa attgcacaat ttgctccaag tgcctctgca ttctttggaa    29100
tgtcacgcat tggcatggaa gtcacacctt cgggaacatg gctgacttat catggagcca    29160
ttaaattgga tgacaaagat ccacaattca agacaacgt catactgctg aacaagcaca    29220
ttgacgcata caaacattc ccaccaacag agcctaaaaa ggacaaaaag aaaaaaactg    29280
atgaagctca gccttttgccg cagagacaaa agaagcagcc cactgtgact cttcttcctg    29340
cggctgacat ggatgatttc tccagacaac ttcaaaattc catgagtgga gcttctgctg    29400
attcaactca ggcataaaca ctcatgatga ccacacaagg cagatgggct atgtaaacgt    29460
tttcgcaatt ccgtttacga tacatagtct actcttgtgc agaatgaatt ctcgtaacta    29520
aacagcacaa gtaggtttag ttaactttaa tctcacatag caatctttaa tcaatgtgta    29580
acattaggga ggacttgaaa gagccaccac attttcatcg aggccacgcg gagtacgatc    29640
gagggtacag tgaataatgc tagggagagc tgcctatatg gaagagccct aatgtgtaaa    29700 attaattta gtagtgctat ccccatgtga ttttaatagc ttcttaggag aatgacaaaa    29760
```

<210> SEQ ID NO 2
<211> LENGTH: 29
<212> TYPE: DNA
<213> ORGANISM: SARS Coronavirus

<400> SEQUENCE: 2
cctactggtt accaacctga atggaatat                                          29

<210> SEQ ID NO 3
<211> LENGTH: 53
<212> TYPE: DNA
<213> ORGANISM: SARS Coronavirus

<400> SEQUENCE: 3
aacctcatgt gcttgaagat ccttgtaagg tacaacacta ggggtaatac tta              53

<210> SEQ ID NO 4
<211> LENGTH: 3768

-continued

<212> TYPE: DNA
<213> ORGANISM: SARS Coronavirus
<220> FEATURE:
<221> NAME/KEY: CDS
<222> LOCATION: (1)..(3768)

<400> SEQUENCE: 4 atg ttt att ttc tta tta ttt ctt act ctc act agt ggt agt gac ctt 48
Met Phe Ile Phe Leu Leu Phe Leu Thr Leu Thr Ser Gly Ser Asp Leu
1 5 10 15 gac cgg tgc acc act ttt gat gat gtt caa gct cct aat tac act caa 96
Asp Arg Cys Thr Thr Phe Asp Asp Val Gln Ala Pro Asn Tyr Thr Gln
20 25 30 cat act tca tct atg agg ggg gtt tac tat cct gat gaa att ttt aga 144
His Thr Ser Ser Met Arg Gly Val Tyr Tyr Pro Asp Glu Ile Phe Arg
35 40 45 tca gac act ctt tat tta act cag gat tta ttt ctt cca ttt tat tct 192
Ser Asp Thr Leu Tyr Leu Thr Gln Asp Leu Phe Leu Pro Phe Tyr Ser
50 55 60 aat gtt aca ggg ttt cat act att aat cat acg ttt gac aac cct gtc 240
Asn Val Thr Gly Phe His Thr Ile Asn His Thr Phe Asp Asn Pro Val
65 70 75 80 ata cct ttt aag gat ggt att tat ttt gct gcc aca gag aaa tca aat 288
Ile Pro Phe Lys Asp Gly Ile Tyr Phe Ala Ala Thr Glu Lys Ser Asn
85 90 95 gtt gtc cgt ggt tgg gtt ttt ggt tct acc atg aac aac aag tca cag 336
Val Val Arg Gly Trp Val Phe Gly Ser Thr Met Asn Asn Lys Ser Gln
100 105 110 tcg gtg att att att aac aat tct act aat gtt gtt ata cga gca tgt 384
Ser Val Ile Ile Ile Asn Asn Ser Thr Asn Val Val Ile Arg Ala Cys
115 120 125 aac ttt gaa ttg tgt gac aac cct ttc ttt gct gtt tct aaa ccc atg 432
Asn Phe Glu Leu Cys Asp Asn Pro Phe Phe Ala Val Ser Lys Pro Met
130 135 140 ggt aca cag aca cat act atg ata ttc gat aat gca ttt aat tgc act 480
Gly Thr Gln Thr His Thr Met Ile Phe Asp Asn Ala Phe Asn Cys Thr
145 150 155 160 ttc gag tac ata tct gat gcc ttt tcg ctt gat gtt tca gaa aag tca 528
Phe Glu Tyr Ile Ser Asp Ala Phe Ser Leu Asp Val Ser Glu Lys Ser
165 170 175 ggt aat ttt aaa cac tta cga gag ttt gtg ttt aaa aat aaa gat ggg 576
Gly Asn Phe Lys His Leu Arg Glu Phe Val Phe Lys Asn Lys Asp Gly
180 185 190 ttt ctc tat gtt tat aag ggc tat caa cct ata gat gta gtt cgt gat 624
Phe Leu Tyr Val Tyr Lys Gly Tyr Gln Pro Ile Asp Val Val Arg Asp
195 200 205 cta cct tct ggt ttt aac act ttg aaa ccc att ttt aag ttg cct ctt 672
Leu Pro Ser Gly Phe Asn Thr Leu Lys Pro Ile Phe Lys Leu Pro Leu
210 215 220 ggt att aac att aca aat ttt aga gcc att ctt aca gcc ttt tta cct 720
Gly Ile Asn Ile Thr Asn Phe Arg Ala Ile Leu Thr Ala Phe Leu Pro
225 230 235 240 gct caa gac act tgg ggc acg tca gct gca gcc tat ttt gtt ggc tat 768
Ala Gln Asp Thr Trp Gly Thr Ser Ala Ala Ala Tyr Phe Val Gly Tyr
245 250 255 tta aag cca act aca ttt atg ctc aag tat gat gaa aat ggt aca atc 816
Leu Lys Pro Thr Thr Phe Met Leu Lys Tyr Asp Glu Asn Gly Thr Ile
260 265 270 aca gat gct gtt gat tgt tct caa aat cca ctt gct gaa ctc aaa tgc 864
Thr Asp Ala Val Asp Cys Ser Gln Asn Pro Leu Ala Glu Leu Lys Cys
275 280 285

-continued

```
tct gtt aag agc ttt gag att gac aaa gga att tac cag acc tct aat    912
Ser Val Lys Ser Phe Glu Ile Asp Lys Gly Ile Tyr Gln Thr Ser Asn
290                 295                 300 ttc agg gtt gtt ccc tca aga gat gtt gtg aga ttc cct aat att aca    960
Phe Arg Val Val Pro Ser Arg Asp Val Val Arg Phe Pro Asn Ile Thr
305                 310                 315                 320 aac ttg tgt cct ttt gga gag gtt ttt aat gct act aaa ttc cct tct   1008
Asn Leu Cys Pro Phe Gly Glu Val Phe Asn Ala Thr Lys Phe Pro Ser
                325                 330                 335 gtc tat gca tgg gag agg aaa aga att tct aat tgt gtt gct gat tac   1056
Val Tyr Ala Trp Glu Arg Lys Arg Ile Ser Asn Cys Val Ala Asp Tyr
340                 345                 350 tct gtg ctc tac aac tca aca ttt ttt tca acc ttt aag tgc tat ggc   1104
Ser Val Leu Tyr Asn Ser Thr Phe Phe Ser Thr Phe Lys Cys Tyr Gly
355                 360                 365 gtt tct gcc act aag ttg aat gat ctt tgc ttc tcc aat gtc tat gca   1152
Val Ser Ala Thr Lys Leu Asn Asp Leu Cys Phe Ser Asn Val Tyr Ala
370                 375                 380 gat tct ttt gta gtc aag gga gat gat gta aga caa ata gcg cca gga   1200
Asp Ser Phe Val Val Lys Gly Asp Asp Val Arg Gln Ile Ala Pro Gly
385                 390                 395                 400 caa act ggt gtt att gct gat tat aat tat aaa ttg cca gat gat ttc   1248
Gln Thr Gly Val Ile Ala Asp Tyr Asn Tyr Lys Leu Pro Asp Asp Phe
                405                 410                 415 atg ggt tgt gtc ctt gct tgg aat act agg aac att gat gct act tca   1296
Met Gly Cys Val Leu Ala Trp Asn Thr Arg Asn Ile Asp Ala Thr Ser
                420                 425                 430 act ggt aat tat aat tat aaa tat agg tat ctt aga cat ggc aag ctt   1344
Thr Gly Asn Tyr Asn Tyr Lys Tyr Arg Tyr Leu Arg His Gly Lys Leu
435                 440                 445 agg ccc ttt gag aga gac ata tct aat gtg cct ttc tcc cct gat ggc   1392
Arg Pro Phe Glu Arg Asp Ile Ser Asn Val Pro Phe Ser Pro Asp Gly
450                 455                 460 aaa cct tgc acc cca cct gct ctt aat tgt tat tgg cca tta aat gat   1440
Lys Pro Cys Thr Pro Pro Ala Leu Asn Cys Tyr Trp Pro Leu Asn Asp
465                 470                 475                 480 tat ggt ttt tac acc act act ggc att ggc tac caa cct tac aga gtt   1488
Tyr Gly Phe Tyr Thr Thr Thr Gly Ile Gly Tyr Gln Pro Tyr Arg Val
                485                 490                 495 gta gta ctt tct ttt gaa ctt tta aat gca ccg gcc acg gtt tgt gga   1536
Val Val Leu Ser Phe Glu Leu Leu Asn Ala Pro Ala Thr Val Cys Gly
                500                 505                 510 cca aaa tta tcc act gac ctt att aag aac cag tgt gtc aat ttt aat   1584
Pro Lys Leu Ser Thr Asp Leu Ile Lys Asn Gln Cys Val Asn Phe Asn
                515                 520                 525 ttt aat gga ctc act ggt act ggt gtg tta act cct tct tca aag aga   1632
Phe Asn Gly Leu Thr Gly Thr Gly Val Leu Thr Pro Ser Ser Lys Arg
530                 535                 540 ttt caa cca ttt caa caa ttt ggc cgt gat gtt tct gat ttc act gat   1680
Phe Gln Pro Phe Gln Gln Phe Gly Arg Asp Val Ser Asp Phe Thr Asp
545                 550                 555                 560 tcc gtt cga gat cct aaa aca tct gaa ata tta gac att tca cct tgc   1728
Ser Val Arg Asp Pro Lys Thr Ser Glu Ile Leu Asp Ile Ser Pro Cys
                565                 570                 575 tct ttt ggg ggt gta agt gta att aca cct gga aca aat gct tca tct   1776
Ser Phe Gly Gly Val Ser Val Ile Thr Pro Gly Thr Asn Ala Ser Ser
                580                 585                 590 gaa gtt gct gtt cta tat caa gat gtt aac tgc act gat gtt tct aca   1824
Glu Val Ala Val Leu Tyr Gln Asp Val Asn Cys Thr Asp Val Ser Thr
```

```
                    595                 600                 605
gca att cat gca gat caa ctc aca cca gct tgg cgc ata tat tct act      1872
Ala Ile His Ala Asp Gln Leu Thr Pro Ala Trp Arg Ile Tyr Ser Thr
        610                 615                 620 gga aac aat gta ttc cag act caa gca ggc tgt ctt ata gga gct gag      1920
Gly Asn Asn Val Phe Gln Thr Gln Ala Gly Cys Leu Ile Gly Ala Glu
625                 630                 635                 640 cat gtc gac act tct tat gag tgc gac att cct att gga gct ggc att      1968
His Val Asp Thr Ser Tyr Glu Cys Asp Ile Pro Ile Gly Ala Gly Ile
                645                 650                 655 tgt gct agt tac cat aca gtt tct tta tta cgt agt act agc caa aaa      2016
Cys Ala Ser Tyr His Thr Val Ser Leu Leu Arg Ser Thr Ser Gln Lys
            660                 665                 670 tct att gtg gct tat act atg tct tta ggt gct gat agt tca att gct      2064
Ser Ile Val Ala Tyr Thr Met Ser Leu Gly Ala Asp Ser Ser Ile Ala
        675                 680                 685 tac tct aat aac acc att gct ata cct act aac ttt tca att agc att      2112
Tyr Ser Asn Asn Thr Ile Ala Ile Pro Thr Asn Phe Ser Ile Ser Ile
    690                 695                 700 act aca gaa gta atg cct gtt tct atg gct aaa acc tcc gta gat tgt      2160
Thr Thr Glu Val Met Pro Val Ser Met Ala Lys Thr Ser Val Asp Cys
705                 710                 715                 720 aat atg tac atc tgc gga gat tct act gaa tgt gct aat ttg ctt ctc      2208
Asn Met Tyr Ile Cys Gly Asp Ser Thr Glu Cys Ala Asn Leu Leu Leu
                725                 730                 735 caa tat ggt agc ttt tgc aca caa cta aat cgt gca ctc tca ggt att      2256
Gln Tyr Gly Ser Phe Cys Thr Gln Leu Asn Arg Ala Leu Ser Gly Ile
            740                 745                 750 gct gct gaa cag gat cgc aac aca cgt gaa gtg ttc gct caa gtc aaa      2304
Ala Ala Glu Gln Asp Arg Asn Thr Arg Glu Val Phe Ala Gln Val Lys
        755                 760                 765 caa atg tac aaa acc cca act ttg aaa gat ttt ggt ggt ttt aat ttt      2352
Gln Met Tyr Lys Thr Pro Thr Leu Lys Asp Phe Gly Gly Phe Asn Phe
    770                 775                 780 tca caa ata tta cct gac cct cta aag cca act aag agg tct ttt att      2400
Ser Gln Ile Leu Pro Asp Pro Leu Lys Pro Thr Lys Arg Ser Phe Ile
785                 790                 795                 800 gag gac ttg ctc ttt aat aag gtg aca ctc gct gat gct ggc ttc atg      2448
Glu Asp Leu Leu Phe Asn Lys Val Thr Leu Ala Asp Ala Gly Phe Met
                805                 810                 815 aag caa tat ggc gaa tgc cta ggt gat att aat gct aga gat ctc att      2496
Lys Gln Tyr Gly Glu Cys Leu Gly Asp Ile Asn Ala Arg Asp Leu Ile
            820                 825                 830 tgt gcg cag aag ttc aat gga ctt aca gtg ttg cca cct ctg ctc act      2544
Cys Ala Gln Lys Phe Asn Gly Leu Thr Val Leu Pro Pro Leu Leu Thr
        835                 840                 845 gat gat atg att gct gcc tac act gct gct cta gtt agt ggt act gcc      2592
Asp Asp Met Ile Ala Ala Tyr Thr Ala Ala Leu Val Ser Gly Thr Ala
    850                 855                 860 act gct gga tgg aca ttt ggt gct ggc gct gct ctt caa ata cct ttt      2640
Thr Ala Gly Trp Thr Phe Gly Ala Gly Ala Ala Leu Gln Ile Pro Phe
865                 870                 875                 880 gct atg caa atg gca tat agg ttc aat ggc att gga gtt acc caa aat      2688
Ala Met Gln Met Ala Tyr Arg Phe Asn Gly Ile Gly Val Thr Gln Asn
                885                 890                 895 gtt ctc tat gag aac caa aaa caa atc gcc aac caa ttt aac aag gcg      2736
Val Leu Tyr Glu Asn Gln Lys Gln Ile Ala Asn Gln Phe Asn Lys Ala
            900                 905                 910 att agt caa att caa gaa tca ctt aca aca aca tca act gca ttg ggc      2784
```

```
Ile Ser Gln Ile Gln Glu Ser Leu Thr Thr Thr Ser Thr Ala Leu Gly
        915                 920                 925 aag ctg caa gac gtt gtt aac cag aat gct caa gca tta aac aca ctt    2832
Lys Leu Gln Asp Val Val Asn Gln Asn Ala Gln Ala Leu Asn Thr Leu
930                 935                 940 gtt aaa caa ctt agc tct aat ttt ggt gca att tca agt gtg cta aat    2880
Val Lys Gln Leu Ser Ser Asn Phe Gly Ala Ile Ser Ser Val Leu Asn
945                 950                 955                 960 gat atc ctt tcg cga ctt gat aaa gtc gag gcg gag gta caa att gac    2928
Asp Ile Leu Ser Arg Leu Asp Lys Val Glu Ala Glu Val Gln Ile Asp
                965                 970                 975 agg tta att aca ggc aga ctt caa agc ctt caa acc tat gta aca caa    2976
Arg Leu Ile Thr Gly Arg Leu Gln Ser Leu Gln Thr Tyr Val Thr Gln
            980                 985                 990 caa cta atc agg gct gct gaa atc agg gct tct gct aat ctt gct gct    3024
Gln Leu Ile Arg Ala Ala Glu Ile Arg Ala Ser Ala Asn Leu Ala Ala
        995                 1000                1005 act aaa atg tct gag tgt gtt ctt gga caa tca aaa aga gtt gac        3069
Thr Lys Met Ser Glu Cys Val Leu Gly Gln Ser Lys Arg Val Asp
    1010                1015                1020 ttt tgc gga aag ggc tac cac ctt atg tcc ttc cca caa gca gcc        3114
Phe Cys Gly Lys Gly Tyr His Leu Met Ser Phe Pro Gln Ala Ala
    1025                1030                1035 ccg cat ggt gtt gtc ttc cta cat gtc acg tat gtg cca tcc cag        3159
Pro His Gly Val Val Phe Leu His Val Thr Tyr Val Pro Ser Gln
    1040                1045                1050 gag agg aac ttc acc aca gcg cca gca att tgt cat gaa ggc aaa        3204
Glu Arg Asn Phe Thr Thr Ala Pro Ala Ile Cys His Glu Gly Lys
    1055                1060                1065 gca tac ttc cct cgt gaa ggt gtt ttt gtg ttt aat ggc act tct        3249
Ala Tyr Phe Pro Arg Glu Gly Val Phe Val Phe Asn Gly Thr Ser
    1070                1075                1080 tgg ttt att aca cag agg aac ttc ttt tct cca caa ata att act        3294
Trp Phe Ile Thr Gln Arg Asn Phe Phe Ser Pro Gln Ile Ile Thr
    1085                1090                1095 aca gac aat aca ttt gtc tca gga aat tgt gat gtc gtt att ggc        3339
Thr Asp Asn Thr Phe Val Ser Gly Asn Cys Asp Val Val Ile Gly
    1100                1105                1110 atc att aac aac aca gtt tat gat cct ctg caa cct gag ctt gac        3384
Ile Ile Asn Asn Thr Val Tyr Asp Pro Leu Gln Pro Glu Leu Asp
    1115                1120                1125 tca ttc aaa gaa gag ctg gac aag tac ttc aaa aat cat aca tca        3429
Ser Phe Lys Glu Glu Leu Asp Lys Tyr Phe Lys Asn His Thr Ser
    1130                1135                1140 cca gat gtt gat ctt ggc gac att tca ggc att aac gct tct gtc        3474
Pro Asp Val Asp Leu Gly Asp Ile Ser Gly Ile Asn Ala Ser Val
    1145                1150                1155 gtc aac att caa gaa gaa att gac cgc ctc aat gag gtc gct aaa        3519
Val Asn Ile Gln Glu Glu Ile Asp Arg Leu Asn Glu Val Ala Lys
    1160                1165                1170 aat tta aat gaa tca ctc att gac ctt caa gaa ttg gga aaa tat        3564
Asn Leu Asn Glu Ser Leu Ile Asp Leu Gln Glu Leu Gly Lys Tyr
    1175                1180                1185 gag caa tat att aaa tgg cct tgg tat gtt tgg ctc ggc ttc att        3609
Glu Gln Tyr Ile Lys Trp Pro Trp Tyr Val Trp Leu Gly Phe Ile
    1190                1195                1200 gct gga cta att gcc atc gtc atg gtt aca atc ttg ctt tgt tgc        3654
Ala Gly Leu Ile Ala Ile Val Met Val Thr Ile Leu Leu Cys Cys
    1205                1210                1215
```

-continued

| | | | | | | | | | | | | |
|---|---|---|---|---|---|---|---|---|---|---|---|---|
| atg | act | agt | tgt | tgc | agt | tgc | ctc | aag | ggt | gca | tgc | tct tgt ggt | 3699 |
| Met | Thr | Ser | Cys | Cys | Ser | Cys | Leu | Lys | Gly | Ala | Cys | Ser Cys Gly |
| | 1220 | | | | 1225 | | | | | 1230 | | |
| tct | tgc | tgc | aag | ttt | gat | gag | gat | gac | tct | gag | cca | gtt ctc aag | 3744 |
| Ser | Cys | Cys | Lys | Phe | Asp | Glu | Asp | Asp | Ser | Glu | Pro | Val Leu Lys |
| | 1235 | | | | 1240 | | | | | 1245 | | |
| ggt | gtc | aaa | tta | cat | tac | aca | taa | | | | | | 3768 |
| Gly | Val | Lys | Leu | His | Tyr | Thr | | | | | | |
| | 1250 | | | | 1255 | | | | | | | |

<210> SEQ ID NO 5
<211> LENGTH: 1255
<212> TYPE: PRT
<213> ORGANISM: SARS Coronavirus

<400> SEQUENCE: 5

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Asp Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Leu Pro
225                 230                 235                 240

Ala Gln Asp Thr Trp Gly Thr Ser Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Arg Asp Val Val Arg Phe Pro Asn Ile Thr
305                 310                 315                 320

-continued

```
Asn Leu Cys Pro Phe Gly Glu Val Phe Asn Ala Thr Lys Phe Pro Ser
                325                 330                 335

Val Tyr Ala Trp Glu Arg Lys Arg Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735
```

```
Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Asp Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Glu Glu Leu Asp  Lys Tyr Phe Lys Asn  His Thr Ser
    1130                1135                1140

Pro Asp  Val Asp Leu Gly Asp  Ile Ser Gly Ile Asn  Ala Ser Val
```

-continued

```
                1145                1150                1155
Val Asn Ile Gln Glu Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255

<210> SEQ ID NO 6
<211> LENGTH: 30
<212> TYPE: DNA
<213> ORGANISM: Artificial
<220> FEATURE:
<223> OTHER INFORMATION: PCR Sense Primer

<400> SEQUENCE: 6 gcacccacc tgctcttaat tgttattggc                                30

<210> SEQ ID NO 7
<211> LENGTH: 30
<212> TYPE: DNA
<213> ORGANISM: Artificial
<220> FEATURE:
<223> OTHER INFORMATION: PCR Anti-sense Primer

<400> SEQUENCE: 7
tattaaagag caagtcctca ataaaagacc                                30
```